(12) United States Patent
Chou et al.

(10) Patent No.: US 12,403,465 B2
(45) Date of Patent: Sep. 2, 2025

(54) CONTAINING A LIQUID SAMPLE

(71) Applicant: Essenlix Corporation, Monmouth Junction, NJ (US)

(72) Inventors: Stephen Y. Chou, Princeton, NJ (US); Wei Ding, East Windsor, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 16/755,842

(22) PCT Filed: Oct. 11, 2018

(86) PCT No.: PCT/US2018/055474
§ 371 (c)(1),
(2) Date: Apr. 13, 2020

(87) PCT Pub. No.: WO2019/075244
PCT Pub. Date: Apr. 18, 2019

(65) Prior Publication Data
US 2020/0276576 A1    Sep. 3, 2020

Related U.S. Application Data

(60) Provisional application No. 62/571,069, filed on Oct. 11, 2017.

(51) Int. Cl.
*G01N 1/28*     (2006.01)
*B01L 3/00*     (2006.01)
*G01N 21/25*    (2006.01)
*G01N 21/64*    (2006.01)
*G01N 33/02*    (2006.01)

(52) U.S. Cl.
CPC ............. *B01L 3/502* (2013.01); *G01N 21/25* (2013.01); *G01N 21/64* (2013.01); *G01N 33/02* (2013.01); *B01L 2300/023* (2013.01); *B01L 2300/025* (2013.01); *B01L 2300/0627* (2013.01); *B01L 2300/0829* (2013.01); *B01L 2300/0858* (2013.01); *B01L 2300/123* (2013.01); *B01L 2300/168* (2013.01)

(58) Field of Classification Search
None
See application file for complete search history.

(56) References Cited

U.S. PATENT DOCUMENTS 3,368,872 A    2/1968 Natelson
3,447,863 A    6/1969 Patterson
(Continued)

FOREIGN PATENT DOCUMENTS

AU    1378988 A    9/1988
AU     619459 B    1/1992
(Continued)

OTHER PUBLICATIONS

Van Vliet, Dillys et al., Prediction of asthma exacerbations in children by innovative exhaled inflammatory markers: Results of a longitudinal study, PLOS One, Mar. 23, 2015, vol. 10. No. 3, e0119434.
(Continued)

*Primary Examiner* — Paul S Hyun

(57) ABSTRACT

Among other things, the present disclosure is related to devices and methods for containing a liquid sample between two plates.

46 Claims, 23 Drawing Sheets

(56) References Cited

U.S. PATENT DOCUMENTS

| | | |
|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,348,859 A | 9/1994 | Brunhouse et al. |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,083,761 A | 7/2000 | Kedar et al. |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,223,604 B1 * | 5/2007 | Liu .................. G01N 33/721 |
| | | 436/66 |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |

(56) References Cited

U.S. PATENT DOCUMENTS

| | | |
|---|---|---|
| 9,523,670 B2 | 12/2016 | Mueller et al. |
| 9,696,252 B2 | 7/2017 | Wardlaw |
| 2001/0055882 A1 | 12/2001 | Ostuni |
| 2002/0001855 A1 | 1/2002 | Prentiss et al. |
| 2002/0106314 A1 | 8/2002 | Pelrine et al. |
| 2002/0164820 A1 | 11/2002 | Brown |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0019936 A1* | 1/2005 | Samsoondar ........... B01L 3/508 436/80 |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0212462 A1 | 9/2011 | Duffy et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2012/0321518 A1 | 12/2012 | Ermantraut et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0252847 A1 | 9/2013 | Mckenna et al. |
| 2013/0265054 A1 | 10/2013 | Lowery et al. |
| 2013/0309679 A1 | 11/2013 | Ismagilov et al. |
| 2014/0273272 A1 | 9/2014 | Gayda et al. |
| 2014/0315242 A1 | 10/2014 | Rodriguez et al. |
| 2014/0323330 A1 | 10/2014 | Bergo |
| 2014/0368631 A1 | 12/2014 | Wardlaw et al. |
| 2014/0378320 A1 | 12/2014 | Hoffmann et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | |
|---|---|---|
| CN | 1299466 A | 6/2001 |
| CN | 1302229 A | 7/2001 |
| CN | 1166950 C | 9/2004 |
| CN | 1188217 C | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 3026433 | 6/2016 |
| EP | 1949310 B1 | 2/2019 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014183049 | 11/2014 |
| WO | 2014205576 | 12/2014 |
| WO | 2016081941 A1 | 5/2016 |

OTHER PUBLICATIONS

International Report on Patentability for PCT/US2018/037168 established by IPEA/US mailed on Aug. 19, 2019.

International search report for application PCT/US2018/055474 mailed on Jan. 7, 2019.

\* cited by examiner

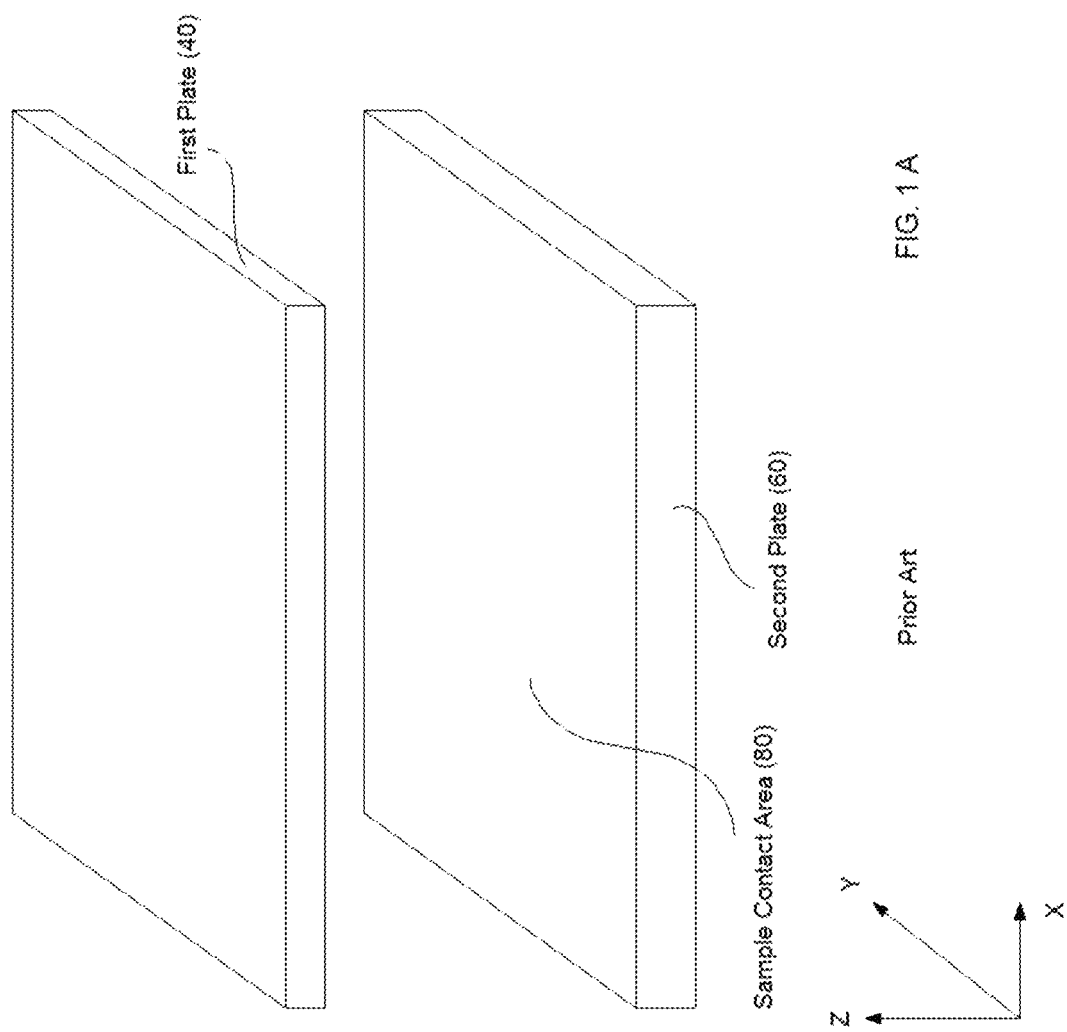

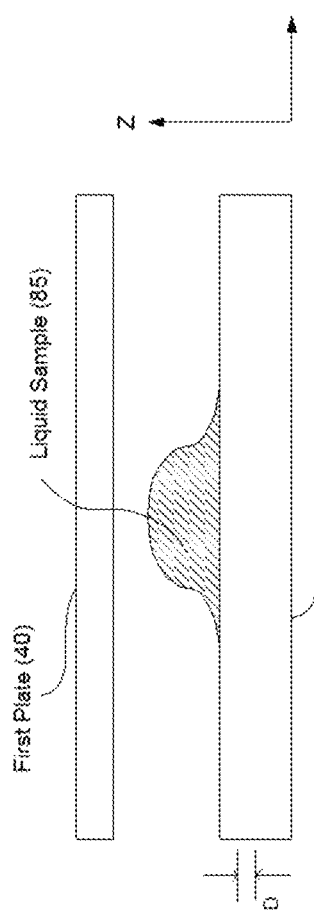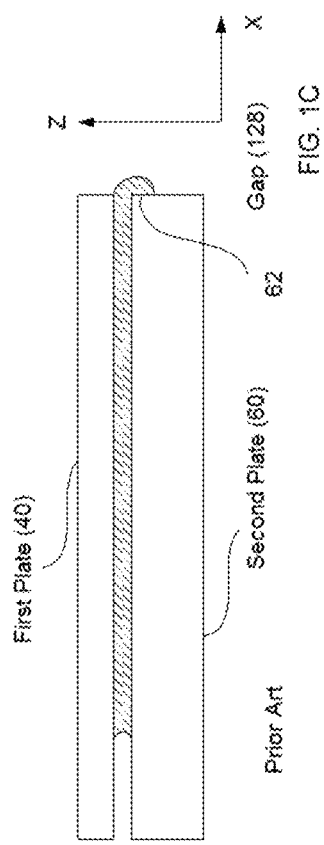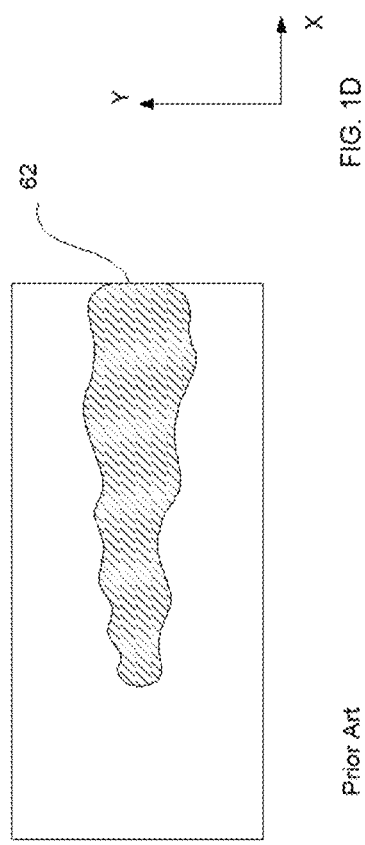

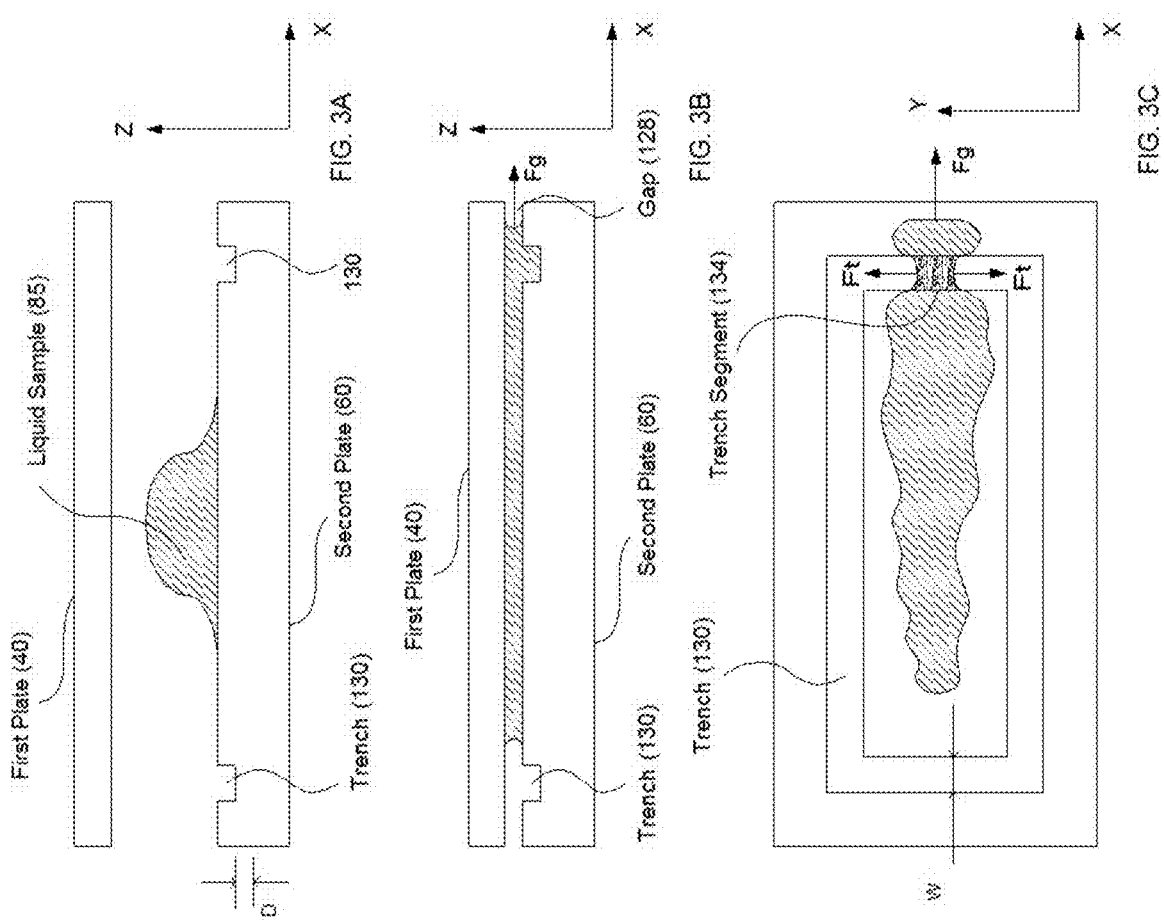

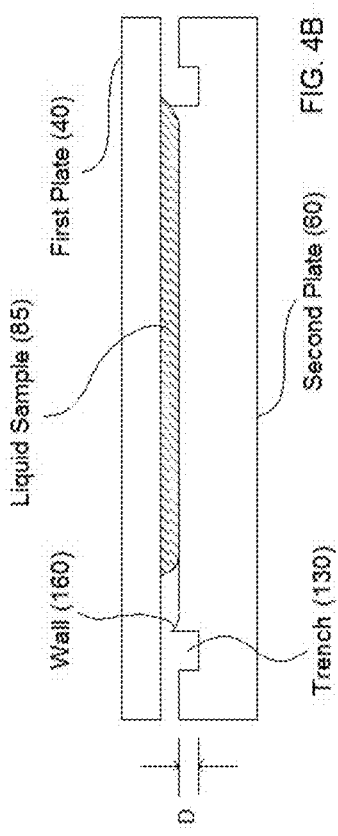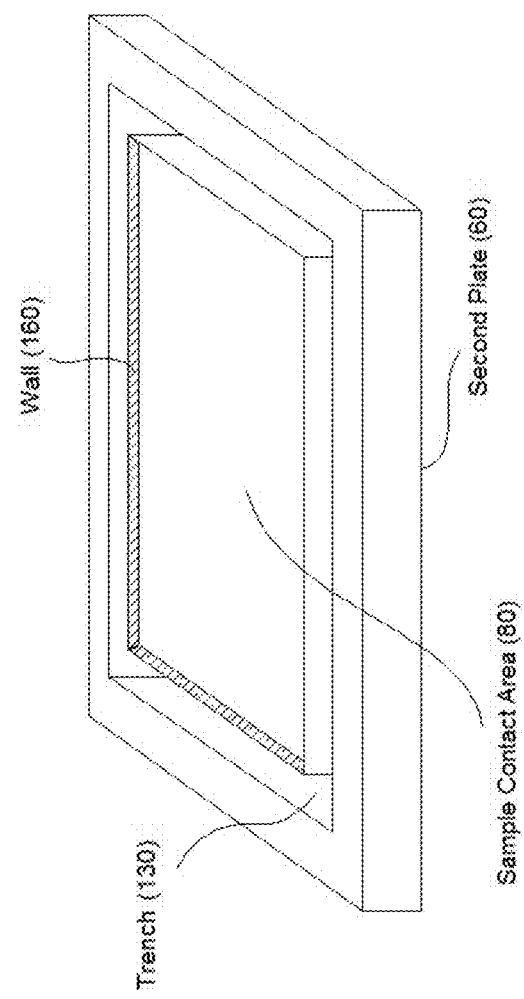

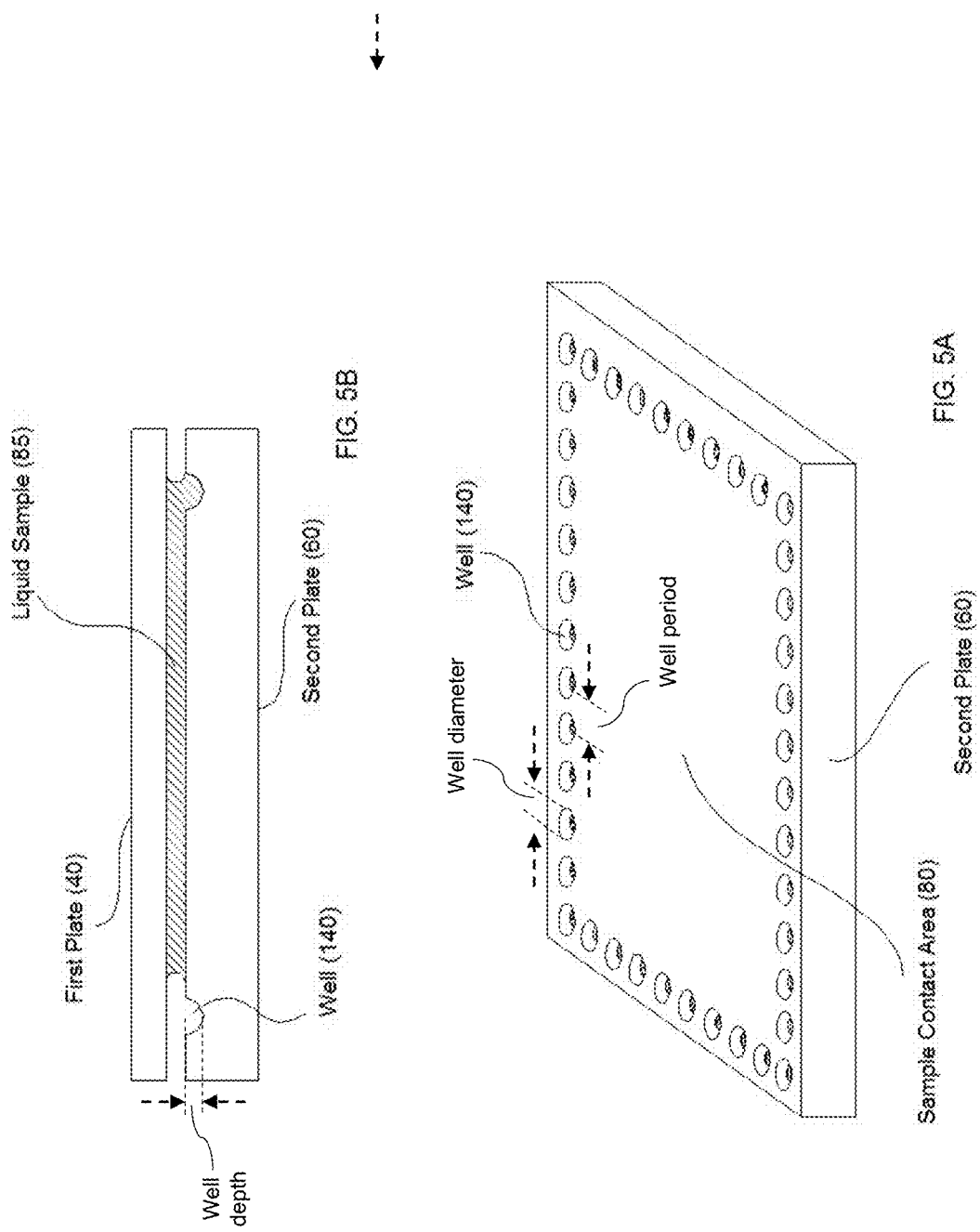

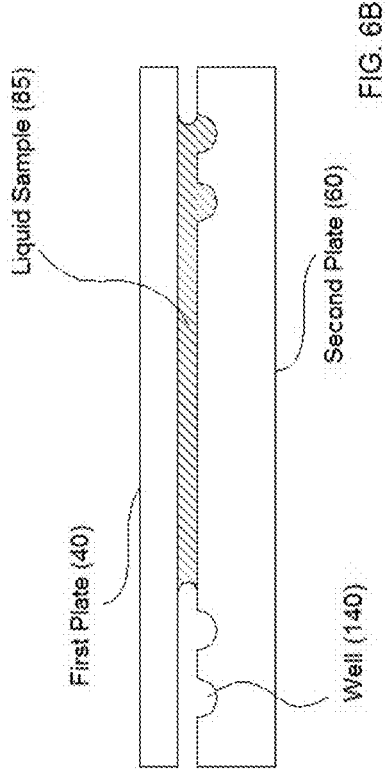
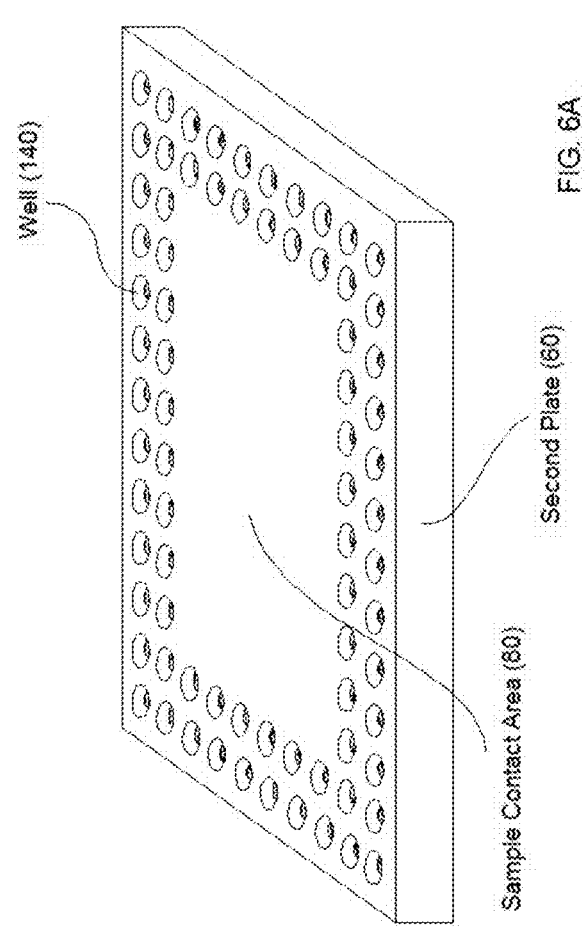

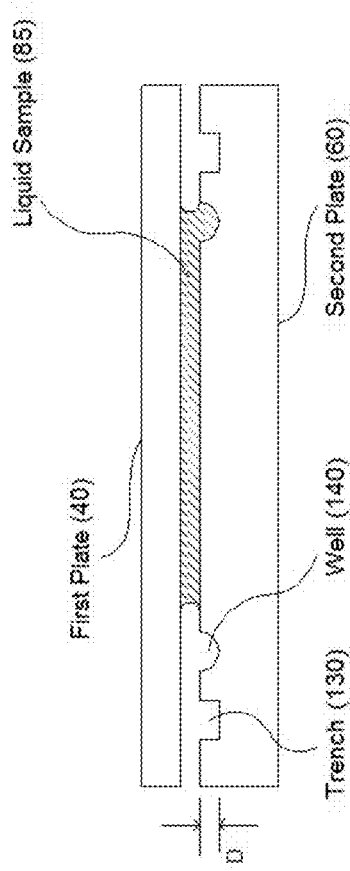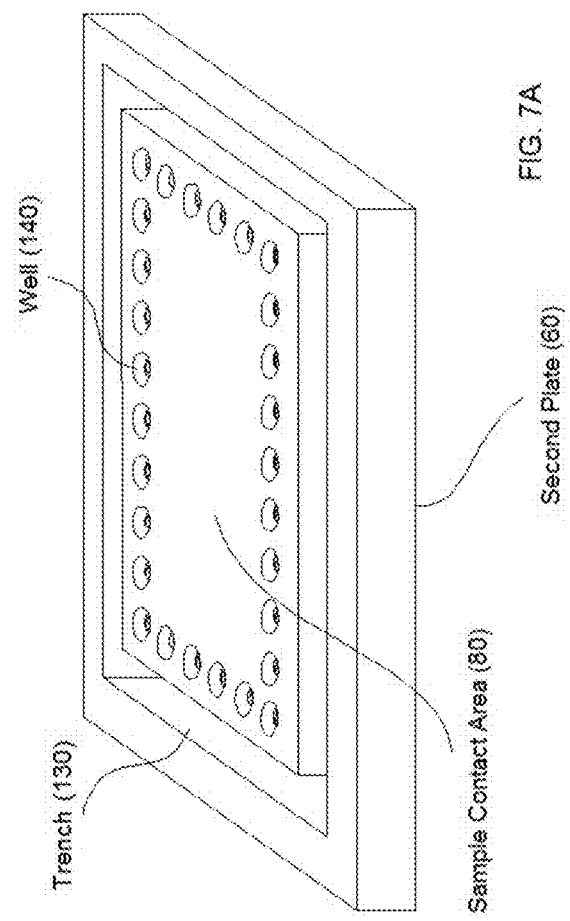

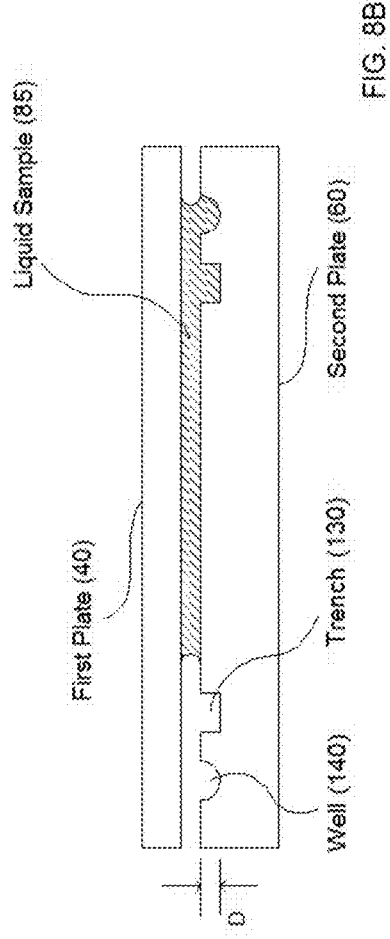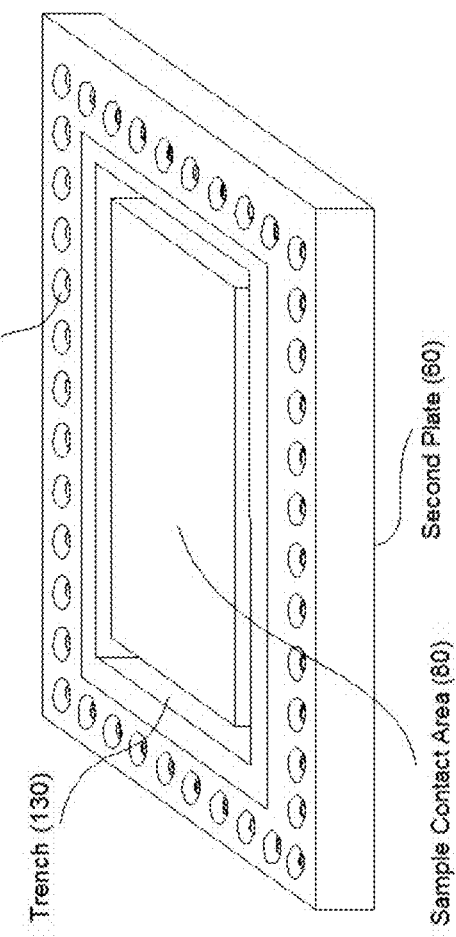

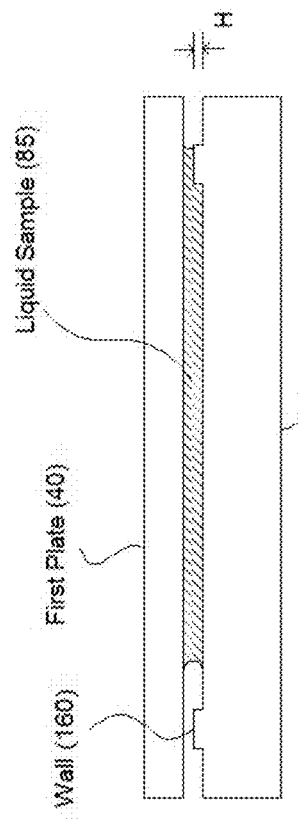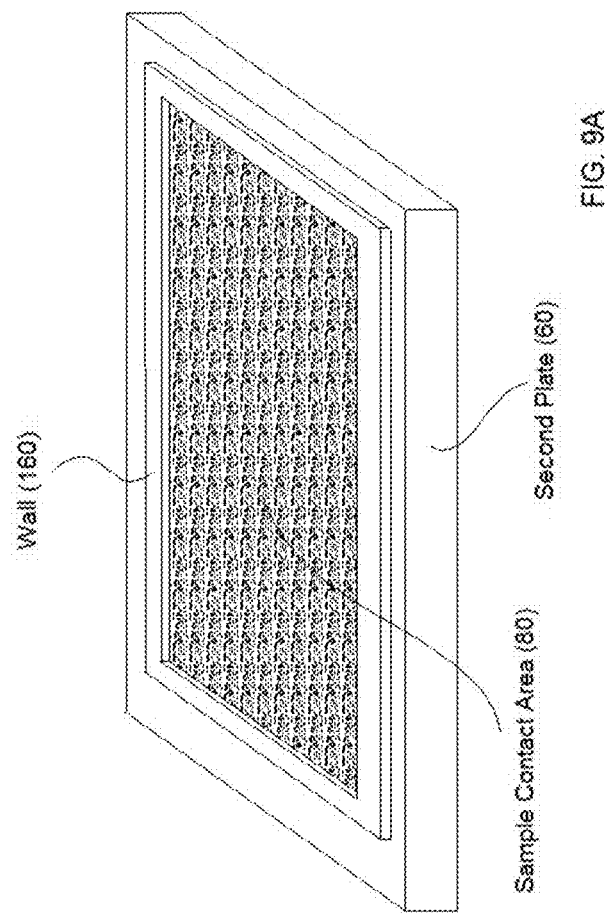

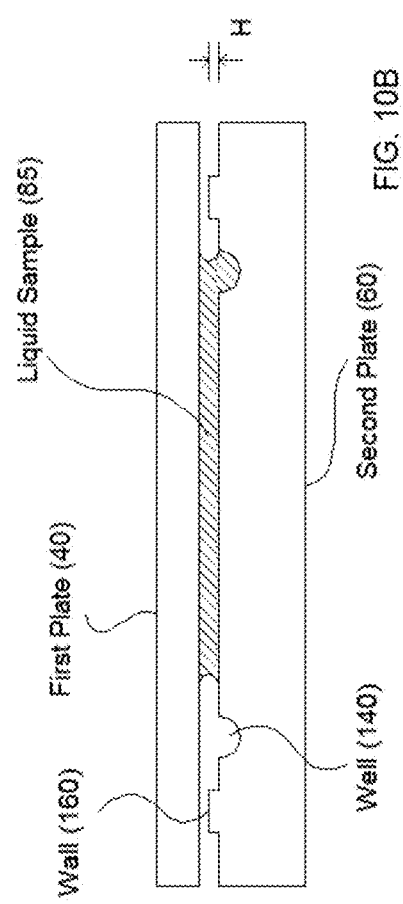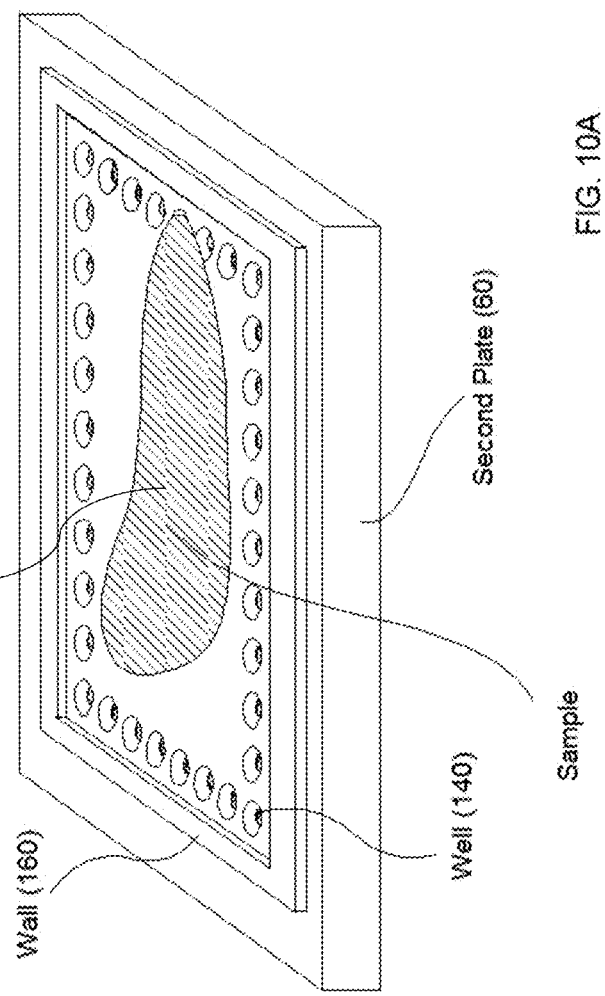

*Type A: 2 - 6*

Top view:

Cross-section view:

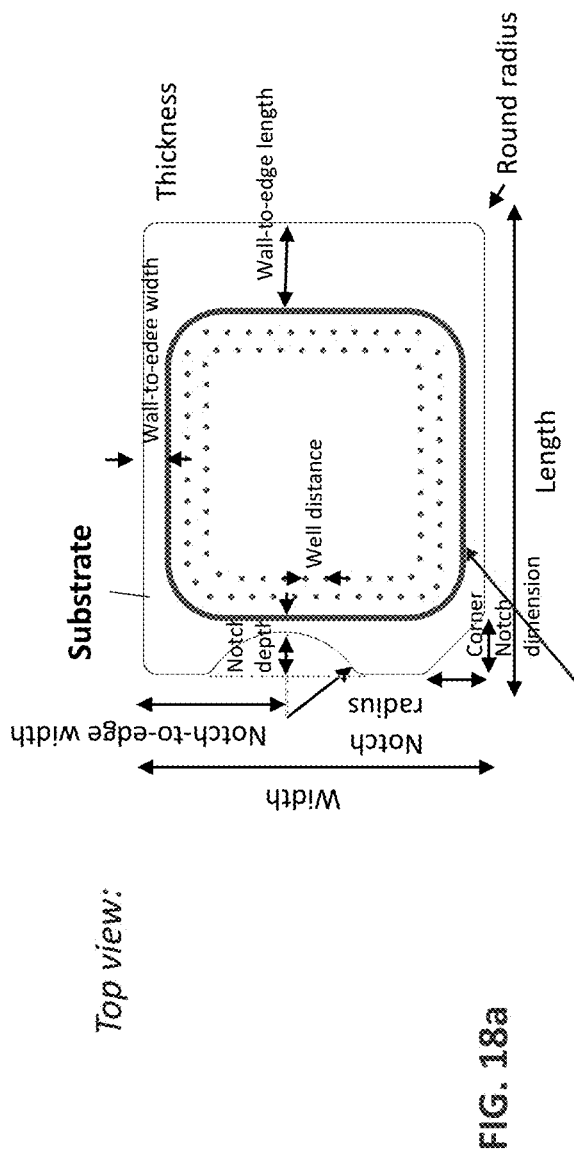
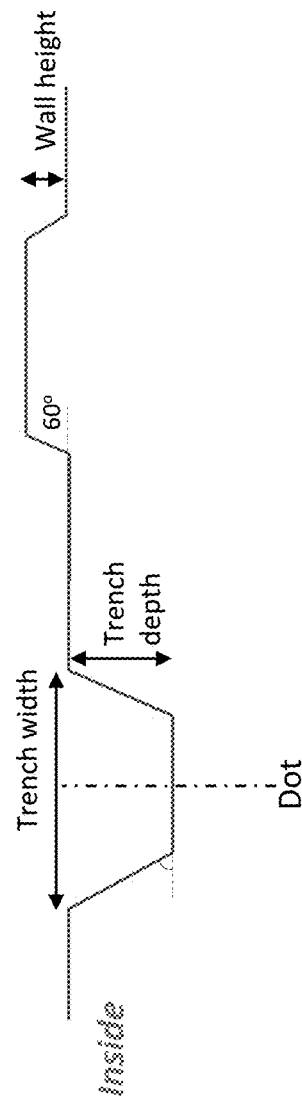
FIG. 18a
FIG. 18b

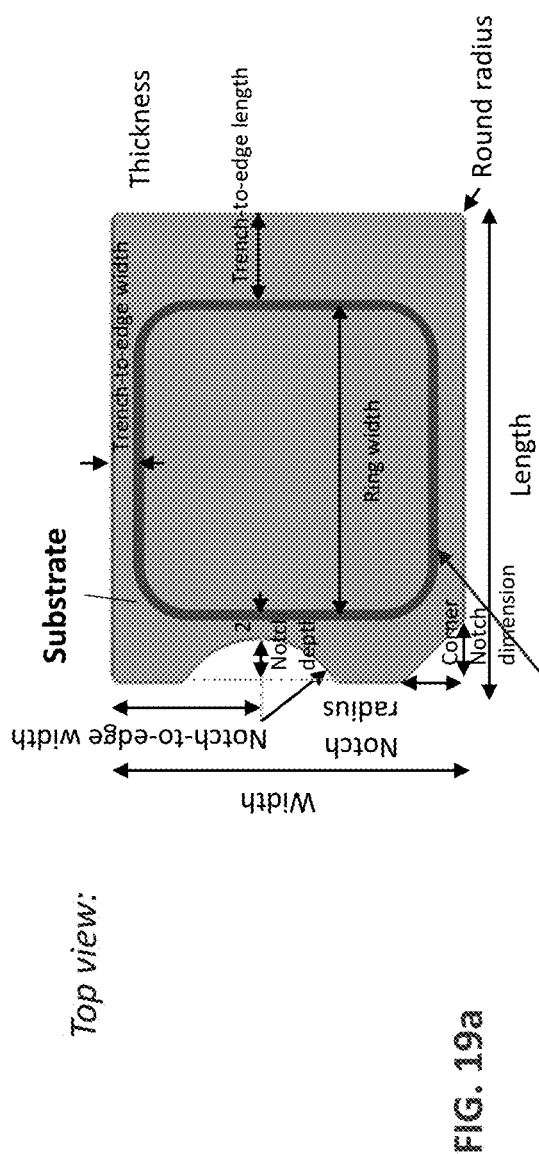
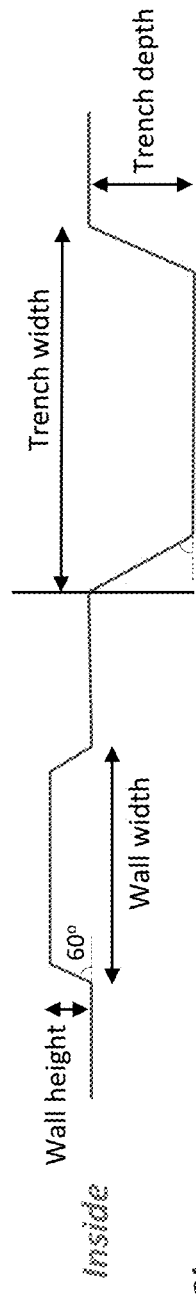
FIG. 19a
FIG. 19b

*Type E*

Top view:

Cross-section view:

CONTAINING A LIQUID SAMPLE

CROSS REFERENCING

This application is a National Stage entry (§ 371) application of International Application No. PCT/US18/55474, filed on Oct. 11, 2018, which claims the benefit of U.S. Provisional Patent Application No. 62/571,069, filed Oct. 11, 2017, the contents of which are relied upon and incorporated herein by reference in their entirety.

The entire disclosure of any publication or patent document mentioned herein is entirely incorporated by reference.

FIELD

Among other things, the present invention is related to devices and methods for containing a liquid sample between two plates.

BACKGROUND

In biological and chemical assays (e.g. diagnostic testing), there is a need to contain a sample in certain region of a sample holder and prevent the sample from flowing out of the sample holder. A flow out of a sample can cause contamination.

In previous assay method, a compressed open flow (COF) has been used in compressing a flowable sample (e.g. liquid) into a thin layer, which has many advantages over other methods. In previous COF, as shown in FIG. 1A-1D, two planar plates that are movable relative to each other are used, and a flowable sample is first deposited on one or both plates when the two plates are in an open configuration (FIG. 1B), followed by bring the two plates together to compress the sample between two plates; wherein the compression reduces a thickness of the sample and makes the sample flow into open spaces between the plates (FIG. 1C).

For a given spacing between the two plates at a closed configuration of the plates, and depending upon the total volume of the deposited sample, some of the sample can, during a compressing of the plates that brings the plates from an open configuration to a closed configuration, flow out from the edge 62 of the plates (so called "flowing-out") (FIG. 1D).

The sample flow-out causes two problems: (1) since the capillary force that holds the two plates together depends on the contact angle between the sample and the plate surface, a sample flowing-out will change the contact angle and can make the capillary force much smaller; and (2) the flowing-out sample can cause contamination.

In prior art COF, the two plates used have a planar surface, which raise two issues: (a) the maximum volume of the sample between the two plates without a sample flowing-out is approximately equal to the final spacing between the two plates multiplying the total area that the two plates overlap (so-called "Maximum Volume"), and (b) even the total volume of the sample is less that the Maximum volume in (a), a sample flowing-out can still occur, because of any or both of the two reasons: (i) the sample cannot be deposited at the center of the plate and (ii) the compression force and the sample flow cannot be even in directions. It is desirable and of significant practical importance that a sample flow-out does not occur. The present inventor addresses the flow-out issues and provides solutions to these problems.

SUMMARY OF THE INVENTION

A device for assaying a sample, comprising:
a first plate, a second plate, and a sample containment ring, wherein:
  i. the first plate and the second plate are movable relative to each other into different configurations, including an open configuration and a closed configuration;
  ii. each of the plates comprises an inner surface that has a sample contact area for depositing or contacting a sample;
  iii. the sample containment ring is on an inner surface of one or both of the plates and surrounds the sample contact areas; and
  iv. the sample containment ring comprises at least one sample containment feature; and
  v. the sample containment ring is configured to reduce or prevent the sample deposited on the plate from flowing out of an edge of the plates;
wherein the open configuration is a configuration in which the plates are partially or entirely separated apart, the average spacing between the sample contact areas of the plates is larger than 300 um, and the sample is deposited on the sample contact area of one or both plates; and
wherein the closed configuration is a configuration in which the average spacing between the sample contact areas of the plates is in a range of 0.1 µm to 250 µm.

A device for assaying a sample, comprising:
a first plate, a second plate, spacers, and a sample containment ring, wherein:
  i. the first and second plates are movable relative to each other into different configurations, including an open configuration and a closed configuration;
  ii. each of the plates comprises an inner surface that has a sample contact area for contacting a sample, and
  iii. the spacers are fixed on the inner surface of at least one plate, and at least one of the spacers is in the sample contact area;
  iv. the sample containment ring is on an inner surface of one or both of the plates and surrounds the sample contact area;
  v. the sample containment ring comprises at least one sample containment feature; and
  vi. the sample containment ring is configured to reduce or prevent the sample deposited on the plate from flowing out of an edge of the plates;
wherein, in the open configuration, the two plates are partially or entirely separated apart and the spacing between the sample contact areas of the plates is not regulated by the spacers, and the sample is deposited on a sample contact area of one or both of the plates; and
wherein, in the closed configuration, at least part of the sample deposited in the open configuration is confined between the surfaces of the sample contact areas, and the spacing between the sample contact areas of the plates is regulated by the spacers and is in the range of 10 nm to 250 µm.

The device of any prior embodiment, wherein the at least one sample containment feature is a well that that is configured to hold a portion of the sample.

The device of any prior embodiment, wherein the at least one sample containment feature is a trench that that is configured to hold a portion of the sample.

The device of any prior embodiment, wherein the at least one sample containment feature is a wall that impedes the sample flowing out from an edge of a plate.

The device of any prior embodiment, wherein the sample containment ring further comprises a plurality of wells that are configured to hold a portion of the sample.

The device of any prior embodiment, wherein the sample containment ring further comprises a plurality of trenches that are configured to hold a portion of the sample.

The device of any prior embodiment, wherein the sample containment ring further comprises a plurality of walls that impede the sample from flowing out from an edge of a plate.

The device of any prior embodiment, wherein the sample containment ring further comprises one or a plurality of wells, trenches, walls, or a combination of thereof.

The device of any prior embodiment, wherein in the closed configuration, at least one trench in the sample containment ring is an enclosed ring trench.

A method for assaying a sample, comprising:
(a) obtaining a device of any prior embodiment;
(b) obtaining a sample, which contains or is suspected of containing an analyte;
(c) depositing the sample on one or both of the sample contact areas when the plates are in the open configuration;
(d) pressing the plates into the closed configuration to compress at least part of the sample into a layer of uniform thickness; and
(e) analyzing a signal from the analyte in the sample.

The method of any prior embodiment, wherein the pressing is conducted with a human hand.

A system for assaying a sample, comprising:
(a) the device of any prior embodiment,
(b) an adaptor that is configured to accommodate the device and connect to a mobile apparatus, wherein:
the mobile apparatus comprises a camera,
the adaptor is configured to position the sample in a field of view (FOV) of the camera when the adaptor is connected to the mobile apparatus.

The system of any prior embodiment, wherein the mobile apparatus is configured to:
detect a signal related to an analyte in the sample; and
analyze the signal to determine the presence or concentration of the analyte in the sample.

The system of any prior embodiment, wherein the mobile apparatus is configured to capture images of the sample and measuring a signal related to an analyte in the images.

The device, method, or system of any prior embodiment, wherein the maximum storage volume is larger than the maximum sample contact-area volume.

The device, method, or system of any prior embodiment, wherein the maximum storage volume is larger than the volume of the sample that is deposited on the plate.

The device, method, or system of any prior embodiment, wherein the ratio of the maximum storage volume to the maximum sample contact-area volume is at least 0.1, at least 0.2, at least 0.5, at least 1, at least 2, at least 3, at least 4, at least 5, at least 6, at least 7, at least 8, at least 9, at least 10, at least 15, at least 20, or at least 30.

The device, method, or system of any prior embodiment, wherein the ratio of the maximum storage volume to the maximum sample contact-area volume is about 0.1, 0.2, 0.5, 1, 2, 3, 4, 5, 6, 7, 8, 9, 10, 15, 20, or 30, or in a range between any of the two values.

The device, method, or system of any prior embodiment, wherein the ratio of the maximum storage volume to the maximum sample contact-area volume is 1, 2, 5, 10, 20, or 30, or in a range between any of the two values.

The device, method, or system of any prior embodiment, wherein the maximum sample contact-area volume is 0.0001 µL, 0.005 µL, 0.01 µL, 0.05 µL, 0.1 µL, 0.5 µL, 1 µL, 5 µL, 10 µL, 50 µL, 100 µL, 500 µL, 1000 µL, or 5000 µL, or in a range between any of the two values.

The device, method, or system of any prior embodiment, wherein the maximum sample contact-area volume is less than 0.001 µL, 0.005 µL, 0.01 µL, 0.05 µL, 0.1 µL, 0.5 µL, 1 µL, 5 µL, 10 µL, or 50 µL.

The device, method, or system of any prior embodiment, wherein
the maximum sample contact-area volume is 0.0001 µL, 0.005 µL, 0.01 µL, 0.05 µL, 0.1 µL, 0.5 µL, 1 µL, 5 µL, 10 µL, 50 µL, 100 µL, 500 µL, 1000 µL, or 5000 µL, or in a range between any of the two values; and
the ratio of the maximum storage volume to the maximum sample contact-area volume is at least 0.1, at least 0.2, at least 0.5, at least 1, at least 2, at least 3, at least 4, at least 5, at least 6, at least 7, at least 8, at least 9, at least 10, at least 15, at least 20, or at least 30.

The device, method, or system of any prior embodiment, wherein
the maximum sample contact-area volume is less than 0.001 µL, 0.005 µL, 0.01 µL, 0.05 µL, 0.1 µL, 0.5 µL, 1 µL, 5 µL, 10 µL, or 50 µL; and
the ratio of the maximum storage volume to the maximum sample contact-area volume is about 0.1, 0.2, 0.5, 1, 2, 3, 4, 5, 6, 7, 8, 9, 10, 15, 20, or 30, or in a range between any of the two values.

The device, method, or system of any prior embodiment, wherein in a closed configuration of the plates, at least a portion of the sample containment ring on one plate is separated from the other plate by a gap.

The device, method, or system of any prior embodiment, wherein in a closed configuration of the plates, the two plates, that contact spacers, do not directly contact each other in the surface area that does not contact the spacers.

The device, method, or system of any prior embodiment, wherein the well comprises a plurality of wells that are organized as one row around the sample contact area.

The device, method, or system of any prior embodiment, wherein the well comprises a plurality of wells that are organized as two or more rows around the sample contact area.

The device, method, or system of any prior embodiment, wherein the trench comprises a continuous trench that encircles the sample contact area.

The device, method, or system of any prior embodiment, wherein the trench comprises a segmented trench.

The device, method, or system of any prior embodiment, wherein the trenches comprise a plurality of segmented trenches that encircle the sample contact area.

The device, method, or system of any prior embodiment, wherein the walls are positioned on one or both of the plates partially or entirely around the sample contact area to impede overflow of sample in the closed configuration.

The device, method, or system of any prior embodiment, wherein the sample containment ring comprises a plurality of wells and a stopping wall positioned on one or both of the plates partially or entirely around the sample contact area to block overflow of sample in the closed configuration.

The device, method, or system of any prior embodiment, wherein the sample containment ring comprises one or more trenches and a stopping wall positioned on one or both of the plates partially or entirely around the sample contact area to block overflow of sample in the closed configuration.

The device, method, or system of any prior embodiment, wherein the sample containment ring comprises:
- a trench continuously surrounding the sample contact area, the trench having a width of 0.001 um or less, 0.005 um or less, 0.01 um or less, 0.05 um or less, 0.1 um or less, 0.5 um or less, 1 um or less, 2 um or less, 5 um or less, 10 um or less, 20 um or less, 50 um or less, 100 um or less, 200 um or less, 500 um or less, or 1000 um or less, or in a range between any two of these values.

The device, method, or system of any prior embodiment, wherein the sample containment ring comprises:
- a trench continuously surrounding the sample contact area, the trench having a depth of 0.001 um or less, 0.005 um or less, 0.01 um or less, 0.05 um or less, 0.1 um or less, 0.5 um or less, 1 um or less, 2 um or less, 5 um or less, 10 um or less, 20 um or less, 50 um or less, 100 um or less, 200 um or less, 500 um or less, or 1000 um or less, or in a range between any two of these values.

The device, method, or system of any prior embodiment, wherein the sample containment ring comprises:
- a trench continuously surrounding the sample contact area, the trench having a total length of 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, 200 mm or less, 500 mm or less, or 1000 mm or less, or in a range between any two of these values.

The device, method, or system of any prior embodiment, wherein the sample containment ring comprises:
- a trench continuously surrounding the sample contact area, the trench having a width thereof between 0.2 μm to 200 μm and having a depth thereof ranged from 0.02 μm to 20 μm, and wherein a total length the trench is ranged from 20 mm to 40 mm.

The device, method, or system of any prior embodiment, wherein the sample containment ring comprises:
- a plurality of trenches each continuously surrounding the sample contact area, each of the trenches having a width of 0.001 um or less, 0.005 um or less, 0.01 um or less, 0.05 um or less, 0.1 um or less, 0.5 um or less, 1 um or less, 2 um or less, 5 um or less, 10 um or less, 20 um or less, 50 um or less, 100 um or less, 200 um or less, 500 um or less, or 1000 um or less, or in a range between any two of these values, a depth of 0.001 um or less, 0.005 um or less, 0.01 um or less, 0.05 um or less, 0.1 um or less, 0.5 um or less, 1 um or less, 2 um or less, 5 um or less, 10 um or less, 20 um or less, 50 um or less, 100 um or less, 200 um or less, 500 um or less, or 1000 um or less, or in a range between any two of these values, and wherein a total length the trenches is 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, 200 mm or less, 500 mm or less, or 1000 mm or less, or in a range between any two of these values.

The device, method, or system of any prior embodiment, wherein the sample containment ring further comprises:
- a plurality of trenches, each of the trenches having a width thereof ranged from 0.2 μm to 200 μm and having a depth thereof ranged from 0.02 μm to 20 μm, and wherein a total length of the trenches is ranged from 20 mm to 400 mm.

The device, method, or system of any prior embodiment, wherein the sample containment ring comprises:
- a wall continuously surrounding the sample contact area, the wall having a width of 0.001 um or less, 0.005 um or less, 0.01 um or less, 0.05 um or less, 0.1 um or less, 0.5 um or less, 1 um or less, 2 um or less, 5 um or less, 10 um or less, 20 um or less, 50 um or less, 100 um or less, 200 um or less, 500 um or less, or 1000 um or less, or in a range between any two of these values, a height of 0.001 um or less, 0.005 um or less, 0.01 um or less, 0.05 um or less, 0.1 um or less, 0.5 um or less, 1 um or less, 2 um or less, 5 um or less, 10 um or less, 20 um or less, 50 um or less, 100 um or less, 200 um or less, 500 um or less, or 1000 um or less, or in a range between any two of these values, and wherein a total length of the wall is 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, 200 mm or less, 500 mm or less, or 1000 mm or less, or in a range between any two of these values.

The device, method, or system of any prior embodiment, wherein the sample containment ring comprises:
- a wall continuously surrounding the sample contact area, the wall having a width thereof ranged from 0.2 μm to 200 μm and having a height thereof ranged from 0.02 μm to 20 μm, and wherein a total length of the wall is ranged from 20 mm to 400 mm.

The device, method, or system of any prior embodiment, wherein the sample containment ring comprises:
- a plurality of walls each continuously surrounding the sample contact area, each of the walls having a width of 0.001 um or less, 0.005 um or less, 0.01 um or less, 0.05 um or less, 0.1 um or less, 0.5 um or less, 1 um or less, 2 um or less, 5 um or less, 10 um or less, 20 um or less, 50 um or less, 100 um or less, 200 um or less, 500 um or less, or 1000 um or less, or in a range between any two of these values, a height of 0.001 um or less, 0.005 um or less, 0.01 um or less, 0.05 um or less, 0.1 um or less, 0.5 um or less, 1 um or less, 2 um or less, 5 um or less, 10 um or less, 20 um or less, 50 um or less, 100 um or less, 200 um or less, 500 um or less, or 1000 um or less, or in a range between any two of these values, and wherein a total length of the walls is 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, 200 mm or less, 500 mm or less, or 1000 mm or less, or in a range between any two of these values.

The device, method, or system of any prior embodiment, wherein the sample containment ring comprises:
- a plurality of walls, each of the walls having a width thereof ranged from 0.2 μm to 200 μm and having a height thereof ranged from 0.02 μm to 20 μm, and wherein a total length of the walls is ranged from 20 mm to 400 mm.

The device, method, or system of any prior embodiment, wherein the sample containment ring further comprises:
- a plurality of trenches, each of the trenches having a width thereof ranged from 0.2 μm to 200 μm and having a depth thereof ranged from 0.02 μm to 20 μm, and wherein a total length of the trenches is ranged from 20 mm to 400 mm.

The device, method, or system of any prior embodiment, wherein the sample containment ring comprises:
a plurality of wells each having a volume of less than 0.001 μL, less than 0.005 μL, less than 0.01 μL, less than 0.05 μL, less than 0.1 μL, less than 0.5 μL, less than 1 μL, less than 5 μL, less than 10 μL, less than 50 μL, less than 100 μL, less than 500 μL, less than 1000 μL, or less than 5000 μL, or in a range between any of the two values.

The device, method, or system of any prior embodiment, wherein the sample containment ring comprises:
a plurality of wells each having a volume thereof ranged from 0.001 μm3 to 1000 μm3.

The device, method, or system of any prior embodiment, wherein a shape of each well is one of a solid rectangular, a cylinder, a spheroidal cap, and a wedge.

The device, method, or system of any prior embodiment, wherein the sample containment ring further comprises:
a trench continuously surrounding the sample contact area, the trench having a width thereof ranged from 0.2 μm to 200 μm and having a depth thereof ranged from 0.02 μm to 20 μm, and wherein a total length the trench is ranged from 20 mm to 400 mm.

The device, method, or system of any prior embodiment, wherein the wells are arranged in a pattern that is surrounded by the trench.

The device, method, or system of any prior embodiment, wherein the wells are arranged in a pattern that surrounds the trench.

The device, method, or system of any prior embodiment, wherein the sample containment ring further comprises:
a plurality of trenches, each of the trenches having a width thereof ranged from 0.2 μm to 200 μm and having a depth thereof ranged from 0.02 μm to 20 μm, and wherein a total length of the trenches is ranged from 20 mm to 400 mm.

The device, method, or system of any prior embodiment, wherein the wells are arranged in a pattern that is surrounded by the trench.

The device, method, or system of any prior embodiment, wherein the wells are arranged in a pattern that surrounds the trench.

The device, method, or system of any prior embodiment, wherein a ratio of an overflow sample volume over the volume of a sample contact zone ranges from 2 to 20 and the overflow sample volume equals the total volume of the plurality of wells.

The device, method, or system of any prior embodiment, wherein a ratio of an overflow sample volume to the volume of a sample contact zone ranges from 4 to 10 and the overflow sample volume equals the total volume of the plurality of wells.

The device, method, or system of any prior embodiment, wherein the sample containment ring further comprises one or more trenches, and wherein a ratio of an overflow sample volume over the volume of a sample contact zone ranges from 2 to 20, and the overflow sample volume equals the total volume of the plurality of wells plus the total volume of the one or more trenches.

The device, method, or system of any prior embodiment, wherein the sample containment ring further comprises one or more trenches, and wherein a ratio of an overflow sample volume over the volume of a sample contact zone ranges from 4 to 10, and the overflow sample volume equals the total volume of the plurality of wells plus the total volume of the one or more trenches.

The device, method, or system of any prior embodiment, wherein the sample containment ring further comprises:
a wall continuously surrounding the sample contact area, the wall having a width thereof ranged from 0.2 μm to 200 μm and having a height thereof ranged from 0.02 μm to 20 μm, and wherein a total length of the wall is ranged from 20 mm to 400 mm.

The device, method, or system of any prior embodiment, wherein the wells are arranged in a pattern that is surrounded by the wall.

The device, method, or system of any prior embodiment, wherein the wells are arranged in a pattern that surrounds the wall.

The device, method, or system of any prior embodiment, wherein the sample containment ring further comprises:
a plurality of walls, each of the walls having a width thereof ranged from 0.2 μm to 200 μm and having a height thereof ranged from 0.02 μm to 20 μm, and wherein a total length of the walls is ranged from 20 mm to 400 mm.

The device, method, or system of any prior embodiment, wherein the wells are arranged in a pattern that is surrounded by the wall.

The device, method, or system of any prior embodiment, wherein the wells are arranged in a pattern that surrounds the wall.

The device, method, or system of any prior embodiment, wherein the sample is original, diluted, or processed forms of: bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, or exhaled breath condensate.

The device, method, or system of any prior embodiment, wherein the sample is original, diluted, or processed forms of blood.

The device, method, or system of any prior embodiment, wherein the sample comprises whole blood.

The device, method, or system of any prior embodiment, wherein the sample is a biological sample, a chemical sample, an environmental sample, or a foodstuff sample.

The device, method, or system of any prior embodiment, wherein the analyte is a biomarker, an environmental marker, or a foodstuff marker.

The device, method, or system of any prior embodiment, wherein the analyte is a biomarker indicative of the presence or severity of a disease or condition.

The device, method, or system of any prior embodiment, wherein the analyte is a cell, a protein, or a nucleic acid.

The device, method, or system of any prior embodiment, wherein the analyte comprises proteins, peptides, nucleic acids, synthetic compounds, inorganic compounds, organic compounds, bacteria, virus, cells, tissues, nanoparticles, and other molecules, compounds, mixtures and substances thereof.

The device, method, or system of any prior embodiment, wherein the sample holder comprises wells that configured to hold the sample.

The device, method, or system of any prior embodiment, wherein the sample holder comprises a first plate, and a second plate, and spacers.

The device, method, or system of any prior embodiment, wherein the sample holder comprises a first plate, a second plate, and spacers, wherein the spacers are configured to regulate a gap between the plates when the plates are pressed against each, compressing the sample into a thin layer.

The device, method, or system of any prior embodiment, wherein the sample holder comprises a first plate, a second plate, and spacers, and wherein:
  i. the plates are moveable relative to each other into different configurations, including an open configuration and a closed configuration;
  ii. in the open configuration: the two plates are separated apart, the spacing between the plates is not regulated by the spacers, and the sample is deposited on one or both of the plates; and
  iii. in the closed configuration, which is configured after the sample deposition in the open configuration: at least part of the sample is compressed by the two plates into a layer of highly uniform thickness and is substantially stagnant relative to the plates, wherein the uniform thickness of the layer is regulated by the plates and the spacers.

The device, method, or system of any prior embodiment, wherein the sample holder comprises a Q-card, which comprises a first plate, a second plate, and spacers, wherein the spacers are configured to regulate a gap between the plates when the plates are pressed against each, compressing the sample into a thin layer.

The device, method, or system of any prior embodiment, wherein
  i. the sample holder comprises a first plate, a second plate, and spacers, wherein the spacers have a uniform height and a constant inter-spacer distance; and
  ii. the sample is compressed by the sample holder into a thin layer with a uniform thickness that is regulated by the height of the spacers.

The device, method, or system of any prior embodiment, wherein the sample is compressed into a layer of uniform thickness that substantially equals uniform height of spacers that are fixed to one or both of the plates.

The device, method, or system of any prior embodiment, wherein the sample is compressed into a layer of uniform thickness that has a variation of less than 15%, 10%, 5%, 2%, 1%, or in a range between any of the two values.

The device, method, or system of any prior embodiment, wherein, in the closed configuration, the sample has a thickness of 500 nm or less, 1000 nm or less, 2 µm (micron) or less, 5 µm or less, 10 µm or less, 20 µm or less, 50 µm or less, 100 µm or less, 150 µm or less, 200 µm or less, 300 µm or less, 500 µm or less, 800 µm or less, 1 mm (millimeter) or less, 2 mm or less, 3 mm or less, 5 mm or less, 10 mm or less, or in a range between any two of these values.

The device, method, or system of any prior embodiment, wherein, in the closed configuration, the sample has a thickness in the range of 0.5-20 µm.

The device, method, or system of any prior embodiment, wherein, in the closed configuration, a gap between the first plate and the second plate is 500 nm or less, 1000 nm or less, 2 µm (micron) or less, 5 µm or less, 10 µm or less, 20 µm or less, 50 µm or less, 100 µm or less, 150 µm or less, 200 µm or less, 300 µm or less, 500 µm or less, 800 µm or less, 1 mm (millimeter) or less, 2 mm or less, 3 mm or less, 5 mm or less, 10 mm or less, or in a range between any two of these values.

The device, method, or system of any prior embodiment, wherein the sample holder comprises a first plate and a second plate, wherein each of the plate has a thickness of 500 nm or less, 1000 nm or less, 2 µm (micron) or less, 5 µm or less, 10 µm or less, 20 µm or less, 50 µm or less, 100 µm or less, 150 µm or less, 200 µm or less, 300 µm or less, 500 µm or less, 800 µm or less, 1 mm (millimeter) or less, 2 mm or less, 3 mm or less, 5 mm or less, 10 mm or less, or in a range between any two of these values.

The apparatus, kit, or method of any prior embodiment, wherein the imager comprises a camera.

The apparatus, kit, or method of any prior embodiment, wherein the imager is a part of the detector.

The apparatus, kit, or method of any prior embodiment, wherein the imager is the entirety of the detector.

The apparatus, kit, or method of any prior embodiment, wherein the imager is directed by the software to capture one or more images of the sample, identify the interference element regions and the interference element free regions, and digitally separate the interference element regions from the interference element free regions.

The apparatus, kit, or method of any prior embodiment, wherein the imager comprises a filter that is configured to filter signals from the sample.

The apparatus, kit, or method of any prior embodiment, wherein the imager comprises a light source that is configured to illuminate the sample.

The apparatus, kit, or method of any prior embodiment, wherein the detector is a mobile device.

The apparatus, kit, or method of any prior embodiment, wherein the detector is a smart phone.

The apparatus, kit, or method of any prior embodiment, wherein the detector is a smart phone and the imager is a camera as part of the smart phone.

The apparatus, kit, or method of any prior embodiment, wherein the detector comprises a display that is configured to show the presence or amount of the analyte.

The apparatus, kit, or method of any prior embodiment, wherein the detector is configured to transmit detection results to a third party.

The apparatus, kit, or method of any prior embodiment, wherein the software is stored in a storage unit, which is part of the detector.

The apparatus, kit, or method of any prior embodiment, wherein the software is configured to direct the detector to display the presence or amount of the analyte.

The apparatus, kit, or method of any prior embodiment, wherein the software is configured to direct the imager to calculate the combined signal of the analyte from the interference element free regions.

The apparatus, kit, or method of any prior embodiment, wherein the software is configured to direct the imager to disregard the signal of the analyte from the interference element regions.

The apparatus, kit, or method of any prior embodiment, wherein the software is configured to direct the imager to increase signal contrast of the signals from the interference element regions to the signals from the interference element free regions The apparatus, kit, or method of any prior embodiment, wherein the software is configured to direct the detector to calculate a ratio of the signal from the interference element regions to the interference element free regions.

The device, method, or system of any prior embodiment, wherein the mobile apparatus is a smart phone.

The device, method, or system of any prior embodiment, wherein the mobile apparatus comprises a set of instructions that, when executed, direct the apparatus to capture one or more images of the sample, The device, method, or system of any prior embodiment, wherein the mobile apparatus comprises a light source that is configured to illuminate the sample.

The device, method, or system of any prior embodiment, wherein the mobile apparatus comprises a display that is configured to show the presence or amount of the analyte.

The device, method, or system of any prior embodiment, wherein the mobile apparatus comprises a set of instructions that, when executed, direct the detector to display the presence or amount of the analyte.

The device, method, or system of any prior embodiment, wherein the mobile apparatus is configured to transmit detection results to a third party.

The device, method, or system of any prior embodiment, wherein the adaptor comprises a filter that is configured to filter signals from the sample.

The device, method, or system of any prior embodiment, wherein the adaptor comprises a card slot, into which the device can be inserted.

The device, method, or system of any prior embodiment, wherein the adaptor comprises a slider that facilitates the insertion of the device into the card slot.

The device, method, or system of any prior embodiment, wherein the adaptor comprises a holder frame that is configured to removably connect to the mobile apparatus.

The device, method, or system of any prior embodiment, wherein the adaptor comprises an optical box that comprises one or more optical components that are configured to enhance the signal from the sample.

The device, method or system of any prior embodiment, wherein the apparatus or method are used for detection of proteins, peptides, nucleic acids, synthetic compounds, inorganic compounds, organic compounds, bacteria, virus, cells, tissues, nanoparticles, and other molecules, compounds, mixtures and substances thereof.

The device, method or system of any prior embodiment, wherein the apparatus or method are used for diagnostics, management, or prevention of human diseases and conditions.

The device, method or system of any prior embodiment, wherein the apparatus or method are used for diagnostics, management, or prevention of veterinary diseases and conditions, or for diagnostics, management, or prevention of plant diseases and conditions.

The device, method or system of any prior embodiment, wherein the apparatus or method are used for environments testing and decontamination.

The device, method or system of any prior embodiment, wherein the apparatus or method are used for agricultural or veterinary applications.

The device, method or system of any prior embodiment, wherein the apparatus or method are used for food testing.

The device, method or system of any prior embodiment, wherein the apparatus or method are used for drug testing and prevention.

The device, method or system of any prior embodiment, wherein the apparatus or method are used for detecting or measuring an analyte in blood.

The device, method or system of any prior embodiment, wherein the apparatus or method are used for a colorimetric assay.

The device, method or system of any prior embodiment, wherein the apparatus or method are used for a fluorescence assay.

The device, method or system of any prior embodiment, wherein the signal related to the analyte is an electrical signal or an optical signal.

The device, method or system of any prior embodiment, wherein the signal related to the analyte is an optical signal that allows the imager to capture images of the interference element rich region and the interference element poor region.

The device, method or system of any prior embodiment, wherein the signal related to the analyte is from a colorimetric reaction.

The device, method or system of any prior embodiment, wherein the signal related to the analyte is produced by illuminating the sample with an illumination source.

The device, method or system of any prior embodiment, wherein the plates are movable relative to each.

The device, method or system of any prior embodiment, wherein the spacers are fixed on one or both of the plates and have a uniform height.

The device, method or system of any prior embodiment, wherein the first plate and second plate are configured to compress the sample into a layer of uniform thickness that substantially equals the height of the spacers.

The device, method or system of any prior embodiment, wherein the spacers have a uniform height of 1 mm or less, 500 um or less, 400 um or less, 300 um or less, 200 um or less, 175 um or less, 150 um or less, 125 um or less, 100 um or less, 75 um or less, 50 um or less, 40 um or less, 30 um or less, 20 um or less, 10 um or less, 5 um or less, 4 um or less, 3 um or less, 2 um or less, 1.8 um or less, 1.5 um or less, 1 um or less, 0.5 urn or less, 0.2 um or less, 0.1 um or less, 50 nm or less, 20 nm or less, 10 nm or less, or in a range between any of the two values.

The device, method or system of any prior embodiment, wherein the spacers have a uniform height in the range of 0.5-2 um, 0.5-3 um, 0.5-5 um, 0.5-10 um, 0.5-20 um, 0.5-30 um, or 0.5-50 um.

The device, method or system of any prior embodiment, wherein at least one of the plates has a thickness of 100 mm or less, 50 mm or less, 25 mm or less, 10 mm or less, 5 mm or less, 1 mm or less, 500 um or less, 400 um or less, 300 um or less, 200 um or less, 175 um or less, 150 um or less, 125 um or less, 100 um or less, 75 um or less, 50 urn or less, 40 um or less, 30 um or less, 20 um or less, 10 um or less, 5 um or less, 4 urn or less, 3 um or less, 2 um or less, 1.8 um or less, 1.5 um or less, 1 um or less, 0.5 urn or less, 0.2 um or less, or 0.1 um or less, or in a range between any of the two values.

The device, method or system of any prior embodiment, wherein at least one of the plates has a thickness in the range of 0.5 to 1.5 mm; around 1 mm; in the range of 0.15 to 0.2 mm; or around 0.175 mm.

The device, method or system of any prior embodiment, wherein at least one of the plates has a lateral area of 1 mm$^2$ or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, 500 cm$^2$ or less, 1000 cm$^2$ or less, 5000 cm$^2$ or less, 10,000 cm$^2$ or less, 10,000 cm$^2$ or less, or in a range between any two of these values The device, method or system of any prior embodiment, wherein at least one of the plates has a lateral area of in the range of 500 to 1000 mm$^2$; or around 750 mm$^2$ The device, method or system of any prior embodiment, wherein the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

The device, method or system of any prior embodiment, wherein the thickness of the flexible plate times the Young's modulus of the flexible plate is in the range 60 to 750 GPa-um.

The device, method or system of any prior embodiment, wherein for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ $um^3$/GPa.

The device, method or system of any prior embodiment, wherein one or both plates comprises a location marker, either on a surface of or inside the plate, that provide information of a location of the plate.

The device, method or system of any prior embodiment, wherein one or both plates comprises a scale marker, either on a surface of or inside the plate, that provide information of a lateral dimension of a structure of the sample or the plate.

The device, method or system of any prior embodiment, wherein one or both plates comprises an image marker, either on a surface of or inside the plate, that assists an imaging of the sample.

The device, method or system of any prior embodiment, wherein the inter-spacer distance is in the range of 7 um to 50 um.

The device, method or system of any prior embodiment, wherein the inter-spacer distance is in the range of 50 um to 120 um.

The device, method or system of any prior embodiment, wherein the inter-spacer distance is in the range of 120 um to 200 um.

The device, method or system of any prior embodiment, wherein the spacers are pillars with a cross-sectional shape selected from round, polygonal, circular, square, rectangular, oval, elliptical, or any combination of the same.

The device, method or system of any prior embodiment, wherein the spacers have a pillar shape and have a substantially flat top surface, wherein, for each spacer, the ratio of the lateral dimension of the spacer to its height is at least 1.

The device, method or system of any prior embodiment, wherein each spacer has the ratio of the lateral dimension of the spacer to its height is at least 1.

The device, method or system of any prior embodiment, wherein the minimum lateral dimension of spacer is less than or substantially equal to the minimum dimension of an analyte in the sample.

The device, method or system of any prior embodiment, wherein the minimum lateral dimension of spacer is in the range of 0.5 um to 100 um.

The device, method or system of any prior embodiment, wherein the minimum lateral dimension of spacer is in the range of 0.5 um to 10 um.

The device, method or system of any prior embodiment, wherein the spacers have a pillar shape, and the sidewall corners of the spacers have a round shape with a radius of curvature at least 1 um.

The device, method or system of any prior embodiment, wherein the spacers have a density of at least 100/$mm^2$.

The device, method or system of any prior embodiment, wherein the spacers have a density of at least 1000/$mm^2$.

The device, method or system of any prior embodiment, wherein at least one of the plates is transparent The device, method or system of any prior embodiment, wherein at least one of the plates is made from a flexible polymer.

The device, method or system of any prior embodiment, wherein, for a pressure that compresses the plates, the spacers are not compressible or, independently, only one of the plates is flexible.

The device, method or system of any prior embodiment, wherein the flexible plate has a thickness in the range of 10 um to 200 um.

The device, method or system of any prior embodiment, wherein the variation of sample thickness is less than 30%.

The device, method or system of any prior embodiment, wherein the variation of sample thickness is less than 10%.

The device, method or system of any prior embodiment, wherein the variation of sample thickness is less than 5%.

The device, method or system of any prior embodiment, wherein the first and second plates are connected and are configured to be changed from the open configuration to the closed configuration by folding the plates.

The device, method or system of any prior embodiment, wherein the first and second plates are connected by a hinge and are configured to be changed from the open configuration to the closed configuration by folding the plates along the hinge.

The device, method or system of any prior embodiment, wherein the first and second plates are connected by a hinge that is a separate material to the plates, and are configured to be changed from the open configuration to the closed configuration by folding the plates along the hinge.

The device, method or system of any prior embodiment, wherein the first and second plates are made in a single piece of material and are configured to be changed from the open configuration to the closed configuration by folding the plates.

The device, method or system of any prior embodiment, wherein the layer of uniform thickness sample is uniform over a lateral area that is at least 1 $mm^2$.

The device, method or system of any prior embodiment, wherein the spacers are fixed on a plate by directly embossing the plate or injection molding of the plate.

The device, method or system of any prior embodiment, wherein the materials of the plate and the spacers are selected from polystyrene, PMMA, PC, COC, COP, or a plastic.

The device, method or system of any prior embodiment, wherein, in a closed configuration of the plates, the average spacing between the sample contact areas of the plates is 10 nm, 100 nm, 500 nm, 1 um, 10 um, 30 um, 50 um, 100 um, 150 um, 200 um, 250 um, 300 um, 400 um, or a range between any two values thereof.

BRIEF DESCRIPTION OF THE DRAWINGS

A skilled artisan will understand that the drawings, described below, are for illustration purposes only. The drawings are not intended to limit the scope of the present teachings in any way. The figures do not intend to show the elements in strict proportion. For clarity purposes, some elements are enlarged when illustrated in the figures. The dimensions of the elements should be delineated from the descriptions herein provided and incorporated by reference. In the figures that present experimental data points, the lines that connect the data points are for guiding a viewing of the data only and have no other means.

FIG. 1A depicts the assaying device in a three-dimensional view when the assaying device is in an open configuration, in accordance with prior art.

FIG. 1B is a cross section of the assaying device of FIG. 1A in an open configuration, depicted in the x-z plane, in accordance with prior art.

FIG. 1C is a cross section of the assaying device of FIG. 1A in a close configuration, depicted in the x-z plane, in accordance with prior art.

FIG. 1D is a cross section of the assaying device of FIG. 1A, depicted in the x-y plane, in accordance with prior art.

FIG. 3A is a cross section of the assaying device of FIG. 2B in an open configuration, depicted in the x-z plane, in accordance with some embodiments of the present invention.

FIG. 3B is a cross section of the assaying device of FIG. 2B in a close configuration, depicted in the x-z plane, in accordance with some embodiments of the present invention.

FIG. 3C is a cross section of the assaying device of FIG. 2B, depicted in the x-y plane, in accordance with some embodiments of the present invention.

FIG. 4A depicts a three-dimensional view of a sample containment ring implemented with a trench in accordance with some embodiments of the present invention.

FIG. 4B shows part of a cross-section of an assaying device in FIG. 4A.

FIG. 5A depicts a three-dimensional view of a sample containment ring implemented with wells in one arrangement in accordance with some embodiments of the present invention.

FIG. 5B shows part of a cross-section of an assaying device in FIG. 5A.

FIG. 6A depicts a three-dimensional view of a sample containment ring implemented with wells in another arrangement, in accordance with some embodiments of the present invention.

FIG. 6B shows part of a cross-section of an assaying device in FIG. 6A.

FIG. 7A depicts a three-dimensional view of a sample containment ring implemented with a trench and wells in one arrangement, in accordance with some embodiments of the present invention.

FIG. 7B shows part of a cross-section of an assaying device in FIG. 7A.

FIG. 8A depicts a three-dimensional view of a sample containment ring implemented with a trench and wells in another arrangement, in accordance with some embodiments of the present invention.

FIG. 8B shows part of a cross-section of an assaying device in FIG. 8A.

FIG. 9A depicts a three-dimensional view of a sample containment ring implemented with a wall, in accordance with some embodiments of the present invention.

FIG. 9B shows part of a cross-section of an assaying device in FIG. 9A.

FIG. 10A depicts a three-dimensional view of a sample containment ring implemented with a wall and wells in one arrangement, in accordance with some embodiments of the present invention.

FIG. 10B shows part of a cross-section of an assaying device in FIG. 10A.

FIGS. 18A and 18B respectively show top and sectional views of a QMAX card that includes a sample containment ring according to some embodiments of the present invention.

FIGS. 19A and 19B respectively show top and sectional views of a QMAX card that includes a sample containment ring according to some embodiments of the present invention.

DETAILED DESCRIPTION OF EXEMPLARY EMBODIMENTS

Figure 2:
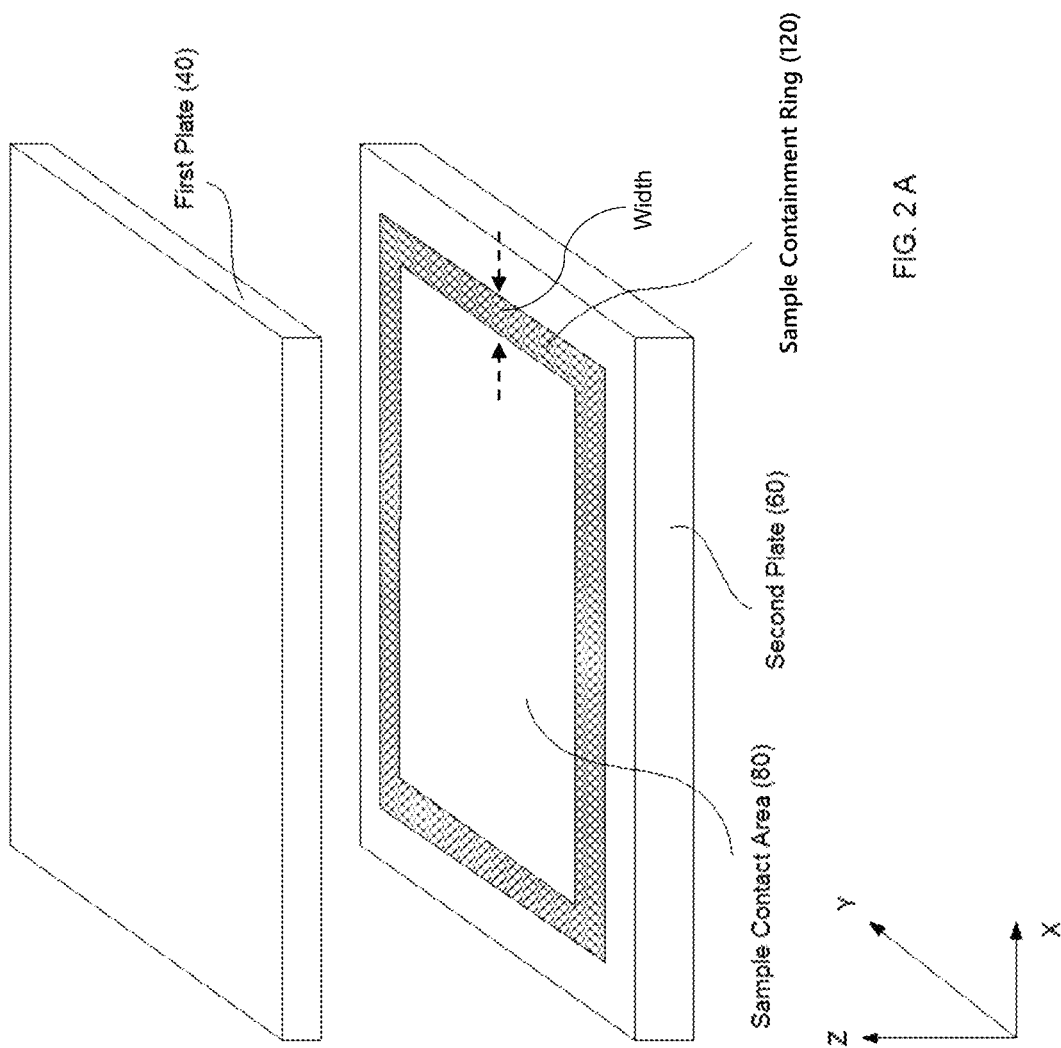
FIG. 2A depicts the assaying device in a three-dimensional view when the assaying device is in an open configuration, in accordance with some embodiments of the present invention.
FIG. 2B depicts the assaying device in a three-dimensional view when the sample containment ring is implemented as a trench, in accordance with some embodiments of the present invention.

The following detailed description illustrates some embodiments of the invention by way of example and not by way of limitation. If any, the section headings and any subtitles used herein are for facilitating reading purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Definitions

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present teachings, some exemplary methods and materials are now described.

The term "enclosed ring trench", "enclosed trench" and "a ring of trench" are interchangeable, and refer to a trench that encircles the sample contact area inside of the trench.

The term "enclosed wall" refers to a wall that encircles the sample contact area inside of the wall.

The term "sample contact area" refers to an area on an inner surface of either of the plates. Either of the sample contact areas contacts the sample when the sample is deposited on one or both of the plates. The sample contact areas of both plates are in contact with the sample when the plates are pressed against each other.

The term "sample deposition location" refers to a location where the sample is deposited when the plates are partially or entirely separated apart. In certain embodiments, the sample deposition location is in the sample contact area.

The terms "labeled analyte" and "bound label" are interchangeable. The phrase "labeled analyte" refers to an analyte that is detectably labeled with a light emitting label such that the analyte can be detected by assessing the presence of the label. A labeled analyte can be labeled directly (i.e., the analyte itself can be directly conjugated to a label, e.g., via a strong bond, e.g., a covalent or non-covalent bond), or a labeled analyte can be labeled indirectly (i.e., the analyte is bound by a secondary capture agent that is directly labeled).

The terms "unbound label" and "background" are interchangeable, with understanding that the signal of "unbound label" includes signals from other background that are not "unbound label".

The term "lateral area" refers to the area that is in parallel with the plate.

The term "analyte-concentration area" refers to an area of a surface where the area has a higher affinity to bind the labeled analyte/bound label (or to bind an analyte what later binds a label) than the rest area of the surface.

The term "lateral distance between two neighboring analyte concentration areas" or "IACD (inter analyte concentration-area distance)" refers to the distance between the average center of each analyte concentration area. For example, if each of the analyte concentration area has a circular shape in lateral shape, the IACD is the distance between the centers of the two circles. Another example, if each of the two analyte concentration areas is a vertical plane, then the IACD is the lateral distance between the two planes.

The term "diffusion parameter" or "DP" as used herein refers to a parameter that is equal to $\sqrt{Dt}$, wherein D is the diffusion constant of the analyte in the sample and the t is the intended assay time (i.e. the diffusion parameter is equal to the square-root of the diffusion constant of the analyte in the sample multiplying the intended assay time); wherein the intended assay time is a time parameter. For example, if the diffusion constant of the analyte in the sample is $1\times10^{-7}$ cm$^2$/s, the intended assay time is 60 sec, then the diffusion parameter is 24 μm (micron). Some of the common analyte diffusion constants are IgG in PBS: $3\times10^{-7}$ cm$^2$/s, IgG in blood: $1\times10^{-7}$ cm$^2$/s, and 20 bp DNA in blood: $4\times10^{-7}$ cm$^2$/s.

The term "bead" as used herein refers to a nano-scale or micro-scale three-dimensional object, regardless of its shape and material.

The term "specifically capture" means that a capture agent selectively bound an analyte that will be detected.

The terms "specific binding" and "selective binding" refer to the ability of a capture agent to preferentially bind to a particular target molecule that is present in a heterogeneous mixture of different target molecule. A specific or selective binding interaction will discriminate between desirable (e.g., active) and undesirable (e.g., inactive) target molecules in a sample, typically more than about 10 to 100-fold or more (e.g., more than about 1000- or 10,000-fold).

The terms "polypeptide", "peptide" and "protein" are used interchangeably herein to refer to polymers of amino acids of any length. The polymer can be linear or branched, it can comprise modified amino acids, and it can be interrupted by non-amino acids. The terms encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide", "nucleotide sequence", "nucleic acid", "nucleic acid molecule", "nucleic acid sequence" and "oligonucleotide" are used interchangeably, and can include plurals of each respectively depending on the context in which the terms are utilized. They refer to a polymeric form of nucleotides of any length, either deoxyribonucleotides (DNA) or ribonucleotides (RNA), or analogs thereof. Polynucleotides can have any three-dimensional structure, and can perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

The term "capture agent" as used herein, refers to a binding member, e.g. nucleic acid molecule, polypeptide molecule, or any other molecule or compound, that can specifically bind to its binding partner, e.g., a second nucleic acid molecule containing nucleotide sequences complementary to a first nucleic acid molecule, an antibody that specifically recognizes an antigen, an antigen specifically recognized by an antibody, a nucleic acid aptamer that can specifically bind to a target molecule, etc. A capture agent can concentrate the target molecule from a heterogeneous mixture of different molecules by specifically binding to the target molecule. Binding can be non-covalent or covalent. The affinity between a binding member and its binding partner to which it specifically binds when they are specifically bound to each other in a binding complex is characterized by a KD (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding, increased binding affinity being correlated with a lower KD.

The term "a secondary capture agent" which can be referred to as a "detection agent" refers a group of biomolecules or chemical compounds that have highly specific affinity to the antigen. The secondary capture agent can be strongly linked to an optical detectable label, e.g., enzyme, fluorescence label, or can itself be detected by another detection agent that is linked to an optical detectable label through bioconjugation (Hermanson, "Bioconjugate Techniques" Academic Press, 2nd Ed., 2008).

The term "capture agent-reactive group" refers to a moiety of chemical function in a molecule that is reactive with capture agents, i.e., can react with a moiety (e.g., a hydroxyl, sulfhydryl, carboxyl or amine group) in a capture agent to produce a stable strong, e.g., covalent bond.

The term "antibody," as used herein, is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (μ), delta (δ), gamma (γ), sigma (σ), and alpha (α) which encode the IgM, IgD, IgG, IgE, and IgA antibody "isotypes" or "classes" respectively. Antibody herein is meant to include full length antibodies and antibody fragments, and can refer to a natural antibody from any organism, an engineered antibody, or an antibody generated recombinantly for experimental, therapeutic, or other purposes. The term "antibody" includes full length antibodies, and antibody fragments, as are known in the art, such as Fab, Fab', F(ab') 2, Fv, scFv, or other antigen-binding subsequences of antibodies, either produced by the modification of whole antibodies or those synthesized de novo using recombinant DNA technologies.

The terms "antibody epitope," "epitope," and "antigen" are used interchangeably herein to refer to a biomolecule that is bound by an antibody. Antibody epitopes can include proteins, carbohydrates, nucleic acids, hormones, receptors, tumor markers, and the like, and mixtures thereof. An antibody epitope can be a group of antibody epitopes, such as a particular fraction of proteins eluted from a size exclusion chromatography column. Still further, an antibody epitope can be identified as a designated clone from an expression library or a random epitope library.

An "allergen," as used herein is a substance that elicits an allergic, inflammatory reaction in an individual when the individual is exposed to the substance, e.g., by skin contact, ingestion, inhalation, eye contact, etc. An allergen can include a group of substances that together elicit the allergic reaction. Allergens can be found in sources classified by the following groups: natural and artificial fibers (cotton, linen, wool, silk, teak, etc., wood, straw, and other dust); tree pollens (alder, birch, hazel, oak, poplar, palm, and others); weeds and flowers (ambrosia, artemisia, and others); grasses and corns (fescue, timothy grass, rye, wheat, corn, bluegrass, and others); drugs (antibiotics, antimicrobial drugs, analgetics and non-steroid anti-inflammatory drugs, anesthetics and muscle relaxants, hormones, and others); epidermal and animal allergens (epithelium of animals, feathers of birds, sera, and others); molds and yeasts (*Penicillium notation, Cladosporium* spp., *Aspergillus fumigatus, Mucor racemosus,* and others); insect venoms; preservatives (butylparaben, sorbic acid, benzoate, and others); semen (ejaculate); parasitic and mite allergens (ascarids, *Dermatophagoides pteronyssinus, Dermatophagoides farinae, Euroglyphus cannei,* and others); occupational and hobby allergens (coffee beans, formaldehyde, latex, chloramine, dyes, and others); food allergens (egg products, dairy products and cheeses, meat products, fish and seafood, soy products, mushrooms, flours and cereals, vegetables, melons and gourds, beans, herbs and spices, nuts, citrus and other fruits, berries, teas and herbs, nutritional supplements, and other products), etc.

The term "Hybridization" refers to a reaction in which one or more polynucleotides react to form a complex that is stabilized via hydrogen bonding between the bases of the nucleotide residues. The hydrogen bonding can occur by Watson-Crick base pairing, Hoogstein binding, or in any other sequence-specific manner. The complex can comprise two strands forming a duplex structure, three or more strands forming a multi-stranded complex, a single self-hybridizing strand, or any combination of these.

As is known to one skilled in the art, hybridization can be performed under conditions of various stringency. Suitable hybridization conditions are such that the recognition interaction between a capture sequence and a target nucleic acid is both sufficiently specific and sufficiently stable. Conditions that increase the stringency of a hybridization reaction are widely known and published in the art. See, for example, Green, et al., (2012), infra.

The term "protein" refers to a polymeric form of amino acids of any length, i.e. greater than 2 amino acids, greater than about 5 amino acids, greater than about 10 amino acids, greater than about 20 amino acids, greater than about 50 amino acids, greater than about 100 amino acids, greater than about 200 amino acids, greater than about 500 amino acids, greater than about 1000 amino acids, greater than about 2000 amino acids, usually not greater than about 10,000 amino acids, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. included by these terms are polypeptides that are post-translationally modified in a cell, e.g., glycosylated, cleaved, secreted, prenylated, carboxylated, phosphorylated, etc., and polypeptides with secondary or tertiary structure, and polypeptides that are strongly bound, e.g., covalently or non-covalently, to other moieties, e.g., other polypeptides, atoms, cofactors, etc.

The term "complementary" as used herein refers to a nucleotide sequence that base-pairs by hydrogen bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. Typically, "complementary" refers to a nucleotide sequence that is fully complementary to a target of interest such that every nucleotide in the sequence is complementary to every nucleotide in the target nucleic acid in the corresponding positions. When a nucleotide sequence is not fully complementary (100% complementary) to a non-target sequence but still can base pair to the non-target sequence due to complementarity of certain stretches of nucleotide sequence to the non-target sequence, percent complementarily can be calculated to assess the possibility of a non-specific (off-target) binding. In general, a complementary of 50% or less does not lead to non-specific binding. In addition, a complementary of 70% or less can not lead to non-specific binding under stringent hybridization conditions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 200 nucleotides and up to 300 nucleotides in length, or longer, e.g., up to 500 nucleotides in length or longer. Oligonucleotides can be synthetic and, in certain embodiments, are less than 300 nucleotides in length.

The term "attaching" as used herein refers to the strong, e.g., covalent or non-covalent, bond joining of one molecule to another.

The term "surface attached" as used herein refers to a molecule that is strongly attached to a surface.

The term "sample" as used herein relates to a material or mixture of materials containing one or more analytes or entity of interest. In particular embodiments, the sample can be obtained from a biological sample such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample can be obtained from a subject, e.g., a human, and it can be processed prior to use in the subject assay. For example, prior to analysis, the protein/nucleic acid can be extracted from a tissue sample prior to use, methods for which are known. In particular embodiments, the sample can be a clinical sample, e.g., a sample collected from a patient.

The term "analyte" refers to a molecule (e.g., a protein, peptides, DNA, RNA, nucleic acid, or other molecule), cells, tissues, viruses, and nanoparticles with different shapes.

The term "assaying" refers to testing a sample to detect the presence and/or abundance of an analyte.

As used herein, the terms "determining," "measuring," and "assessing," and "assaying" are used interchangeably and include both quantitative and qualitative determinations.

As used herein, the term "light-emitting label" refers to a label that can emit light when under an external excitation. This can be luminescence. Fluorescent labels (which include dye molecules or quantum dots), and luminescent labels (e.g., electro- or chemi-luminescent labels) are types of light-emitting label. The external excitation is light (photons) for fluorescence, electrical current for electroluminescence and chemical reaction for chemi-luminescence. An external excitation can be a combination of the above.

The terms "hybridizing" and "binding", with respect to nucleic acids, are used interchangeably.

The term "capture agent/analyte complex" is a complex that results from the specific binding of a capture agent with an analyte. A capture agent and an analyte for the capture agent will usually specifically bind to each other under "specific binding conditions" or "conditions suitable for specific binding", where such conditions are those conditions (in terms of salt concentration, pH, detergent, protein concentration, temperature, etc.) which allow for binding to occur between capture agents and analytes to bind in solution. Such conditions, particularly with respect to antibodies and their antigens and nucleic acid hybridization are well known in the art (see, e.g., Harlow and Lane (Antibodies: A Laboratory Manual Cold Spring Harbor Laboratory, Cold Spring Harbor, N.Y. (1989) and Ausubel, et al, Short Protocols in Molecular Biology, 5th ed., Wiley & Sons, 2002).

The term "specific binding conditions" and "conditions suitable for binding," as used herein with respect to binding of a capture agent to an analyte, e.g., a biomarker, a biomolecule, a synthetic organic compound, an inorganic compound, etc., refers to conditions that produce nucleic acid duplexes or, protein/protein (e.g., antibody/antigen) complexes, protein/compound complexes, aptamer/target complexes that contain pairs of molecules that specifically bind to one another, while, at the same time, disfavor to the formation of complexes between molecules that do not specifically bind to one another. Specific binding conditions are the summation or combination (totality) of both hybridization and wash conditions, and can include a wash and blocking steps, if necessary. For nucleic acid hybridization, specific binding conditions can be achieved by incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

For binding of an antibody to an antigen, specific binding conditions can be achieved by blocking a first plate containing antibodies in blocking solution (e.g., PBS with 3% BSA or non-fat milk), followed by incubation with a sample containing analytes in diluted blocking buffer. After this incubation, the first plate is washed in washing solution (e.g. PBS+TWEEN 20) and incubated with a secondary capture antibody (detection antibody, which recognizes a second site in the antigen). The secondary capture antibody can be conjugated with an optical detectable label, e.g., a fluorophore such as IRDye800CW, Alexa 790, Dylight 800. After another wash, the presence of the bound secondary capture antibody can be detected. One of skill in the art would be knowledgeable as to the parameters that can be modified to increase the signal detected and to reduce the background noise.

A subject can be a human or non-human animal. A subject can be a person performing the instant method, a patient, a customer in a testing center, etc.

An "analyte," as used herein is any substance that is suitable for testing in the present invention.

As used herein, a "diagnostic sample" refers to any biological sample that is a bodily byproduct, such as bodily fluids, that has been derived from a subject. The diagnostic sample can be obtained directly from the subject in the form of liquid, or can be derived from the subject by first placing the bodily byproduct in a solution, such as a buffer. Exemplary diagnostic samples include, but are not limited to, saliva, serum, blood, sputum, urine, sweat, lacrima, semen, feces, breath, biopsies, mucus, etc.

As used herein, an "environmental sample" refers to any sample that is obtained from the environment. An environmental sample can include liquid samples from a river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. Typically, samples that are not in liquid form are converted to liquid form before analyzing the sample with the present invention.

As used herein, a "foodstuff sample" refers to any sample that is suitable for animal consumption, e.g., human consumption. A foodstuff sample can include raw ingredients, cooked food, plant and animal sources of food, preprocessed food as well as partially or fully processed food, etc. Typically, samples that are not in liquid form are converted to liquid form before analyzing the sample with the present invention.

The term "diagnostic," as used herein, refers to the use of a method or an analyte for identifying, predicting the outcome of and/or predicting treatment response of a disease or condition of interest. A diagnosis can include predicting the likelihood of or a predisposition to having a disease or condition, estimating the severity of a disease or condition, determining the risk of progression in a disease or condition, assessing the clinical response to a treatment, and/or predicting the response to treatment.

A "biomarker," as used herein, is any molecule or compound that is found in a sample of interest and that is known to be diagnostic of or associated with the presence of or a predisposition to a disease or condition of interest in the subject from which the sample is derived. Biomarkers include, but are not limited to, polypeptides or a complex thereof (e.g., antigen, antibody), nucleic acids (e.g., DNA, miRNA, mRNA), drug metabolites, lipids, carbohydrates, hormones, vitamins, etc., that are known to be associated with a disease or condition of interest.

A "condition" as used herein with respect to diagnosing a health condition, refers to a physiological state of mind or body that is distinguishable from other physiological states. A health condition can not be diagnosed as a disease in some cases. Exemplary health conditions of interest include, but are not limited to, nutritional health; aging; exposure to environmental toxins, pesticides, herbicides, synthetic hormone analogs; pregnancy; menopause; andropause; sleep; stress; prediabetes; exercise; fatigue; chemical balance; etc. The term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least 10-8M. A biotin affinity agent can include a linker, e.g., -LC-biotin, -LC-LC-Biotin, -SLC-Biotin or -PEGn-Biotin where n is 3-12.

The term "streptavidin" refers to both streptavidin and avidin, as well as any variants thereof that bind to biotin with high affinity.

The term "marker", as used in describing a biological sample, refers to an analyte whose presence or abundance in a biological sample is correlated with a disease or condition.

The term "bond" includes covalent and non-covalent bonds, including hydrogen bonds, ionic bonds and bonds produced by van der Waal forces.

The term "amplify" refers to an increase in the magnitude of a signal, e.g., at least a 10-fold increase, at least a 100-fold increase at least a 1,000-fold increase, at least a 10,000-fold increase, or at least a 100,000-fold increase in a signal.

The term "entity" refers to, but not limited to proteins, peptides, DNA, RNA, nucleic acid, molecules (small or large), cells, tissues, viruses, nanoparticles with different shapes, that would bind to a "binding site". The entity includes the capture agent, detection agent, and blocking agent. The "entity" includes the "analyte", and the two terms are used interchangeably.

The term "binding site" refers to a location on a solid surface that can immobilize "entity" in a sample.

The term "entity partners" refers to, but not limited to proteins, peptides, DNA, RNA, nucleic acid, molecules (small or large), cells, tissues, viruses, nanoparticles with different shapes, that are on a "binding site" and would bind to the entity. The entity, include, but not limited to, capture agents, detection agents, secondary detection agents, or "capture agent/analyte complex".

The term "target analytes" or "target entity" refers to a particular analyte that will be specifically analyzed (i.e. detected), or a particular entity that will be specifically bound to the binding site.

The term "smart phone" or "mobile phone", which are used interchangeably, refers to the type of phones that has a camera and communication hardware and software that can take an image using the camera, manipulate the image taken by the camera, and communicate data to a remote place. In some embodiments, the Smart Phone has a flash light.

The term "light" refers to, unless specifically specified, an electromagnetic radiation with various wavelength.

The term "average linear dimension" of an area is defined as a length that equals to the area times 4 then divided by the perimeter of the area. For example, the area is a rectangle, that has width w, and length L, then the average of the linear dimension of the rectangle is $4*W*L/(2*(L+W))$ (where "*" means multiply and "/" means divide). By this definition, the average line dimension is, respectively, W for a square of a width W, and d for a circle with a diameter d. The area includes, but not limited to, the area of a binding site or a storage site.

The term "period" of periodic structure array refers to the distance from the center of a structure to the center of the nearest neighboring identical structure.

The term "storage site" refers to a site of an area on a plate, wherein the site contains reagents to be added into a sample, and the reagents are capable of being dissolving into the sample that is in contract with the reagents and diffusing in the sample.

The term "relevant" means that it is relevant to detection of analytes, quantification and/or control of analyte or entity in a sample or on a plate, or quantification or control of reagent to be added to a sample or a plate.

The term "hydrophilic", "wetting", or "wet" of a surface means that the contact angle of a sample on the surface is less than 90 degree.

The term "hydrophobic", "non-wetting", or "does not wet" of a surface means that the contact angle of a sample on the surface is equal to or larger than 90 degrees.

The term "variation" of a quantity refers to the difference between the actual value and the desired value or the average of the quantity. And the term "relative variation" of a quantity refers to the ratio of the variation to the desired value or the average of the quantity. For example, if the desired value of a quantity is Q and the actual value is $(Q+\Delta)$, then the $\Delta$ is the variation and the $\Delta/(Q+\Delta)$ is the relative variation. The term "relative sample thickness variation" refers to the ratio of the sample thickness variation to the average sample thickness.

The term "optical transparent" refers to a material that allows a transmission of an optical signal, wherein the term "optical signal" refers to, unless specified otherwise, the optical signal that is used to probe a property of the sample, the plate, the spacers, the scale-marks, any structures used, or any combinations of thereof.

The term "none-sample-volume" refers to, at a closed configuration of a CROF process, the volume between the plates that is occupied not by the sample but by other objects that are not the sample. The objects include, but not limited to, spacers, air bubbles, dusts, or any combinations of thereof. Often none-sample-volume(s) is mixed inside the sample.

The term "saturation incubation time" refers to the time needed for the binding between two types of molecules (e.g. capture agents and analytes) to reach an equilibrium. For a surface immobilization assay, the "saturation incubation time" refers the time needed for the binding between the target analyte (entity) in the sample and the binding site on plate surface reaches an equilibrium, namely, the time after which the average number of the target molecules (the entity) captured and immobilized by the binding site is statistically nearly constant.

In some cases, the "analyte" and "binding entity" and "entity" are interchangeable.

A "processor," "communication device," "mobile device," refer to computer systems that contain basic electronic elements (including one or more of a memory, input-output interface, central processing unit, instructions, network interface, power source, etc.) to perform computational tasks. The computer system can be a general purpose computer that contains instructions to perform a specific task, or can be a special-purpose computer.

A "site" or "location" as used in describing signal or data communication refers to the local area in which a device or subject resides. A site can refer to a room within a building structure, such as a hospital, or a smaller geographically defined area within a larger geographically defined area. A remote site or remote location, with reference to a first site that is remote from a second site, is a first site that is physically separated from the second site by distance and/or by physical obstruction. The remote site can be a first site that is in a separate room from the second site in a building structure, a first site that is in a different building structure from the second site, a first site that is in a different city from the second site, etc.

As used herein, "raw data" includes signals and direct read-outs from sensors, cameras, and other components and instruments which detect or measure properties or characteristics of a sample. For example, raw data includes voltage or current output from a sensor, detector, counter, camera, or other component or device; raw data includes digital or analog numerical output from a sensor, detector, counter, camera, or other component or device; and raw data can include digitized or filtered output from a sensor, detector, counter, camera, or other component or device. For example, raw data includes the output of a luminometer, which can include output in "relative light units" which are related to the number of photons detected by the luminometer. Raw data can include a JPEG, bitmap, or other image file produced by a camera. Raw data can include cell counts; light intensity (at a particular wavelength, or at or within a range of wavelengths); a rate of change of the output of a detector; a difference between similar measurements made at two times; a number of events detected; the number of events detected within a pre-set range or that meet a pre-set criterion; the minimum value measured within a time period, or within a field of view; the maximum value measured within a time period, or within a field of view; and other data. Where sufficient, raw data can be used without further processing or analysis. In other cases, raw data can be further processed or used for further analysis related to the sample, the subject, or for other purposes.

"Representative of a sample" as used in reference to an output signal or raw data that are representative of the sample, refers to the output signal or raw data reflecting a measured property of the sample or a portion thereof, e.g., reflecting the amount of analyte of interest present in the sample. For instance, the intensity of a fluorescence signal representative of a sample can be more intense in a fluorescently labeled sample that contains more analyte of interest than the intensity of a fluorescence signal representative of a fluorescently labeled sample that contains less analyte.

The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates.

The term "compressed regulated open flow" or "CROF" (or "self-calibrated compressed open flow" or "SCOF" or "SCCOF") refers to a particular type of COF, wherein the final thickness of a part or entire sample after the compression is "regulated" by spacers, wherein the spacers, that are placed between the two plates.

The term "the final thickness of a part or entire sample is regulated by spacers" in a CROF means that during a CROF, once a specific sample thickness is reached, the relative movement of the two plates and hence the change of sample thickness stop, wherein the specific thickness is determined by the spacer.

The practice of various embodiments of the present disclosure employs, unless otherwise indicated, conventional techniques of immunology, biochemistry, chemistry, molecular biology, microbiology, cell biology, genomics and recombinant DNA, which are within the skill of the art. See Green and Sambrook, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

In accordance with the present invention, an assay is provided. For purposes of this application, the term "assay" refers a measurement or a characterization of a properties of an analyte in a sample. The methods for the measurement or characterization in an assay, include, but not limited to electrical, optical, magnetic, chemical, or biological measurements.

In some embodiments, the assay includes the detection and/or measurement of DNA. For example, the assay can include a hybridization reaction that shows the presence and/or amount of the DNA. In some embodiments, the assay includes the detection and/or measurement of one or more proteins. For example, the assay can be an immunoassay that uses antibodies and/or antigens for the detections and/or measurement of one or more proteins in the sample. In some embodiments, the assay includes the detection and/or measurement of RNA. For example, the assay can include a hybridization reaction that shows the presence and/or amount of the RNA. In some embodiments, the assay includes the detection and/or measurement of cell proteins, such as but not limited to cell number, differentiation, proliferation, viability and/or cytotoxicity. In some embodiments, the assay includes detection and/or measurement of environmental or food contaminants. In some embodiments, the assay includes detection and/or measurement of surfactants, such as but not limited to detergents, wetting agents, emulsifiers, foaming agents, and dispersants. In some embodiments, the assay includes a reporter assay, an immunostaining, a nucleic acid microarray, an in situ hybridization, a polymerase chain reaction (PCR), a migration assay, a chemotaxis assay, a secretion assay, an apoptosis assay, a DNA laddering assay, a chemosensitivity assay, a tetramer assay, and a gentamicin protection assay.

In one aspect, the present invention provides devices and methods that can contain a flowable sample between the two plates in a COF without sample flowing-out, even if the volume of the sample and the location of sample deposition, as well as the compressing methods have a wide range of variation.

1. Principles and Certain Examples

One objective of the present invention provides the devices and methods that can contain a flowable sample in a region between the two plates in a COF without sample flowing-out, even if the volume of the sample and the location of sample deposition, as well as the compressing methods have a wide range of variation.

Figure 2B:
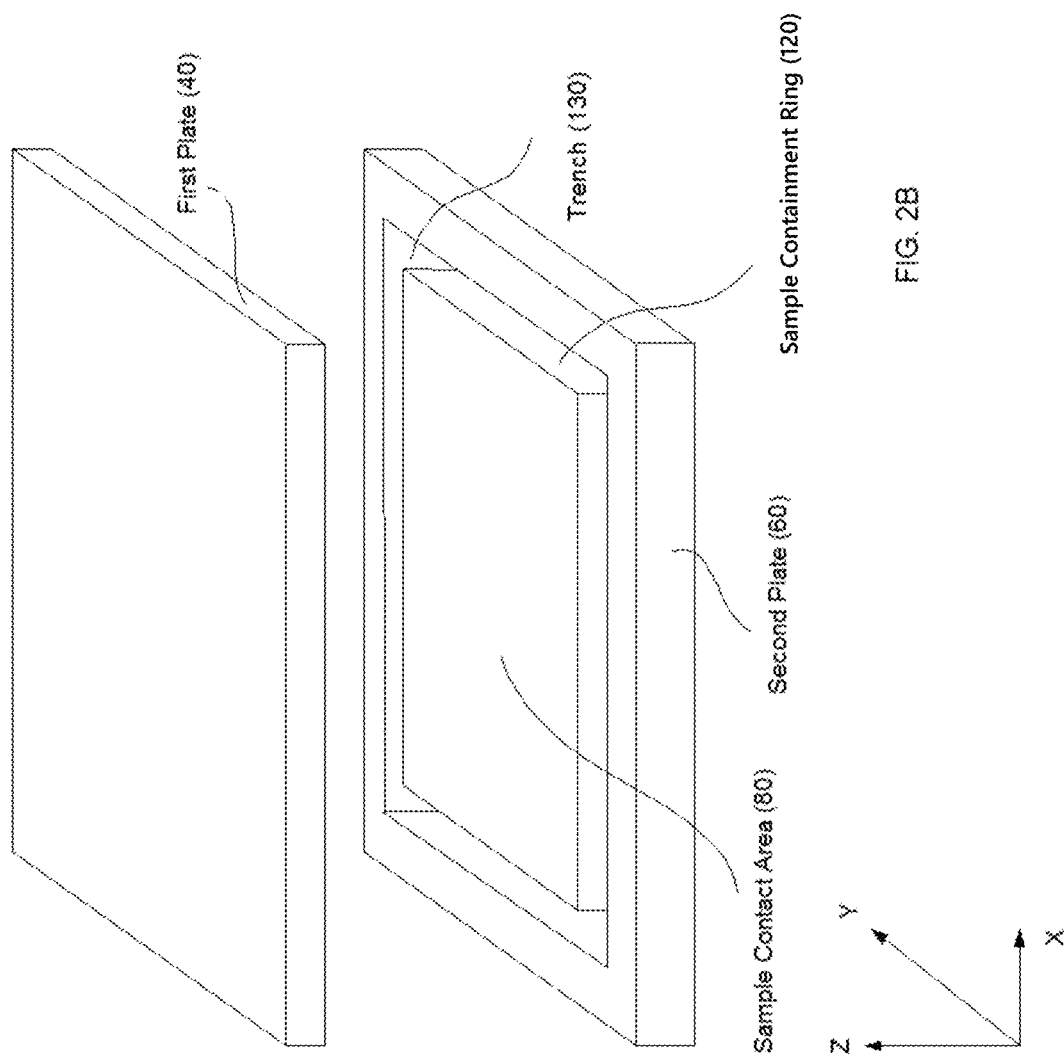

According to some embodiments of the present invention, one or both of the plates comprise a sample containment ring that surrounds the sample contact area (a sample is deposited in the sample deposition location which is a location in the sample contact area (e.g., as shown in FIG. 2B), wherein the sample containment ring is configured to contain a flowable sample between the two plates in a COF without a sample flowing-out, even if the volume of the sample and the location of sample deposition, as well as the compressing methods have a wide range of variation.

According to some embodiments of the present invention, the containment ring comprises at least a well on the inner surface of the plates. According to some embodiments of the present invention, the containment ring comprises a plurality of wells on the inner surface of the plates.

The term "well" means a depression below the surface of the plate, wherein the depression has a width and length (or a diameter) and a depth and is configured to accommodate an amount of a sample inside the depression, and wherein the ratio of the length to the width is between 1 to 2.

According to some embodiments of the present invention, the containment ring comprises at least a trench on the inner surface of the plates. According to some embodiments of the present invention, the containment ring comprises a plurality of trenches on the inner surface of the plates.

The term "trench" means a depression below the surface of the plate, wherein the depression has a width and length and a depth and is configured to accommodate an amount of a sample inside the depression, and wherein the ratio of the length to the width is larger than 2.

According to some embodiments of the present invention, the containment ring comprises a combination of any of the previous paragraphs.

According to some further embodiments of the present invention, the containment ring comprises at least a wall on the inner surface of the plates. According to some embodiments of the present invention, the containment ring comprises a plurality of walls on the inner surface of the plates.

The term "wall" means a protrusion above the surface of the plate, wherein the protrusion has a width and length, wherein the ratio of the length to the width is larger than 2.

According to some embodiments of the present invention, the device is a COF device. Specifically, the device, termed "COF device" includes a first plate and a second plate. The first plate and second plate are movable relative to each other into different configurations. One of the configurations is the open configuration and another configuration is the closed configuration.

Each of the plates in the COF device comprises an inner surface that has a sample contact area for contacting a liquid sample. The COF device includes a sample containment ring 120 that is on an inner surface of one of the plates and surrounds the sample contact area.

The sample containment ring comprises a structure that comprises a trench, a well, a plurality of trench, a plurality of wells, a wall, a plurality of wall, or a combination of thereof. The sample containment ring is configured to prevent the sample deposited on the sample contact area from, in an open flow caused by making the plates from an open configuration to a closed configuration, flowing out of an edge of the plates.

The wells and trenches provide space to store at least a part of the sample that is deposited on a sample contact area in an open configuration, but would, if there were no such wells or trenches, have flown out of an edge of a plate. The wall is configured to guide sample flow to reduce or prevent sample overflowing.

In addition to the containment of a flowable sample between the two plates in a COF device without sample flowing-out, a containment ring can accommodate certain size of dirt or decries to improve the tolerance to the presence of dirt or debris between the two plates.

In FIGS. 1A-1B and 2A-2C, the assaying device 100 comprises two substantially planar plates, a first plate 40 and a second plate 60. The first plate 40 and second plate 60 are movable relative to each other into different configurations, including an open configuration and a closed configuration. Each of the plates has an inner surface that has a sample contact area 80 for contacting a liquid sample.

As shown in FIGS. 1A-1B, the open configuration is a configuration, in which, the first plate 40 and second plate 60 are partially or entirely separated apart. In some embodiments, when the assaying device 100 is in the open configuration, the average spacing between the sample contact areas of the plates is larger than 300 μm.

As shown in FIG. 2B, the closed configuration is a configuration, in which, at least a portion of the first plate 40 and that of the second plate 60 are positioned substantially parallel to each other. In some embodiments, when the assaying device 100 is in the closed configuration, the average spacing between the sample contact areas of the plates can be in a range of 0.1 μm to 200 μm.

Figure 21:
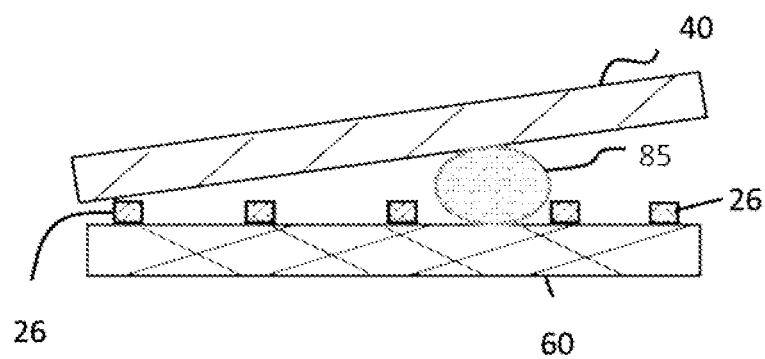
FIG. 21 schematically illustrates spacers disposed on one of the two plates of a QMAX card in accordance with an embodiment.

In some embodiments, spacers 26 are fixed on the inner surface of at least one of the two plates. For example, there are spacers 26 fixed on the inner surface of the first plate 40. In other embodiments, the spacers 26 are on the inner surface of the second plate 60, as shown in FIG. 21; or the spacers 26 are on the inner surfaces of both the first plate 40 and the second plate 60.

In some embodiments, spacers are used to control the spacing between the two plate in a closed configuration, where at least part of the sample is compressed by the two plates into a layer of highly uniform thickness, which is confined by the sample contact areas of the plates and is regulated by the plates and the spacers. In some embodiments, the spacers have a uniform height, which defines the gap between the two plates, and thus the uniform thickness of the sample layer. In some embodiments, the spacers have a constant inter-spacer distance (ISD).

In FIGS. 1A-1B and FIGS. 2A-2C, at least a part of one or both of the plates is at least partially transparent in at least one light wavelength for assaying an analyte in a liquid sample.

During a sample deposition, a sample is deposited inside of a sample deposition location which is inside of a sample contact area.

FIGS. 2A-2C depict a process of depositing a liquid (the term "liquid" and "flowable" are interchangeable) sample 85 between the two plates 40 and 60 of an assaying device 100. In FIG. 2A, a drop of liquid sample 85 is deposited on a sample deposition location on the second plate 60. In FIG. 2B, after the first plate 40 and second plate 60 are moved into a closed configuration, at least a part of the liquid sample 85 forms a uniform layer in the sample contact area 80. In some embodiments, if there are there are spacers on the inner surface of at least one plate. The thickness and the uniformity of the liquid sample 85 can be controlled by the spacers between the two plates 40 and 60.

Note that the sample containment ring, although it can have an amount of the sample, is not regarded as a sample contact area; and a sample contact area is the area that is inside of the sample containment ring.

The term "well size" refers to the lateral dimension of a well, which can be the diameter of the well or the length and width of the well.

The term "lateral dimension" refers to the dimension in the plane (i.e. surface) of the plate.

The term "depth" of the well or trench refers to the dimension normal to the plane (i.e. surface) of the plate.

The term "period" or "center-to-center distance" of a well or trench array refers to the lateral distance between the centers of two neighboring well or trench, respectively. The term "separation" of a well or trench array refers to the lateral distance between the closest edges of two neighboring well or trench, respectively.

1.1 Sample Containment Ring Having Trench

In some embodiments, a sample containment ring 120 of the assaying device 100 comprises at least one trench on an inner surface of the plate and surrounds the sample contact area.

FIGS. 1A-1B and FIGS. 2A-2C depict a sample containment ring 120 of the assaying device 100 comprising an enclosed trench 130 which encircles the sample contact area inside of the trench, in accordance with some embodiments. FIGS. 1A-1B depict the assaying device 100 in a three-dimensional view when the assaying device 100 is in an open configuration in accordance with some embodiments. Each of FIGS. 2A-2B is a cross section of the assaying device 100 of FIG. 1B, depicted in the x-z plane, in accordance with some embodiments. FIG. 2C is a cross section of the assaying device 100 of FIG. 1B, depicted in the x-y plane, in accordance with some embodiments.

In FIGS. 2A-2B and 4A-4B, the sample containment ring 120 is implemented as a trench 130 continuously surrounding the sample contact area 80. In the embodiment as shown in FIGS. 4A-4B, the trench having a width W and a depth D. The width W can be in a range of 0.2 μm to 200 μm, the depth D can be in a range of 0.02 μm to 20 μm, and a total length of the trench can be in a range of 20 mm to 400 mm. In the embodiment as shown in FIG. 2B and FIG. 4B, the trench 130 is continuous and surrounds the sample contact area 80. In other embodiments, the trench 130 does not have to be continuous, and there can be a gap between segments of a trench, and segments of a trench can be considered as multiple trenches. In certain embodiments, the sample contact area 80 can be surrounded by multiple trenches, each forming a ring that surrounds the sample contact area 80. In certain embodiments, multiple trenches form a ring that surrounds the sample contact area 80. The total length of the trenches can be in a range of 20 mm to 400 mm. In still other embodiments, there can be multiple trenches, and each of the multiple trenches can be continuously surrounding the sample contact area 80.

In certain embodiments, each of the trenches can have a width of 0.01 μm or less, 0.05 μm or less, 0.1 μm or less, 0.5 μm or less, 1 μm or less, 2 μm or less, 5 μm or less, 10 μm or less, 20 μm or less, 50 μm or less, 100 μm or less, 200 μm or less, 500 μm or less, 1,000 μm or less, 2 mm or less, or 5 mm or less, or in a range between any two of these values. In some preferred embodiments, each trench has a width in the range of 5 to 1,000 μm, 5 to 700 μm, or 10 to 600 μm.

In certain embodiments, each of the trenches can have a depth of 0.001 μm or less, 0.005 μm or less, 0.01 μm or less, 0.05 μm or less, 0.1 μm or less, 0.5 μm or less, 1 μm or less, 2 μm or less, 5 μm or less, 10 μm or less, 20 μm or less, 50 μm or less, 100 μm or less, 200 μm or less, 500 μm or less, or 1,000 μm or less, or in a range between any two of these values. In some preferred embodiments, each trench has a depth in the range of 0.1 to 700 μm, 1 to 500 μm, or 1 to 300 μm.

In certain embodiments, a total length of the trenches can be 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, 200 mm or less, 500 mm or less, or 1000 mm or less, or in a range between any two of these values.

1.2. Sample Containment Ring Having Wells

Stored Sample Backflow

While the trench 130 can reduce a liquid sample from flowing out of an edge of the second plate 60, however, it has some limitations. One key limitation of a trench is the stored sample backflow.

The term "stored sample backflow" refers to the fact that if a trench or well is not completely filled with a sample, the sample stored inside the trench or well can, due the capillary forces between the planar sections of the plates, can suck backflow out of the trench or well. This is because that the capillary forces between the planar sections of the plates are stronger than that inside of trench.

For example, if only a segment 134 of the trench 130 is filled up, the liquid sample can leak out to the peripheral areas surrounding the trench 130. The liquid sample in the segment 134 of the trench 130 can be sucked into the gap 128 between the two plates due to the capillary action caused by the surface tension. The magnitude of the force exerting on the liquid caused by the surface tension at a particular location is directly proportional to the curvature of the liquid surface at that particular location. The larger the curvature, the larger the force exerting on the liquid. The curvature of the liquid at the gap 128 between the two plates (in a peripheral area surrounding the trench 130) is larger than the curvature of the liquid at each end of the trench segment 134. Therefore, the force $F_g$ exerting on the liquid at the gap 128 between the two plates is large than the force $F_t$ exerting on the liquid at each end of the trench segment 134. Consequently, the liquid sample in the trench segment 134 is sucked into the gap 128 between the two plates. The liquid sample sucked into the gap 128 can flow out of an edge of the second plate 60, which defeats the purpose of the containment ring 120.

One way to reduce a stored sample backflow is to use a well or trench with a small sample storage volume and use multiple wells and/or trenches to make a desired total storage sample volume.

The term "sample storage volume" of a well or trench refers to the total volume of a sample that can be stored in the well or the trench.

1.2.1 Well and One Row of Wells

In some embodiments, the sample containment ring comprises at least one well. In some embodiments, the sample containment ring comprises a plurality of wells. There are a number of ways to arrange the plurality of the wells.

One Row of Wells. FIG. 5A depicts a three-dimensional view of a sample containment ring 120 that comprises a row of wells, in accordance with some embodiments. FIG. 5B shows part of a cross-section of an assaying device 100 in FIG. 5A. In FIGS. 5A-5B, the sample containment ring 120 with a row of wells 140 surrounding the sample contact area 80.

The wells 140 in FIG. 5A are lined up near the edges of the plate 60 to confine the liquid sample 85 in the sample contact area 80.

When the plates of the assaying device 100 are changed from an open configuration to a closed configuration, the wells 140 can have the function to prevent or reduce the liquid sample 85 from flowing out of an edge of the plate 60.

The shape of a well in FIGS. 5A-5B can be a spheroidal cap, a solid rectangular, a cylinder, a wedge, or any other three-dimensional shapes that can be fabricated on the plate 60.

Such well can have a volume in the range of 0.0001 µL to 5000 µL. In certain embodiments, the total volume of such overflow reducing well can be at least 0.001 µL, 0.005 µL, 0.01 µL, 0.05 µL, 0.1 µL, 0.5 µL, 1 µL, 5 µL, 10 µL, 50 µL, 100 µL, 500 µL, 1000 µL, or 5000 µL, or in a range between any of the two values.

1.2.2 Two Rows of Wells

In some embodiments, the performance of the containment ring 120 can be improved by using more than one row of wells in a sample containment ring.

FIG. 6A depicts a three-dimensional view of a sample confinement ring implemented with wells in another arrangement in accordance with some embodiments. FIG. 6B shows part of a cross-section of an assaying device 100 in FIG. 6A. In FIGS. 6A-6B, the sample confinement ring 120 is implemented as wells 140 surrounding the sample contact area 80. The wells 140 FIG. 6A are lined up near the edges of the plate 60 to confine the liquid sample 85 in the sample contact area 80. In FIG. 6B, there are either two columns of wells or two rows of wells lined up near each edge of the plate 60. When the plates of the assaying device 100 are changed from an open configuration to a closed configuration, the wells 140 can have the function to prevent the liquid sample 85 from flowing out of an edge of the plate 60. The shape of a well in FIGS. 6A-6B can be a spheroidal cap, a solid rectangular, a cylinder, a wedge, or any other three-dimensional shapes that can be fabricated on the plate 60. Such well can have a volume in the range of 0.001 $\mu m^3$ to 1000 $\mu m^3$. Depend on the implementations or designs, the total volume of such overflow preventing well can be at least 0.001 µL, 0.005 µL, 0.01 µL, 0.05 µL, 0.1 µL, 0.5 µL, 1 µL, 5 µL, 10 µL, 50 µL, 100 µL, 500 µL, 1000 µL, or 5000 µL, or in a range between any of the two values.

If the total volume of the wells 140 is defined as the overflow sample volume, the ratio of the overflow sample volume to the sample volume allowed by the sample contact area in the closed configuration can be in a range of 0.5 to 10. Depend on the implementations or designs, the total volume of the overflow preventing well can be at least 0.5, 1, 2, 3, 4, 5, 6, 7, 8, 9, or 10 times of the sample volume allowed by the sample contact area in the closed configuration.

1.2.3 Multiple Rows of Wells

In some embodiments, the number of rows of the well can be more two. In some embodiments, the well size and well spacing in different rows are different. In some embodiments, the well size and well spacing with a row are different.

1.2.4 Well Parameters

For the embodiments in which the sample containment ring comprises wells, as indicated above, the wells can have the same or different parameters. When there are multiple wells, the wells can be periodic or aperiodic.

In some embodiments, the width (i.e. diameter) of a well can be about 0.1 µm, 0.2 µm, 0.5 µm, 1 µm, 2 µm, 5 µm, 10 µm, 20 µm, 50 µm, 100 µm, 200 µm, 500 µm, 1 mm, 2 mm, or 5 mm, or in a range between any of the two values. In some preferred embodiments, the width of the well is in the range of 5 µm to 1,000 µm, 5 µm to 700 µm, or 10 µm to 600 µm.

In some embodiments, the depth of a well can be about 0.1 µm, 0.2 µm, 0.5 µm, 1 µm, 2 µm, 5 µm, 10 µm, 20 µm, 50 µm, 100 µm, 200 µm, 500 µm, 1 mm, 2 mm, or 5 mm, or in a range between any of the two values. In some preferred embodiments, the depth of the well is in the range of 0.1 µm to 700 µm, 1 µm to 500 µm, or 1 µm to 300 µm.

In some embodiments, the period (i.e. center to center distance between neighboring wells) of a plurality of wells can be about 0.1 µm, 0.2 µm, 0.5 µm, 1 µm, 2 µm, 5 µm, 10 µm, 20 µm, 50 µm, 100 µm, 200 µm, 500 µm, 1 mm, 2 mm, or 5 mm, or in a range between any of the two values. In some preferred embodiments, the period of the plurality of wells is in the range of 10 µm to 5 mm, 10 µm to 500 µm, 10 µm to 1 mm, or 30 µm to 700 µm.

In some embodiments that comprise multiple rows of wells, the distance between the neighboring rows can be about 0.1 μm, 0.2 μm, 0.5 μm, 1 μm, 2 μm, 5 μm, 10 μm, 20 μm, 50 μm, 100 μm, 200 μm, 500 μm, 1 mm, 2 mm, or 5 mm, or in a range between any of the two values. In some preferred embodiments, the distance between the neighboring rows is in the range of 10 μm to 5 mm, 10 μm to 500 μm, 10 μm to 1 mm, or 30 μm to 700 μm.

1.3. Sample Containment Ring Having Wells and Trench

FIG. 7A depicts a three-dimensional view of a sample containment ring 120 implemented with a trench and wells in one arrangement in accordance with some embodiments. FIG. 7B shows part of a cross-section of an assaying device 100 in FIG. 7A. FIG. 8A depicts a three-dimensional view of a sample containment ring 120 implemented with a trench and wells in another arrangement in accordance with some embodiments. FIG. 8B shows part of a cross-section of an assaying device 100 in FIG. 8A. In FIGS. 7A-7B and FIGS. 8A-8B, the sample containment ring 120 surrounding the sample contact area 80 comprises both a trench 130 and wells 140 on the inner surface of the plate 60. In FIG. 7A, the wells 140 are arranged in a pattern that is surrounded by the trench 130. In FIG. 8A, the wells 140 are arranged in a pattern that surrounds the trench 130. In FIG. 7A and FIG. 8A, both the trench 130 and the formed pattern of the wells 140 surround the sample contact area 80. If the total volume of the wells 140 plus the total volume of the trench 130 is defined as the overflow sample volume, the ratio of the overflow sample volume to the sample volume allowed by the sample contact area in the closed configuration can be in a range of 0.5 to 20 according to some embodiments.

1.4 Sample Containment Ring Having Wall

Another method of improving the performance of the containment ring 120 is add a wall 160, such as a wedge, near the trench 130, as shown in FIGS. 4A-4B. In the embodiments as shown in FIGS. 4A-4B, the wall 160 is implemented in such a way to leave a gap 147 between the first plate 40 and an upper edge of the wall 160. The gap 127 be in a range of 0.2 μm to 200 μm. The embodiments of separating the first plate 40 from the wall 160 with a gap 127 can have the advantage of increasing the assaying device 100's tolerance to the presence of dirt or debris between the two plates of the assaying device 100.

One of the functions of the wall 160 is to prevent the liquid sample 85 from flowing out of the edge; therefore, reducing the amount of the liquid flowing into the trench 130. Such function reduces the chance of some segments of the trench being filled up with liquid sample which can get sucked into the gap 128 between the two plates (in a peripheral area surrounding the trench 130)

The wall s can be implemented on the inner surface of one of the plates in an assaying device 100 as the containment ring 120, along with the trench as shown in FIGS. 4A-4B or independent of the trench as shown in FIGS. 9A-9B. In the embodiment as shown in FIGS. 9A-9B, the wall having a width W and a height H. The width W can be in a range of 0.2 μm to 200 μm, the height H can be in a range of 0.02 μm to 20 μm, and a total length of the wall can be in a range of 20 mm to 400 mm.

In certain embodiments, the wall can have a width of 0.001 μm or less, 0.005 μm or less, 0.01 μm or less, 0.05 μm or less, 0.1 μm or less, 0.5 μm or less, 1 μm or less, 2 μm or less, 5 μm or less, 10 μm or less, 20 μm or less, 50 μm or less, 100 μm or less, 200 μm or less, 500 μm or less, or 1000 μm or less, or in a range between any two of these values. In certain embodiments, the wall can have height of 0.001 μm or less, 0.005 μm or less, 0.01 μm or less, 0.05 μm or less, 0.1 μm or less, 0.5 μm or less, 1 μm or less, 2 μm or less, 5 μm or less, 10 μm or less, 20 μm or less, 50 μm or less, 100 μm or less, 200 μm or less, 500 μm or less, or 1000 μm or less, or in a range between any two of these values. In certain embodiments, a total length of the wall can be 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, 200 mm or less, 500 mm or less, or 1000 mm or less, or in a range between any two of these values.

In the embodiment as shown in FIGS. 4A-4B and FIGS. 9A-9B, the wall 160 is continuous and surrounds the sample contact area 80. In other embodiments, the wall 160 does not have to be continuous, and there can be a gap between segments of a wall, and segments of a wall can be considered as multiple walls. That is, the sample contact area 80 can be surrounded by multiple walls. The total length of the walls can be in a range of 20 mm to 400 mm. In still other embodiments, there can be multiple walls, and each of the multiple walls can be continuously surrounding the sample contact area 80.

1.5. Sample Containment Ring Having Wells and Wall

Figure 11B:
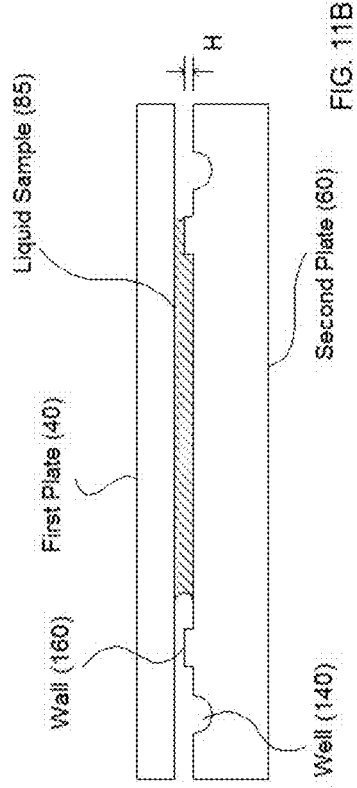
FIG. 11B shows part of a cross-section of an assaying device in FIG. 11A.
Figure 11A:
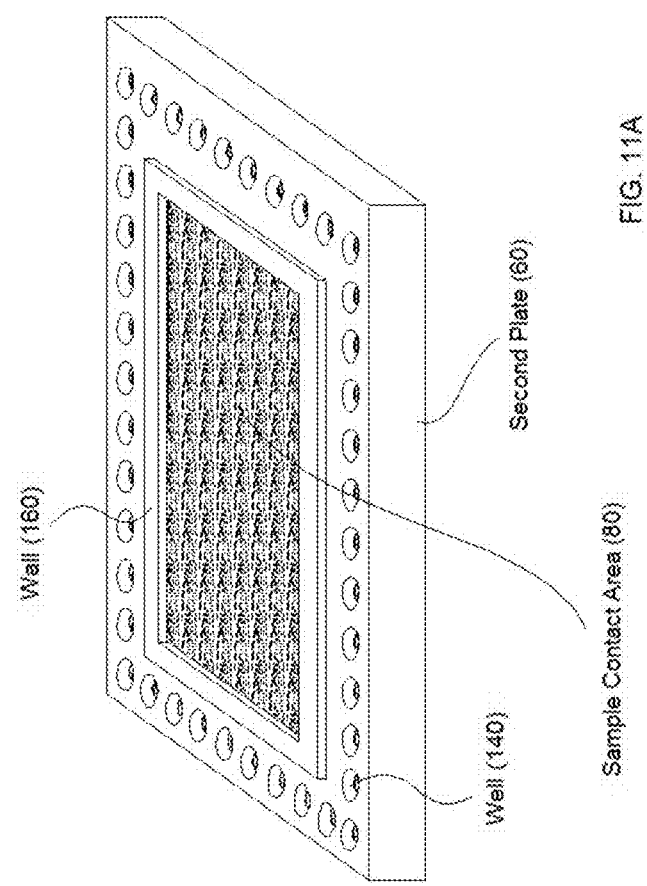
FIG. 11A depicts a three-dimensional view of a sample containment ring implemented with a wall and wells in another arrangement, in accordance with some embodiments of the present invention.

FIG. 10A depicts a three-dimensional view of a sample containment ring 120 implemented with a wall and wells in one arrangement in accordance with some embodiments. FIG. 10B shows part of a cross-section of an assaying device 100 in FIG. 10A. FIG. 11A depicts a three-dimensional view of a sample containment ring 120 implemented with a wall and wells in another arrangement in accordance with some embodiments. FIG. 11B shows part of a cross-section of an assaying device 100 in FIG. 11A. In FIGS. 10A-10B and FIGS. 11A-11B, the sample containment ring 120 surrounding the sample contact area 80 comprises both a wall 160 and wells 140 on the inner surface of the plate 60. In FIG. 10A, the wells 140 are arranged in a pattern that is surrounded by the wall 160. In FIG. 11A, the wells 140 are arranged in a pattern that surrounds the wall 160. In FIG. 10A and FIG. 11A, both the wall 160 and the formed pattern of the wells 140 surround the sample contact area 80.

Figure 12B:
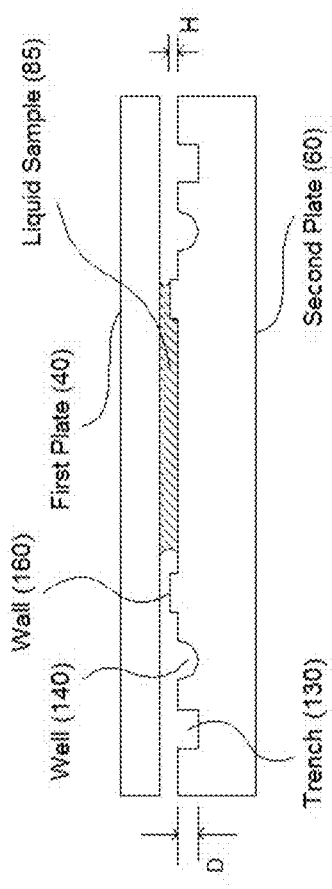
FIG. 12B shows part of a cross-section of an assaying device in FIG. 12A.
Figure 12A:
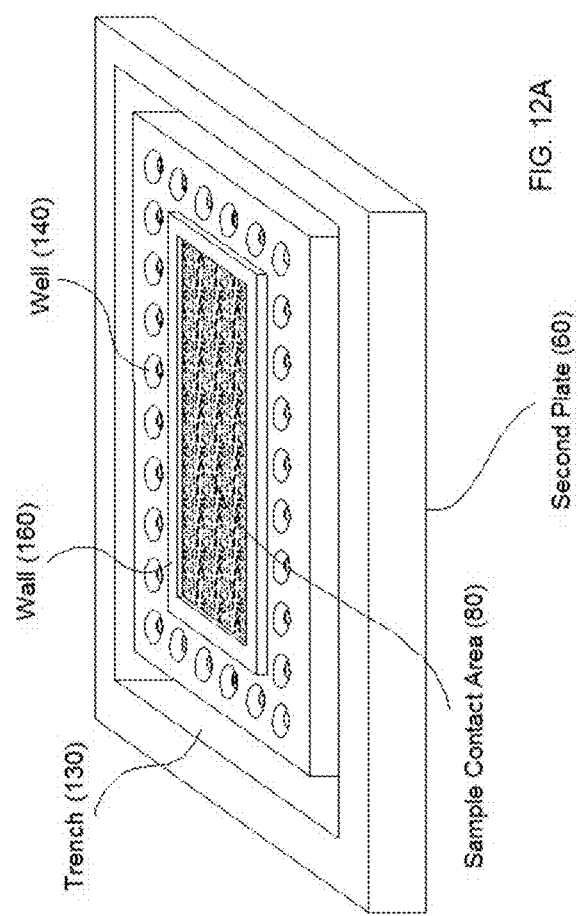
FIG. 12A depicts a three-dimensional view of a sample containment ring implemented with the combination of a trench, a wall, and wells, in accordance with some embodiments of the present invention.

1.6. Sample Containment Ring Having Wells in Combination with Trench and Wall FIG. 12A depicts a three-dimensional view of a sample containment ring 120 implemented with the combination of a trench, a wall, and wells in accordance with some embodiments. FIG. 12B shows part of a cross-section of an assaying device 100 in FIG. 12A. In FIGS. 12A-12B, the sample containment ring 120 surrounding the sample contact area 80 comprises a trench 130, a wall 160, and wells 140 on the inner surface of the plate 60. In FIGS. 12A-12B, the wells 140 are arranged in a pattern that is surrounded by the trench 130; such formed pattern of the wells, however, surrounds the wall 160. Other arrangements of the trench 130, the wall 160, and the wells 140 can be made. For example, the wells 140 can be arranged in a pattern that surrounds the trench 130 but is surrounded by the wall 160. Alternatively, the wells 140 can be arranged in a pattern that surrounds both the trench 130 and the wall 160. The wells 140 can be arranged in a pattern that is surrounded by both the trench 130 and the wall 160.

Figure 13B:
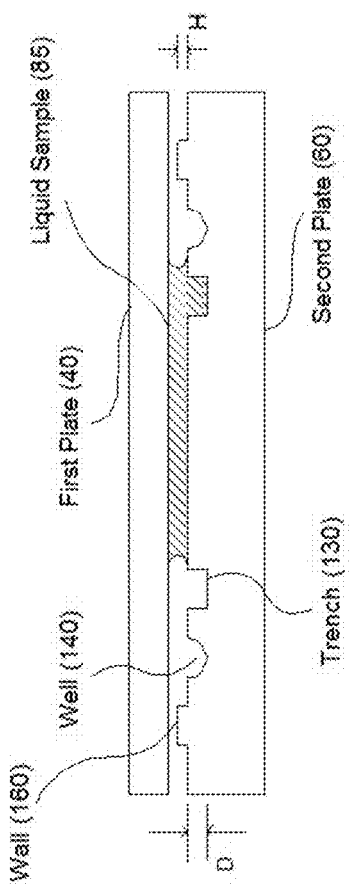
FIG. 13B shows part of a cross-section of an assaying device in FIG. 13A.
Figure 13A:
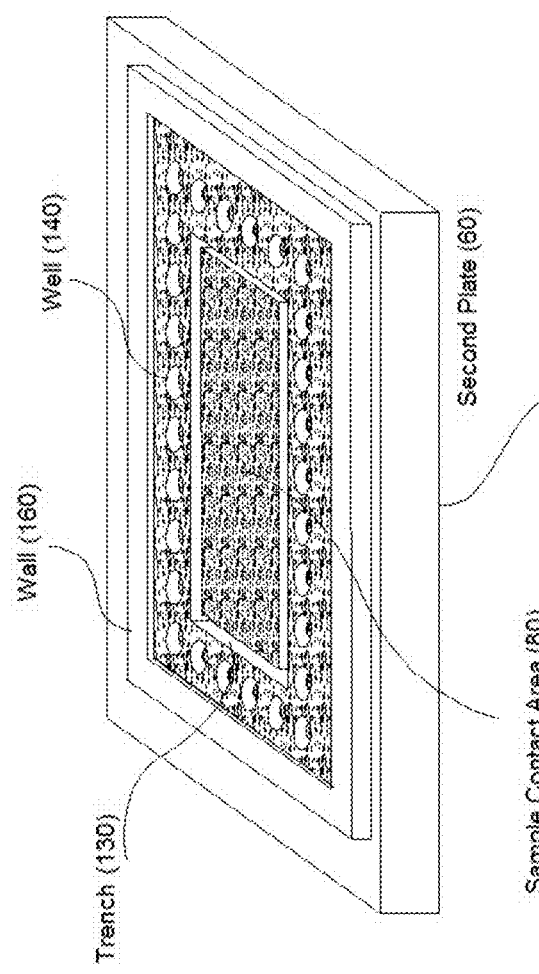
FIG. 13A depicts a three-dimensional view of a sample containment ring implemented with the combination of a trench, a wall, and wells, in accordance with some embodiments of the present invention.

FIG. 13A depicts a three-dimensional view of a sample containment ring 120 implemented with the combination of a trench, a wall, and wells in accordance with some embodiments. FIG. 13B shows part of a cross-section of an assaying device 100 in FIG. 13A. In FIGS. 13A-13B, the sample containment ring 120 surrounding the sample contact area 80 comprises a trench 130, a wall 160, and wells 140 on the inner surface of the plate 60. In FIGS. 13A-13B, the wells 140 are arranged in a pattern that is surrounded by the wall 160; such formed pattern of the wells, however, surrounds the trench 130. Other arrangements of the trench 130, the wall 160, and the wells 140 can be made. For example, the wells 140 can be arranged in a pattern that surrounds both the trench 130 and the wall 160.

1.7. Large Overflown Storage Volume

The term "maximum sample contact-area volume" refers to the maximum volume of the sample that can be accommodated by the sample area in a closed configuration of the plates.

In certain embodiments, the maximum sample contact-area volume is approximately equal to the plate area inside of the sample containing ring multiplying the average plate spacing in a closed configuration.

The term "overflown storage volume" refers to the maximum volume of the sample that can be accommodated by the sample containment ring in a closed configuration of the plates.

In certain embodiments, the depth of the well(s) and/or trench(es) are much larger than the plate spacing in a closed configuration, hence the overflown storage volume is approximately equal to the total volume of the well(s) and/or trench(es).

In certain applications, in order to avoid a sample overflowing, the sample overflown volume should be several times larger than the volume of the sample in the sample contact area when the plates of the device 100 in a closed configuration.

In certain embodiments, the ratio of the maximum storage volume to the maximum sample contact-area volume is at least 0.1, at least 0.2, at least 0.5, at least 1, at least 2, at least 3, at least 4, at least 5, at least 6, at least 7, at least 8, at least 9, at least 10, at least 15, at least 20, or at least 30.

In certain embodiments, the ratio of the maximum storage volume to the maximum sample contact-area volume is about 0.1, 0.2, 0.5, 1, 2, 3, 4, 5, 6, 7, 8, 9, 10, 15, 20, or 30, or in a range between any of the two values.

In certain embodiments, the ratio of the maximum storage volume to the maximum sample contact-area volume is 1, 2, 5, 10, 20, or 30, or in a range between any of the two values.

In certain embodiments, the maximum sample contact-area volume is 0.0001 µL, 0.005 µL, 0.01 µL, 0.05 µL, 0.1 µL, 0.5 µL, 1 µL, 5 µL, 10 µL, 50 µL, 100 µL, 500 µL, 1000 µL, or 5000 µL, or in a range between any of the two values.

In certain embodiments, the maximum sample contact-area volume is less than 0.001 µL, 0.005 µL, 0.01 µL, 0.05 µL, 0.1 µL, 0.5 µL, 1 µL, 5 µL, 10 µL, or 50 µL.

In certain embodiments, there is provided (a) the maximum sample contact-area volume is 0.0001 µL, 0.005 µL, 0.01 µL, 0.05 µL, 0.1 µL, 0.5 µL, 1 µL, 5 µL, 10 µL, 50 µL, 100 µL, 500 µL, 1000 µL, or 5000 µL, or in a range between any of the two values; and (b) the ratio of the maximum storage volume to the maximum sample contact-area volume is at least 0.1, at least 0.2, at least 0.5, at least 1, at least 2, at least 3, at least 4, at least 5, at least 6, at least 7, at least 8, at least 9, at least 10, at least 15, at least 20, or at least 30.

In certain embodiments, there is provided (a) the maximum sample contact-area volume is less than 0.001 µL, 0.005 µL, 0.01 µL, 0.05 µL, 0.1 µL, 0.5 µL, 1 µL, 5 µL, 10 µL, or 50 µL; and (b) the ratio of the maximum storage volume to the maximum sample contact-area volume is about 0.1, 0.2, 0.5, 1, 2, 3, 4, 5, 6, 7, 8, 9, 10, 15, 20, or 30, or in a range between any of the two values.

1.8. Examples of Preferred Embodiments

FIGS. 15-20 are schematics for showing some preferred embodiments of the sample confinement ring along with some of exemplary dimensions of the well, the trench, the wall, and the second plate. It should be noted that the designs and dimensions shown in FIGS. 15-20 are for demonstration purposes only and are not in any way limiting the scope of the invention.

Figure 15:
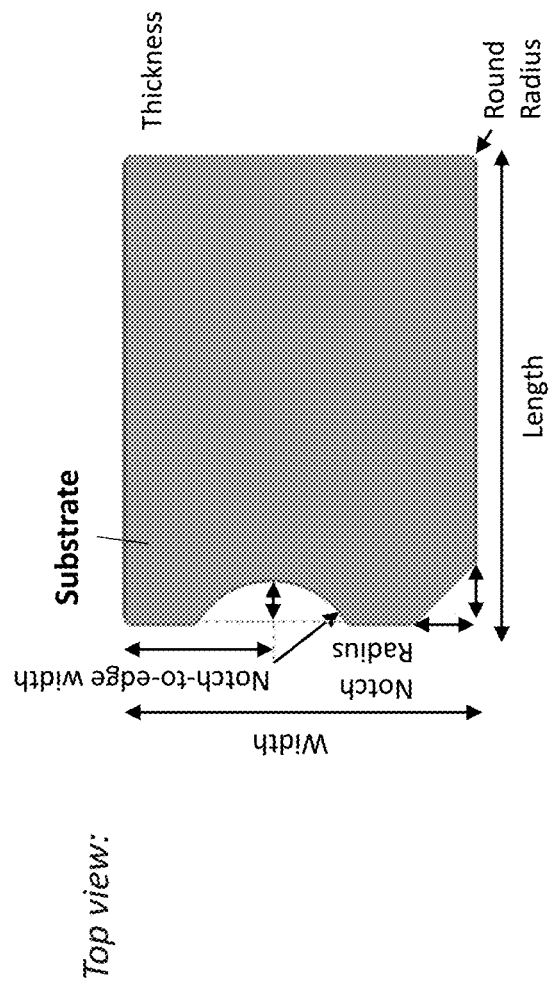
FIG. 15 shows a QMAX card of some embodiments of the present invention.

FIG. 15 depicts exemplary second plate (marked as a "substrate) in one of the preferred embodiments. In some embodiments, either the first plate or the second plate 20 can have a dimension (length or width) that is less than 5 mm, 10 mm, 20 mm, 50 mm, or 100 mm or in a range between any of the two number. In certain embodiments, the first plate or the second plate has a length that is in the range of 10-50 mm, 20-40 mm, or 30-35 mm. In certain embodiments, the first plate or the second plate has a width that is in the range of 5-45 mm, 15-35 mm, or 20-30 mm.

The second plate as shown in FIG. 15 generally has a length of about 32 mm and a width of about 24 mm. In some embodiments, the second plate has three rounded corners in which the circle forming rounded corner has a radius of 1 mm. In certain embodiments, one side of the second plate forms a notch in the form of an arch segment. In certain embodiments, the arch segment of the notch has a radius of 1-20 mm, or 3-10 mm. As shown in FIG. 15, in certain embodiments, the arch segment has a radius of about 6 mm. In certain embodiments, one corner of the second plate forms a corner notch in the shape of an isosceles right-angle triangle. In certain embodiments, the thickness of the second plate is about 1 mm.

Figure 16A:
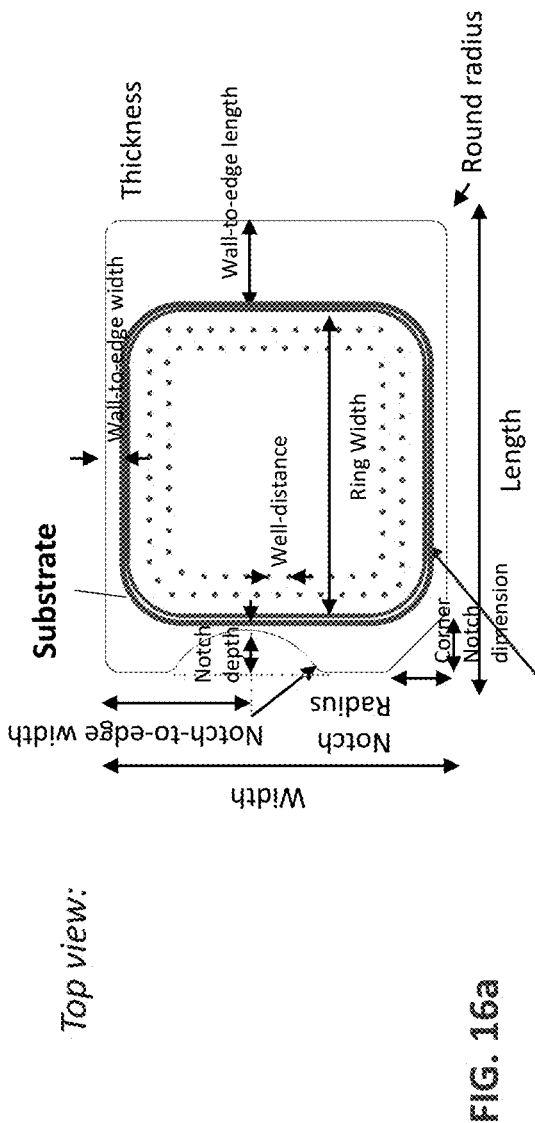
FIGS. 16A and 16B respectively show top and sectional views of a QMAX card that includes a sample containment ring according to some embodiments of the present invention.
Figure 16B:
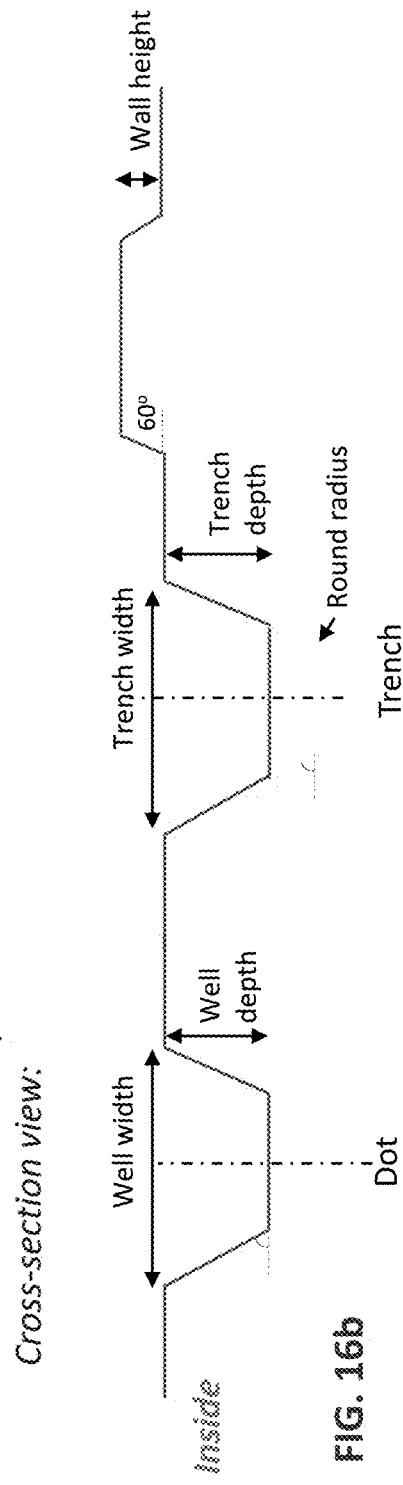

FIG. 16A and FIG. 16B are some schematics for a first example of a preferred embodiment of the sample confinement ring of the present invention. FIG. 16A shows a top view of the sample confinement ring, which includes two inner well rings each of which is generally formed by an alignment of wells. In some embodiments, the two inner well rings are enclosed by a ring of trench, which is further enclosed by a ring of wall.

FIG. 16B depicts a cross-sectional view of part of the sample confinement ring, demonstrating the cross-section of one exemplary well, the trench, and the wall shown in FIG. 16A. In certain embodiments, the well or the wall can have any sectional view shape. In some embodiments, the shape can include but not be limited to: triangle, rectangle, trapezoid, or partial circle. As an example, the well in FIG. 16B is in the form a truncated cone. In some embodiments, the depth of the well can be less than 05 µm, 50 µm, 0.01 mm, 0.02 mm, 0.05 mm, 0.1 mm, 0.2 mm, 0.5 mm, 1 mm, 2 mm, 5 mm, or in a range between any of the two values. In certain embodiments, the depth of the well is a range 5-20 µm, 20-50 µm, 50-100 µm, 50-150 µm, 50-500 µm, 0.005-2 mm, or 0.2-1 mm.

In some embodiments, the width (i.e., diameter) of the well is less than 0.005 mm, 0.01 mm, 0.02 mm, 0.05 mm, 0.1 mm, 0.2 mm, 0.5 mm, 1 mm, 2 mm, 5 mm, 10 mm, or 20 mm, or in a range between any of the two values.

In the embodiment shown in FIG. 16B, the depth of the well is about 0.15 mm and the base of the truncated cone has a diameter of about 0.5 mm. In certain embodiments, the sidewall of the well can have an including angle (e.g. 30 degrees, 45 degrees, 60 degrees, 75 degrees, 90 degrees, or 120 degrees, or in a range between any of the two values). In the embodiment shown in FIG. 16B, the sidewall of the well has an inclining angle of 60 degrees relative to its base of the truncated cone.

The wells can be periodically distributed or non-periodically distributed. In some embodiments, the period (i.e. the center-to-center distance) between the neighboring wells is substantially periodic (i.e. uniform) and in the range of 0.1-10 mm or 0.5-2 mm. In the embodiments shown in FIG. 16A, the period between the wells is 1 mm.

Further, in certain embodiments, the trench can have any perpendicular sectional view shape that allows for flowing of the sample into the well. In some embodiments, the shape can include but not be limited to: triangle, rectangle, trapezoid, or partial circle.

As shown in FIG. 18B, the cross section of at least one segment of the trench is in the form of isosceles trapezoid. In some embodiments, the depth and/or width (i.e. diameter) of the trench can be less than 0.01 mm, 0.02 mm, 0.05 mm, 0.1 mm, 0.2 mm, 0.5 mm, 1 mm, 2 mm, 5 mm, 10 mm, or 20 mm, or in a range between any of the two values. In certain embodiments, the depth and/or width of the trench is a range of 0.05-2 mm, or 0.2-1 mm. As shown in FIG. 16B, the depth of the trench is 0.15 mm, the base of the trench has a width of 0.5 mm.

In certain embodiments, the sidewall of the trench can have an including angle (e.g., 30 degrees, 45 degrees, 60 degrees, 75 degrees, 90 degrees, or 120 degrees, or in a range between any of the two values). In certain embodiments, the sidewall of the trench has an inclining angle of 60 degrees relative to its base of the trench.

Additionally, in certain embodiments, the sample containing ring comprises the wall. The wall can have any perpendicular sectional view shape that allows for flowing of the sample into the trench. In some embodiments, the shape can include but not be limited to: triangle, rectangle, trapezoid, or partial circle. As shown in FIG. 16B, in some embodiments, the cross section of at least one segment of the wall is in the form of isosceles trapezoid. In some embodiments, the height and/or width of the trench can be less than 0.005 mm, 0.01 mm, 0.02 mm, 0.05 mm, 0.1 mm, 0.2 mm, 0.5 mm, 1 mm, 2 mm, 5 mm, or 10 mm, or in a range between any of the two values. In certain embodiments, the height and/or width of the trench is a range of 0.005-0.1 mm, or 0.01-0.1 mm. As shown in FIG. 16B, the wall in FIG. 16B has a height of 0.02 mm. The side of the trapezoid has an inclining angle of 60 degrees relative to its base.

The sample confinement ring can have any shape that encircles the sample. For example, the sample confinement ring, including the well rings, the trench, and the wall, can have shape of triangle, rectangle, square, pentagon, hexagon, polygon, circle, or any combination and/or variations thereof.

In the embodiments shown in FIG. 16A, the sample confinement ring has a shape of modified square with round corners. The width of the square can vary, e.g., in the range of 5-50 mm, or 10-30 mm, or 15-25 mm. In certain embodiments, as shown in FIG. 16A, the width of the sample confinement ring is 19 mm. In some embodiments, the distance between the edge of the sample confinement ring and the long edge of the plate can be in the range of 0.1-10 mm or 1-3 mm. In the embodiment shown in FIG. 16A, the distance between the edge of the sample confinement ring and the long edge of the plate is 2 mm. In some embodiments, the distance between the edge of the sample confinement ring and the short edge of the plate can be in the range of 0.1-10 mm or 1-3 mm. In the embodiment shown in FIG. 16A, the distances between the edges of the sample confinement ring and the short edges of the plate is 2 mm and 8 mm.

The lateral geometry of the well or the trench can have a variety of the shapes, including but not limited to, rectangle, polygon, elliptic, triangle, trapezoid, or partial circle.

Figure 17A:
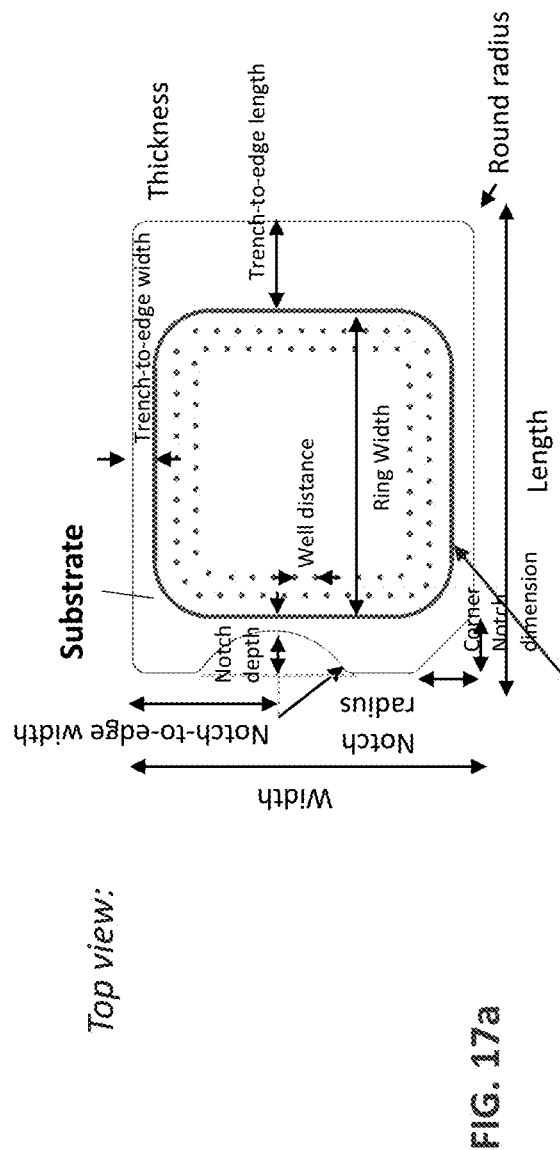
FIGS. 17A and 17B respectively show top and sectional views of a QMAX card that includes a sample containment ring according to some embodiments of the present invention.
Figure 17B:
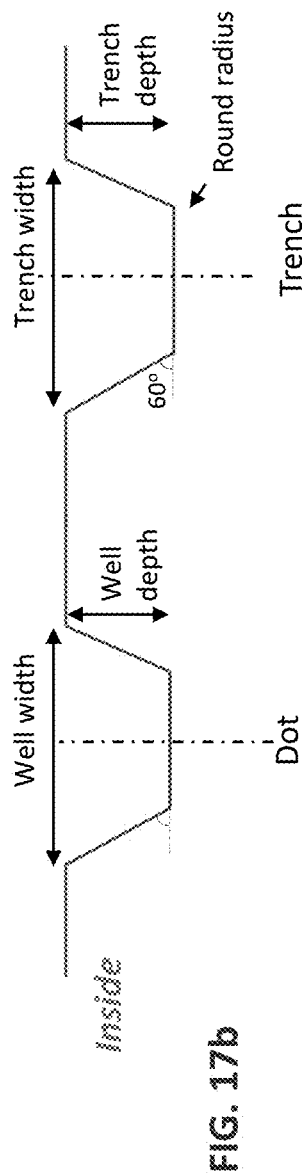

FIG. 17A and FIG. 17B are some schematics for another example of a preferred embodiment of the sample confinement ring. FIG. 17A shows a top view of the sample confinement ring, which includes two inner well rings each of which is generally formed by the alignment of wells. The two inner well rings are enclosed by a ring of trench. The wells and trench can have shape, width, depth ranges as indicated above. FIG. 17B shows a cross-sectional view of one example well that can be used in the sample confinement ring of FIG. 17A. The well in FIG. 17B is in the form a truncated cone. The depth of the well is 0.15 mm. In FIG. 17B, the base of the truncated cone has a diameter of 0.5 mm. The sidewall of the well has an inclining angle of 60 degrees relative to its base of the truncated cone. Further, FIG. 17B shows a cross-sectional view of one example trench that can be used in the sample confinement ring of FIG. 17A. The cross section of at least one segment of the trench is in the form of isosceles trapezoid as shown in FIG. 17B. The depth of the trench is 0.15 mm. The base of the trench has a width of 0.5 mm. The sidewall of the trench has an inclining angle of 60 degrees relative to its base of the trench.

The center-to-center separation between the two different well rings is 50 μm, 100 μm, 200 μm, 300 μm, 500 μm, 700 μm, 800 μm, 1000 μm, 2 mm, 3 mm, 4 mm, 5 mm, 10 mm, or in a range between the two values.

FIG. 18A and FIG. 18B are some schematics for a third example of a preferred embodiment of the sample confinement ring. FIG. 18A shows a top view of the sample confinement ring, which includes two inner well rings. The two inner well rings are enclosed by a ring of wall. The wells and wall can have shape and dimension ranges as indicated above. FIG. 18B shows a cross-sectional view of one example well that can be used in the sample confinement ring of FIG. A4a. The well in FIG. 18A is in the form a truncated cone. The depth of the well is 0.15 mm. In FIG. 18B, the base of the truncated cone has a diameter of 0.5 mm. The sidewall of the well has an inclining angle of 60 degrees relative to its base of the truncated cone. Further, FIG. 18B shows a cross-sectional view of one example wall that can be used in the sample confinement ring of FIG. 18A. The cross section of at least one segment of the wall is in the form of isosceles trapezoid as shown in FIG. A4b. The wall in FIG. 18B has a height of 0.02 mm. The opening width of the trapezoid (or the diameter of the well at its opening) is 0.5 mm. The side of the trapezoid has an inclining angle of 60 degrees relative to its base.

FIG. 19A and FIG. 19B are some schematics for a fourth example of a preferred embodiment of the sample confinement ring. FIG. 19A shows a top view of the sample confinement ring, which includes an inner ring of wall that is enclosed by a ring of trench. FIG. 19B shows a cross-sectional view of one example wall that can be used in the sample confinement ring of FIG. 19A. The trench and wall can have shape and dimension ranges as indicated above. The cross section of at least one segment of the wall is in the form of isosceles trapezoid as shown in FIG. 19B. The wall in FIG. 19B has a height of 0.005 mm. The base width of the trapezoid is 0.2 mm. The side of the trapezoid has an inclining angle of 60 degrees relative to its base. FIG. 19B shows a cross-sectional view of one example trench that can be used in the sample confinement ring of FIG. 19A. The cross section of at least one segment of the trench is in the form of isosceles trapezoid as shown in FIG. 19B. The depth of the trench is 0.15 mm. The base of the trench has a width of 0.6 mm. The sidewall of the trench has an inclining angle of 60 degrees relative to its base of the trench.

Figure 20A:
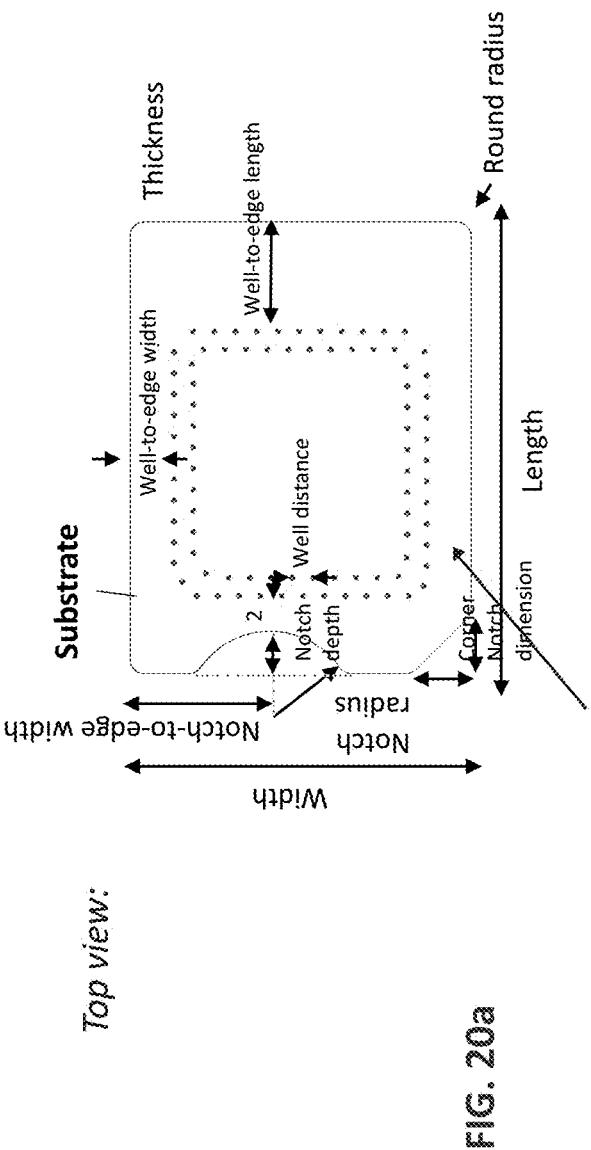
FIGS. 20A and 20B respectively show top and sectional views of a QMAX card that includes a sample containment ring according to some embodiments of the present invention.
Figure 20B:
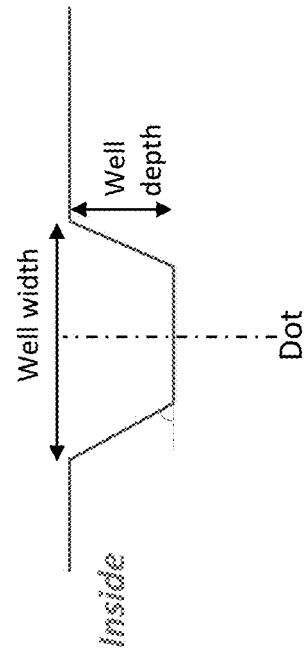

FIG. 20A and FIG. 20B are some schematics for a fifth example of a preferred embodiment of the sample confinement ring. FIG. 20A shows a top view the sample confinement ring includes two well rings each of which is generally formed by the alignment of wells. The wells and wall can have shape and dimension ranges as indicated above. FIG. 20B shows a cross-sectional view of one example well that can be used in the sample confinement ring of FIG. 20A. The well in FIG. 20B is in the form a truncated cone. The depth of the well is 0.15 mm. In FIG. 20B, the base of the truncated cone has a diameter of 0.6 mm.

1.9 Examples

FIGS. 16A-20B only illuminated a few exemplary dimensions of the well, the trench, and the wall for forming the sample confinement ring. The base diameter of the well can be 0.24 mm, 0.25 mm, 0.3 mm, 0.4 mm, 0.5 mm, or 0.6 mm. The depth of the well can be 0.10 mm, 0.15 mm, 0.18 mm, 0.20 mm, and 0.25 mm. The width of the trench can be 0.40 mm, 0.50 mm, 0.60 mm, and 0.75 mm. The depth of the trench can be 0.13 mm, 0.15 mm, 0.20 mm, and 0.25 mm. The base width of the wall can be 0.30 mm, 0.40 mm, 0.50 mm, and 0.75 mm. The height of the wall can be 0.005 mm, 0.01 mm, and 0.02 mm.

1.9.1 One Row of Wells

In some embodiments, the sample containment ring comprises a row of wells. Each well has a diameter of 500 μm and a depth of 150 μm. The wells are arranged in a closed rectangle ring shape using one row of the well, wherein each well has a separation from the neighboring well by 1000 μm, and wherein the rectangle ring has a length and a width is approximately 76 mm and 75 mm respectively.

1.9.2 Two Row of Wells

In some embodiments, the sample containment ring comprises two rows of wells. The wells are arranged in a closed rectangle ring shape using one row of the well, wherein each well has a separation from the neighboring well by 1000 μm, and wherein the rectangle ring has a length and a width is approximately 76 mm and 75 mm respectively.

1.9.3 One Row of Well and One Enclosed Ring Trench

In some embodiments, the sample containment ring comprises a row of wells and one enclosed ring trench, wherein the one enclosed ring trench is closer to the plate edges than the well. The wells are arranged in a closed rectangle ring shape using one row of the well, wherein each well has a center-to-center separation from the neighboring well by 1000 μm, and wherein the rectangle ring has a length and a width is approximately 76 mm and 75 mm respectively.

1.9.4 One Row of Well, One Enclosed Ring Trench, and One Enclosed Wall

In some embodiments, the sample containment ring comprises a row of wells, one enclosed ring trench, and one enclosed wall, wherein the enclosed wall is closer to the plate edges than the well and the trench, and the wells are closer to the sample contact area than the trench and the wall. The wells are arranged in a closed rectangle ring shape using one row of the well, wherein each well has a separation from the neighboring well by 1000 μm, and wherein the rectangle ring has a length and a width is approximately 76 mm and 75 mm respectively.

1.9.5 the Plate Spacing in a Closed Configuration

In some embodiments, the plate spacing in a closed configuration (CC) of the plates is 10 nm, 100 nm, 1 μm, 2 μm, 5 μm, 10 μm, 30 μm, 50 μm, 100 μm, 150 μm, 200 μm, 300 μm, 500 nm, or a range between the two values. The plate spacing in CC is 10 nm to 5 μm in some preferred embodiments, 1 μm to 50 μm in other preferred embodiments, 10 μm to 150 μm in other preferred embodiments, or 100 μm to 300 μm in other preferred embodiments.

2. Assays, Capture Agent, and Detection Agent

In some embodiments, the assay is a sandwich assay, in which capture agent and detection agent are configured to bind to analyte at different locations thereof, forming capture agent-analyte-detection agent sandwich.

In some embodiments, the assay is a competitive assay, in which analyte and detection agent compete with each other to bind to the capture agent.

In some embodiments, the assay is an immunoassay, in which protein analyte is detected by antibody-antigen interaction. In some embodiments, the assay is a nucleic acid assay, in which nucleic acids (e.g. DNA or RNA) are detected by hybridization with complementary oligonucleotide probes.

In some embodiments, the assay utilizes light signals as readout. In some embodiments, the assay utilizes magnetic signals as readout. In some embodiments, the assay utilizes electric signals as readout. In some embodiments, the assay utilizes signals in any other form as readout.

In some embodiments, the light signal from the assay is luminescence selected from photoluminescence, electroluminescence, and electrochemiluminescence. In some embodiments, the light signal is light absorption, reflection, transmission, diffraction, scattering, or diffusion. In some embodiments, the light signal is surface Raman scattering. In some embodiments, the electrical signal is electrical impedance selected from resistance, capacitance, and inductance. In some embodiments, the magnetic signal is magnetic relaxivity. In some embodiments, the signal is any combination of the foregoing signal forms.

There are many examples of analyte concentration surfaces that capture analyte using a capture agent, and the captured analyte are further bound with a label. As a first example, a protein concentration surface can be coated with capture antibodies. The capture antibodies capture the protein analyte in a sample, which is further bound with labeled detection antibodies. In this case, the capture antibody and detection antibody are configured to bind to the protein analyte at its different locations, therefore forming a capture antibody-protein analyte-detection antibody sandwich. As a second example, a nucleic acid concentration surface—can be coated with oligonucleotide capture probes. The capture probes are complementary to one part of the nucleic acid analyte, therefore capturing the analyte to the surface. Further, the analyte is bound with a labeled detection probe that is complementary to another part of the analyte. As a third example, protein analyte can be directly labeled by an optical label and captured by the capture antibodies that are coated on the concentration surface. As a fourth example, protein analyte can be bound with a quencher, which quenches the signal emitted by the label that is associated with the capture antibodies on the concentration surface. In this case, the concentration of the protein analyte to the concentration surface reduces the signal emanating from the concentration surface.

In some embodiments, the capture agent and the detection agent are configured to bind to the analyte at different locations thereof and to form a capture agent-analyte-detection agent sandwich that is immobilized to the separated nano-/micro-islands on one or both of the plates; wherein the shape of nano- or micro-islands are selected from the group consisting of sphere, rectangle, hexagon, and/or any other polyhedron, with lattice of square, hexagon, and/or any other lattices.

In some embodiments, the material of protrusions that are nano or micro islands are selected from the group consisting of plastic as polystyrene, polypropylene, polycarbonate, PMMA, PET; metals as gold, aluminum, silver, copper, tin and/or their combinations; or any other material whose surface can be modified to be associated with the capture agent.

As discussed above, in some embodiments, the beads, the capture agent, and the detection agent are configured to render signal of the bead-captured analyte distinguishable from signal of free detection agent in the layer of uniform thickness. In some embodiments, it is critical to achieve the foregoing configuration, in that only if the signal from the sandwich structure is distinguishable from the "background" signal of the free detection agent in the layer of uniform thickness, one can use the detected signals as a readout of the presence and/or quantity of the analyte in the sample, thereby realizing the assay.

In some embodiments, the target analyte competes with the detection agent on the capture locations on beads. When more target analyte appears, beads become relative dark.

In some embodiments, the beads are associated with a label, and the detection agent is a quencher that is configured to quench signal of the beads-associated label when the detection agent is in proximity of the label. When beads capture the target analyte, the label on beads become quenched or dimed.

In some embodiments, the capture agent comprises, but not limited to, protein, peptide, peptidomimetics, streptavidin, biotin, oligonucleotide, oligonucleotide mimetics, any other affinity ligand and any combination thereof. In some embodiments, the capture agent is an antibody. In some embodiments, the capture antibody is an anti-C Reactive Protein (CRP) antibody.

In some embodiments, the capture agent has a concentration that is sufficient to detect the presence and/or measure the amount of the analyte. In some embodiments, the capture agent has a concentration that is sufficient to immobilize the analyte.

In some embodiments, the detection agent comprises, but not limited to, protein, peptide, peptidomimetics, streptavidin, biotin, oligonucleotide, oligonucleotide mimetics, any other affinity ligand and any combination thereof. In some embodiments, the detection agent is an antibody. In some embodiments, the detection antibody is an anti-CRP antibody.

In some embodiments, the detection antibody is configured to have a concentration in the layer of uniform thickness that is higher than analyte concentration in the sample. In some embodiments, the ratio of the detection antibody concentration over the analyte concentration is 1 or more, 2 or more, 5 or more, 10 or more, 20 or more, 30 or more, 50 or more, 100 or more, 200 or more, 300 or more, 500 or more, 1000 or more, or in a range between any two of these values.

In some embodiments, the detection antibody is labeled. In some embodiments, the label can be fluorescent, colorimetric or luminescent. In some embodiments, the detection antibody is labeled with a fluorophore. In some embodiments, the fluorophores comprise, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins comprise, but are not limited to, a green fluorescent protein (GFP), including, but not limited to, a GFP derived from Aequoria victoria or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from Anthozoan species; combinations thereof; and the like.

In some embodiments, the beads are treated with a protein stabilizer. In some embodiments, the beads can be deposited on the plate and dried (e.g. air-dried), further simplifying the process. In some embodiments, the detection antibody is placed on one of the plates and dried. In some embodiments, the plate with the detection antibody is treated with protein stabilizer. In some embodiments, the detection antibody with protein stabilizer is pre-printed on one of the plates and air-dried.

In some embodiments, the beads are prepared by:
(a) activating with N-Hydroxysuccinimide (NHS);
(b) blocking with a BSA solution; and
(c) incubating with a capture agent solution.

3. Detector, System and Smartphone-Based System

Another aspect of the present invention provides a system for homogeneous assay. In some embodiments, the system comprises the device as discussed above and a detector that detects the analyte in the layer of uniform thickness.

In some embodiments, detector detects a signal from the capture agent-analyte-detection agent sandwich indicative of the presence and/or quantity of the analyte.

In some embodiments, the signal is:
i. luminescence selected from photoluminescence, electroluminescence, and electrochemiluminescence;
ii. light absorption, reflection, transmission, diffraction, scattering, or diffusion;
iii. surface Raman scattering;
iv. electrical impedance selected from resistance, capacitance, and inductance;
v. magnetic relaxivity; or
vi. any combination of i-v.

Another aspect of the present invention provides a smartphone system for homogeneous assay. In some embodiments, the smartphone system comprises:
(a) a device of any aforementioned embodiment;
(b) a mobile communication device that comprises:
 i. one or a plurality of cameras for detecting and/or imaging the sample;
 ii. electronics, signal processors, hardware and software for receiving and/or processing the detected signal and/or the image of the sample and for remote communication; and
(c) an adaptor configured to hold the closed device and engageable to mobile communication device;
wherein when engaged with the mobile communication device, the adaptor is configured to facilitate the detection and/or imaging of the analyte in the sample at the closed configuration.

In some embodiments, the mobile communication device is configured to communicate test results to a medical professional, a medical facility or an insurance company.

In some embodiments, the mobile communication device is further configured to communicate information on the subject with the medical professional, medical facility or insurance company.

In some embodiments, the mobile communication device is configured to receive a prescription, diagnosis or a recommendation from a medical professional.

In some embodiments, the mobile communication device communicates with the remote location via a wifi or cellular network.

In some embodiments, the mobile communication device is a mobile phone.

In some embodiments, the images can be taken by a camera that is part of a mobile device. In some embodiments, the mobile device is a smart phone.

Figure 14:
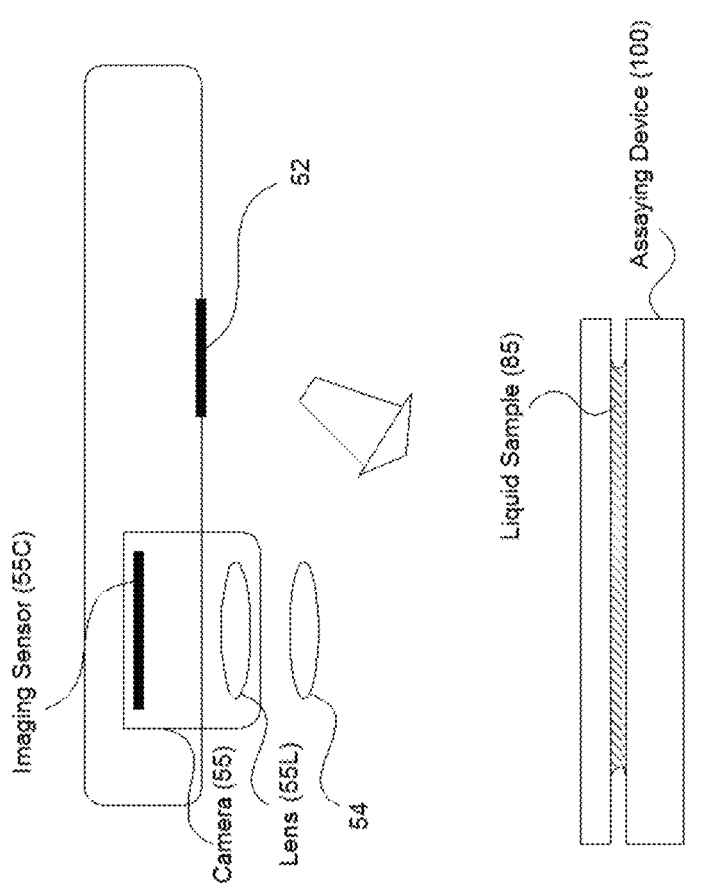
FIG. 14 is a schematic of a system for imaging a liquid sample in the assaying device with a camera in a smartphone, in accordance with some embodiments of the present invention.

An example of an assaying system is shown in FIG. 14. The assaying device 100 is illuminated with illumination light from an illumination source 52. The illumination light passing through the first plate 40 is scattered by the liquid sample 85 between the first plate 40 and the second plate 60. The scattered light from the liquid sample 85 pass through the first plate 40 and is detected by a camera 55. Images of the liquid sample 85 are captured by the imaging sensor 55C through a lens 55L in the camera 55. The captured images are processed with imaging processing software or other analytic software for detecting interested analytes in the liquid sample 85. In order to improve the quality of the captured images to achieve better analysis of the analytes, an additional lens 54 can be placed between the assaying device 100 and the camera 55 as shown in the figure.

4. Analyte, Sample and Application

In some embodiments, the analyte to be detected in the homogeneous assay comprises, but not limited to, cells, viruses, proteins, peptides, DNAs, RNAs, oligonucleotides, and any combination thereof.

In some embodiments, the present invention finds use in detecting biomarkers for a disease or disease state. In certain instances, the present invention finds use in detecting biomarkers for the characterization of cell signaling pathways and intracellular communication for drug discovery and vaccine development. For example, the present invention can be used to detect and/or quantify the amount of biomarkers in diseased, healthy or benign samples. In certain embodiments, the present invention finds use in detecting biomarkers for an infectious disease or disease state. In some cases, the biomarkers can be molecular biomarkers, such as but not limited to proteins, nucleic acids, carbohydrates, small molecules, and the like. The present invention find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The present invention has applications in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

In some embodiments, the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

In some embodiments, the sample is an environmental gaseous sample from a source selected from the group consisting of: the air, underwater heat vents, industrial exhaust, vehicular exhaust, and any combination thereof.

In some embodiments, the sample is a foodstuff sample selected from the group consisting of: raw ingredients, cooked food, plant and animal sources of food, preprocessed food, and partially or fully processed food, and any combination thereof.

5. Examples of Present Invention

In one embodiment, the present invention provides a device for assaying a liquid sample, comprising:
   a first plate, a second plate, and a sample containment ring, wherein:
      vi. the first plate and second plate are movable relative to each other into different configurations, including an open configuration and a closed configuration;
      vii. each of the plates comprises an inner surface that has a sample contact area for depositing and/or contacting a liquid sample;
      viii. the sample containment ring is on an inner surface of one or both of the plates and surrounds the sample contact areas;
      ix. the sample containment ring comprises at least one sample containment feature; and
      x. the sample containment ring is configured to reduce or prevent the sample deposited on the plate flowing out of an edge of the plates,
   wherein the open configuration is a configuration in which the plates are partially or entirely separated apart, the average spacing between the sample contact areas of the plates is larger than 300 µm, and the sample is deposited on the sample contact area of one or both plates; and
   wherein the closed configuration is a configuration, in which the average spacing between the sample contact areas of the plates is in a range of 0.1 µm to 200 µm.

In another embodiment, the present invention provides a device for assaying a liquid sample, comprises:
   a first plate, a second plate, spacers, and a sample containment ring, wherein:
      vii. the first and second plates are movable relative to each other into different configurations, including an open configuration and a closed configuration;
      viii. each of the plates comprises an inner surface that has a sample contact area for contacting a liquid sample, and
      ix. the spacers are fixed on the inner surface of at least one plate, and at least one of the spacers is in the sample contact area;
      x. the sample containment ring that is on an inner surface of one of the plates and surrounds the sample contact area;
      xi. the sample containment ring comprises at least one sample containment feature; and
      xii. the sample containment ring is configured to reduce or prevent the sample deposited on the plate flowing out of an edge of the plates,
   wherein in the open configuration, the two plates are partially or entirely separated apart and the spacing between the sample contact areas of the plates is not regulated by the spacers, and the sample is deposited on a sample contact area of one or both of the plates;
   and wherein in the closed configuration, at least part of the sample deposited in the open configuration is confined between the surfaces of the sample contact areas, and the spacing between the sample contact areas of the plates is regulated by the spacers and is in the range of 10 nm to 200 µm.

Preferably, the at least sample containment feature is a well that that is configured to hold a portion of the sample.

Preferably, the at least sample containment feature is a trench that that is configured to hold a portion of the sample.

Preferably, the at least sample containment feature is a wall that impedes a sample flowing out an edge of a plate.

Preferably, the sample containment ring further comprises at least a plurality of wells that are configured to hold a portion of the sample.

Preferably, the sample containment ring further comprises at least a plurality of trenches that are configured to hold a portion of the sample.

Preferably, the sample containment ring further comprises at least a plurality of walls that impede a sample flowing out an edge of a plate.

Preferably, the sample containment ring further comprises one or a plurality of wells, trenches, walls, or a combination of thereof.

Preferably, in the closed configuration of the plates, the wall on one of plates does not touch the surface of the other plate.

In another embodiment, the present invention provides a method for assaying a liquid sample, comprising:
  (a) obtaining a device of any prior device embodiments;
  (b) obtaining a liquid sample, which contains or is suspected of containing an analyte;
  (c) depositing the sample on one or both of the sample contact areas when the plates are in the open configuration;
  (d) pressing the plates into the closed configuration to compress at least part of the sample into a layer of uniform thickness; and
  (e) analyzing a signal from the analyte in the sample.

Preferably, the pressing of step (d) is conducted with human hand.

In another embodiment, the present invention provides a system for assaying a liquid sample, comprising:
  (a) the device of any prior device embodiments,
  (b) an adaptor that is configured to accommodate the device and connect to a mobile apparatus, wherein:
    the mobile apparatus comprises a camera,
    the adaptor is configured to position the liquid sample in a field of view (FOV) of the camera when the adaptor is connected to the mobile apparatus.

Preferably, the mobile apparatus is configured to:
detect a signal related to an analyte in the sample; and
analyze the signal to determine the presence and/or concentration of the analyte in the sample.

Preferably, the mobile apparatus is configured to capture images of the sample and measuring a signal related to an analyte in the images.

Preferably, the maximum storage volume is larger than the maximum sample contact-area volume.

Preferably, the maximum storage volume is larger than the volume of the sample that is deposited on the plate.

Preferably, the ratio of the maximum storage volume to the maximum sample contact-area volume is at least 0.1, at least 0.2, at least 0.5, at least 1, at least 2, at least 3, at least 4, at least 5, at least 6, at least 7, at least 8, at least 9, at least 10, at least 15, at least 20, or at least 30.

Preferably, the ratio of the maximum storage volume to the maximum sample contact-area volume is about 0.1, 0.2, 0.5, 1, 2, 3, 4, 5, 6, 7, 8, 9, 10, 15, 20, or 30, or in a range between any of the two values.

Preferably, the ratio of the maximum storage volume to the maximum sample contact-area volume is 1, 2, 5, 10, 20, or 30, or in a range between any of the two values.

Preferably, the maximum sample contact-area volume is 0.0001 μL, 0.005 μL, 0.01 μL, 0.05 μL, 0.1 μL, 0.5 μL, 1 μL, 5 μL, 10 μL, 50 μL, 100 μL, 500 μL, 1000 μL, or 5000 μL, or in a range between any of the two values.

Preferably, the maximum sample contact-area volume is less than 0.001 μL, 0.005 μL, 0.01 μL, 0.05 μL, 0.1 μL, 0.5 μL, 1 μL, 5 μL, 10 μL, or 50 μL.

Preferably, the maximum sample contact-area volume is 0.0001 μL, 0.005 μL, 0.01 μL, 0.05 μL, 0.1 μL, 0.5 μL, 1 μL, 5 μL, 10 μL, 50 μL, 100 μL, 500 μL, 1000 μL, or 5000 μL, or in a range between any of the two values; and the ratio of the maximum storage volume to the maximum sample contact-area volume is at least 0.1, at least 0.2, at least 0.5, at least 1, at least 2, at least 3, at least 4, at least 5, at least 6, at least 7, at least 8, at least 9, at least 10, at least 15, at least 20, or at least 30.

Preferably, the maximum sample contact-area volume is less than 0.001 μL, 0.005 μL, 0.01 μL, 0.05 μL, 0.1 μL, 0.5 μL, 1 μL, 5 μL, 10 μL, or 50 μL; and the ratio of the maximum storage volume to the maximum sample contact-area volume is about 0.1, 0.2, 0.5, 1, 2, 3, 4, 5, 6, 7, 8, 9, 10, 15, 20, or 30, or in a range between any of the two values.

Preferably, in a closed configuration of the plates, at least a portion of the sample containment ring on one plate is separated from the other plate by a gap.

Preferably in a closed configuration of the plates, the two plates, that contact spacers, do not directly contact each other in the surface area that does not contact the spacers.

Preferably, the well comprises a plurality of wells that are organized as one row around the sample contact area.

Preferably, the well comprises a plurality of wells that are organized as two or more rows around the sample contact area.

Preferably, the trench comprises a continuous trench that encircles the sample contact area.

Preferably, the trench comprises a segmented trench.

Preferably, the trenches comprise a plurality of segmented trenches that encircle the sample contact area.

Preferably, the walls are positioned on one or both of the plates partially or entirely around the sample contact area to impede overflow of sample in the closed configuration.

Preferably, the sample containment ring comprises a plurality of wells and a stopping wall positioned on one or both of the plates partially or entirely around the sample contact area to block overflow of sample in the closed configuration.

Preferably, the sample containment ring comprises one or more trenches and a stopping wall positioned on one or both of the plates partially or entirely around the sample contact area to block overflow of sample in the closed configuration.

Preferably, the sample containment ring comprises: a trench continuously surrounding the sample contact area, the trench having a width of 0.001 μm or less, 0.005 μm or less, 0.01 μm or less, 0.05 μm or less, 0.1 μm or less, 0.5 μm or less, 1 μm or less, 2 μm or less, 5 μm or less, 10 μm or less, 20 μm or less, 50 μm or less, 100 μm or less, 200 μm or less, 500 μm or less, or 1000 μm or less, or in a range between any two of these values.

Preferably, the sample containment ring comprises: a trench continuously surrounding the sample contact area, the trench having a depth of 0.001 μm or less, 0.005 μm or less, 0.01 μm or less, 0.05 μm or less, 0.1 μm or less, 0.5 μm or less, 1 μm or less, 2 μm or less, 5 μm or less, 10 μm or less, 20 μm or less, 50 μm or less, 100 μm or less, 200 μm or less, 500 μm or less, or 1000 μm or less, or in a range between any two of these values.

Preferably, the sample containment ring comprises: a trench continuously surrounding the sample contact area, the trench having a total length of 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, 200 mm or less, 500 mm or less, or 1000 mm or less, or in a range between any two of these values.

Preferably, the sample containment ring comprises: a trench continuously surrounding the sample contact area, the trench having a width thereof between 0.2 μm to 200 μm and having a depth thereof ranged from 0.02 μm to 20 μm, and wherein a total length the trench is ranged from 20 mm to 40 mm.

Preferably, the sample containment ring comprises: a plurality of trenches each continuously surrounding the sample contact area, each of the trenches having a width of 0.001 μm or less, 0.005 μm or less, 0.01 μm or less, 0.05 μm or less, 0.1 μm or less, 0.5 μm or less, 1 μm or less, 2 μm or less, 5 µm or less, 10 µm or less, 20 µm or less, 50 µm or less, 100 µm or less, 200 µm or less, 500 µm or less, or 1000 µm or less, or in a range between any two of these values, a depth of 0.001 µm or less, 0.005 µm or less, 0.01 µm or less, 0.05 µm or less, 0.1 µm or less, 0.5 µm or less, 1 µm or less, 2 µm or less, 5 µm or less, 10 µm or less, 20 µm or less, 50 µm or less, 100 µm or less, 200 µm or less, 500 µm or less, or 1000 µm or less, or in a range between any two of these values, and wherein a total length the trenches is 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, 200 mm or less, 500 mm or less, or 1000 mm or less, or in a range between any two of these values.

Preferably, the sample containment ring further comprises: a plurality of trenches, each of the trenches having a width thereof ranged from 0.2 µm to 200 µm and having a depth thereof ranged from 0.02 µm to 20 µm, and wherein a total length of the trenches is ranged from 20 mm to 400 mm.

Preferably, the sample containment ring comprises: a wall continuously surrounding the sample contact area, the wall having a width of 0.001 µm or less, 0.005 µm or less, 0.01 µm or less, 0.05 µm or less, 0.1 µm or less, 0.5 µm or less, 1 µm or less, 2 µm or less, 5 µm or less, 10 µm or less, 20 µm or less, 50 µm or less, 100 µm or less, 200 µm or less, 500 µm or less, or 1000 µm or less, or in a range between any two of these values, a height of 0.001 µm or less, 0.005 µm or less, 0.01 µm or less, 0.05 µm or less, 0.1 µm or less, 0.5 µm or less, 1 µm or less, 2 µm or less, 5 µm or less, 10 µm or less, 20 µm or less, 50 µm or less, 100 µm or less, 200 µm or less, 500 µm or less, or 1000 µm or less, or in a range between any two of these values, and wherein a total length of the wall is 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, 200 mm or less, 500 mm or less, or 1000 mm or less, or in a range between any two of these values.

Preferably, the sample containment ring comprises: a wall continuously surrounding the sample contact area, the wall having a width thereof ranged from 0.2 µm to 200 µm and having a height thereof ranged from 0.02 µm to 20 µm, and wherein a total length of the wall is ranged from 20 mm to 400 mm.

Preferably, the sample containment ring comprises: a plurality of walls each continuously surrounding the sample contact area, each of the walls having a width of 0.001 µm or less, 0.005 µm or less, 0.01 µm or less, 0.05 µm or less, 0.1 µm or less, 0.5 µm or less, 1 µm or less, 2 µm or less, 5 µm or less, 10 µm or less, 20 µm or less, 50 µm or less, 100 µm or less, 200 µm or less, 500 µm or less, or 1000 µm or less, or in a range between any two of these values, a height of 0.001 µm or less, 0.005 µm or less, 0.01 µm or less, 0.05 µm or less, 0.1 µm or less, 0.5 µm or less, 1 µm or less, 2 µm or less, 5 µm or less, 10 µm or less, 20 µm or less, 50 µm or less, 100 µm or less, 200 µm or less, 500 µm or less, or 1000 µm or less, or in a range between any two of these values, and wherein a total length of the walls is 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, 200 mm or less, 500 mm or less, or 1000 mm or less, or in a range between any two of these values.

Preferably, the sample containment ring comprises: a plurality of walls, each of the walls having a width thereof ranged from 0.2 µm to 200 µm and having a height thereof ranged from 0.02 µm to 20 µm, and wherein a total length of the walls is ranged from 20 mm to 400 mm.

Preferably, the sample containment ring further comprises: a plurality of trenches, each of the trenches having a width thereof ranged from 0.2 µm to 200 µm and having a depth thereof ranged from 0.02 µm to 20 µm, and wherein a total length of the trenches is ranged from 20 mm to 400 mm.

Preferably, the sample containment ring comprises: a plurality of wells each having a volume of less than 0.001 µL, less than 0.005 µL, less than 0.01 µL, less than 0.05 µL, less than 0.1 µL, less than 0.5 µL, less than 1 µL, less than 5 µL, less than 10 µL, less than 50 µL, less than 100 µL, less than 500 µL, less than 1000 µL, or less than 5000 µL, or in a range between any of the two values.

Preferably, the sample containment ring comprises: a plurality of wells each having a volume thereof ranged from $0.001\ \mu m^3$ to $1000\ \mu m^3$.

Preferably, a shape of each well is one of a solid rectangular, a cylinder, a spheroidal cap, and a wedge.

, the sample containment ring further comprises: a trench continuously surrounding the sample contact area, the trench having a width thereof ranged from 0.2 µm to 200 µm and having a depth thereof ranged from 0.02 µm to 20 µm, and wherein a total length the trench is ranged from 20 mm to 400 mm.

Preferably, the wells are arranged in a pattern that is surrounded by the trench.

Preferably, the wells are arranged in a pattern that surrounds the trench.

Preferably, the sample containment ring further comprises: a plurality of trenches, each of the trenches having a width thereof ranged from 0.2 µm to 200 µm and having a depth thereof ranged from 0.02 µm to 20 µm, and wherein a total length of the trenches is ranged from 20 mm to 400 mm.

Preferably, the wells are arranged in a pattern that is surrounded by the trench.

Preferably, the wells are arranged in a pattern that surrounds the trench.

Preferably, a ratio of an overflow sample volume over the volume of a sample contact zone ranges from 2 to 20 and the overflow sample volume equals to the total volume of the plurality of wells.

a ratio of an overflow sample volume to the volume of a sample contact zone ranges from 4 to 10 and the overflow sample volume equals to the total volume of the plurality of wells.

Preferably, the sample containment ring further comprises one or more trenches, and wherein a ratio of an overflow sample volume over the volume of a sample contact zone ranges from 2 to 20, and the overflow sample volume equals to the total volume of the plurality of wells plus the total volume of the one or more trenches.

Preferably, the sample containment ring further comprises one or more trenches, and wherein a ratio of an overflow sample volume over the volume of a sample contact zone ranges from 4 to 10, and the overflow sample volume equals to the total volume of the plurality of wells plus the total volume of the one or more trenches.

Preferably, the sample containment ring further comprises: a wall continuously surrounding the sample contact area, the wall having a width thereof ranged from 0.2 µm to 200 µm and having a height thereof ranged from 0.02 µm to 20 µm, and wherein a total length of the wall is ranged from 20 mm to 400 mm.

Preferably, the wells are arranged in a pattern that is surrounded by the wall.

Preferably, the wells are arranged in a pattern that surrounds the wall.

Preferably, the sample containment ring further comprises: a plurality of walls, each of the walls having a width thereof ranged from 0.2 μm to 200 μm and having a height thereof ranged from 0.02 μm to 20 μm, and wherein a total length of the walls is ranged from 20 mm to 400 mm.

Preferably, the wells are arranged in a pattern that is surrounded by the wall.

Preferably, the wells are arranged in a pattern that surrounds the wall.

Preferably, the sample is original, diluted, or processed forms of: bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, or exhaled breath condensate.

Preferably, the sample is original, diluted, or processed forms of blood.

Preferably, the sample comprises whole blood.

Preferably, the sample is a biological sample, a chemical sample, an environmental sample, or a foodstuff sample.

Preferably, the analyte is a biomarker, an environmental marker, or a foodstuff marker.

Preferably, the analyte is a biomarker indicative of the presence or severity of a disease or condition.

Preferably, the analyte is a cell, a protein, or a nucleic acid.

Preferably, the analyte comprises proteins, peptides, nucleic acids, synthetic compounds, inorganic compounds, organic compounds, bacteria, virus, cells, tissues, nanoparticles, and other molecules, compounds, mixtures and substances thereof.

Preferably, analyte is selected from Table B1, B2, B3 or B7 of PCT Application No. PCT/US2016/054,025.

Preferably, the sample holder comprises wells that configured to hold the sample.

Preferably, the sample holder comprises a first plate, and a second plate, and spacers.

Preferably, the sample holder comprises a first plate, a second plate, and spacers, wherein the spacers are configured to regulate a gap between the plates when the plates are pressed against each, compressing the sample into a thin layer.

Preferably, the sample holder comprises a first plate, a second plate, and spacers, and wherein:
  i. the plates are moveable relative to each other into different configurations, including an open configuration and a closed configuration;
  ii. in the open configuration: the two plates are separated apart, the spacing between the plates is not regulated by the spacers, and the sample is deposited on one or both of the plates; and
  iii. in the closed configuration, which is configured after the sample deposition in the open configuration: at least part of the sample is compressed by the two plates into a layer of highly uniform thickness and is substantially stagnant relative to the plates, wherein the uniform thickness of the layer is regulated by the plates and the spacers.

Preferably, the sample holder comprises a Q-card, which comprises a first plate, a second plate, and spacers, wherein the spacers are configured to regulate a gap between the plates when the plates are pressed against each, compressing the sample into a thin layer.

Preferably, the sample holder comprises a first plate, a second plate, and spacers, wherein the spacers have a uniform height and a constant inter-spacer distance; and the sample is compressed by the sample holder into a thin layer with a uniform thickness that is regulated by the height of the spacers.

Preferably, the sample is compressed into a layer of uniform thickness that substantially equals uniform height of spacers that are fixed to one or both of the plates.

the sample is compressed into a layer of uniform thickness that has a variation of less than 15%, 10%, 5%, 2%, 1%, or in a range between any of the two values.

Preferably, in the closed configuration, the sample has a thickness of 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, or in a range between any two of these values.

Preferably, in the closed configuration, the sample has a thickness in the range of 0.5-20 μm.

Preferably, the closed configuration, a gap between the first plate and the second plate is 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, or in a range between any two of these values.

Preferably, the sample holder comprises a first plate and a second plate, wherein each of the plate has a thickness of 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, or in a range between any two of these values.

Preferably, the imager comprises a camera.

Preferably, the imager is a part of the detector.

Preferably, the imager is the entirety of the detector.

Preferably, the imager is directed by the software to capture one or more images of the sample, identify the interference element regions and the interference element free regions, and digitally separate the interference element regions from the interference element free regions.

Preferably, the imager comprises a filter that is configured to filter signals from the sample.

Preferably, the imager comprises a light source that is configured to illuminate the sample.

Preferably, the detector is a mobile device.

Preferably, the detector is a smart phone.

Preferably, the detector is a smart phone and the imager is a camera as part of the smart phone.

Preferably, the detector comprises a display that is configured to show the presence and/or amount of the analyte.

Preferably, the detector is configured to transmit detection results to a third party.

Preferably, the software is stored in a storage unit, which is part of the detector.

Preferably, the software is configured to direct the detector to display the presence and/or amount of the analyte.

Preferably, the software is configured to direct the imager to calculate the combined signal of the analyte from the interference element free regions.

Preferably, software is configured to direct the imager to disregard the signal of the analyte from the interference element regions.

Preferably, the software is configured to direct the imager to increase signal contrast of the signals from the interference element regions to the signals from the interference element free regions Preferably, the software is configured to direct the detector to calculate a ratio of the signal from the interference element regions to the interference element free regions.

Preferably, the mobile apparatus is a smart phone.

Preferably, the mobile apparatus comprises a set of instructions that, when executed, direct the apparatus to capture one or more images of the sample, Preferably, the mobile apparatus comprises a light source that is configured to illuminate the sample.

Preferably, the mobile apparatus comprises a display that is configured to show the presence and/or amount of the analyte.

Preferably, the mobile apparatus comprises a set of instructions that, when executed, direct the detector to display the presence and/or amount of the analyte.

Preferably, the mobile apparatus is configured to transmit detection results to a third party.

Preferably, the adaptor comprises a filter that is configured to filter signals from the sample.

Preferably, the adaptor comprises a card slot, into which the device can be inserted.

Preferably, the adaptor comprises a slider that facilitates the insertion of the device into the card slot.

Preferably, the adaptor comprises a holder frame that is configured to removably connect to the mobile apparatus.

Preferably, the adaptor comprises an optical box that comprises one or more optical components that are configured to enhance the signal from the sample.

Preferably, the apparatus or method are used for detection of proteins, peptides, nucleic acids, synthetic compounds, inorganic compounds, organic compounds, bacteria, virus, cells, tissues, nanoparticles, and other molecules, compounds, mixtures and substances thereof.

Preferably, the apparatus or method are used for diagnostics, management, and/or prevention of human diseases and conditions.

Preferably, the apparatus or method are used for diagnostics, management, and/or prevention of veterinary diseases and conditions, or for diagnostics, management, and/or prevention of plant diseases and conditions.

Preferably, the apparatus or method are used for environments testing and decontamination.

Preferably, the apparatus or method are used for agricultural or veterinary applications.

Preferably, the apparatus or method are used for food testing.

Preferably, the apparatus or method are used for drug testing and prevention.

Preferably, the apparatus or method are used for detecting and/or measuring an analyte in blood.

Preferably, the apparatus or method are used for a colorimetric assay.

Preferably, the apparatus or method are used for a fluorescence assay.

Preferably, the signal related to the analyte is an electrical signal or an optical signal.

Preferably, the signal related to the analyte is an optical signal that allows the imager to capture images of the interference element rich region and the interference element poor region.

Preferably, the signal related to the analyte is from a colorimetric reaction.

Preferably, the signal related to the analyte is produced by illuminating the sample with an illumination source.

Preferably, the plates are movable relative to each.

Preferably, the spacers are fixed on one or both of the plates and have a uniform height.

Preferably, the first plate and second plate are configured to compress the sample into a layer of uniform thickness that substantially equals the height of the spacers.

Preferably, the spacers have a uniform height of 1 mm or less, 500 µm or less, 400 µm or less, 300 µm or less, 200 µm or less, 175 µm or less, 150 µm or less, 125 µm or less, 100 µm or less, 75 µm or less, 50 µm or less, 40 µm or less, 30 µm or less, 20 µm or less, 10 µm or less, 5 µm or less, 4 µm or less, 3 µm or less, 2 µm or less, 1.8 µm or less, 1.5 µm or less, 1 µm or less, 0.5 µm or less, 0.2 µm or less, 0.1 µm or less, 50 nm or less, 20 nm or less, 10 nm or less, or in a range between any of the two values.

Preferably, the spacers have a uniform height in the range of 0.5-2 µm, 0.5-3 µm, 0.5-5 µm, 0.5-10 µm, 0.5-20 µm, 0.5-30 µm, or 0.5-50 µm.

Preferably, at least one of the plates has a thickness of 100 mm or less, 50 mm or less, 25 mm or less, 10 mm or less, 5 mm or less, 1 mm or less, 500 µm or less, 400 µm or less, 300 µm or less, 200 µm or less, 175 µm or less, 150 µm or less, 125 µm or less, 100 µm or less, 75 µm or less, 50 µm or less, 40 µm or less, 30 µm or less, 20 µm or less, 10 µm or less, 5 µm or less, 4 µm or less, 3 µm or less, 2 µm or less, 1.8 µm or less, 1.5 µm or less, 1 µm or less, 0.5 µm or less, 0.2 µm or less, or 0.1 µm or less, or in a range between any of the two values.

Preferably, at least one of the plates has a thickness in the range of 0.5 to 1.5 mm; around 1 mm; in the range of 0.15 to 0.2 mm; or around 0.175 mm.

Preferably, at least one of the plates has a lateral area of 1 $mm^2$ or less, 10 $mm^2$ or less, 25 $mm^2$ or less, 50 $mm^2$ or less, 75 $mm^2$ or less, 1 $cm^2$ (square centimeter) or less, 2 $cm^2$ or less, 3 $cm^2$ or less, 4 $cm^2$ or less, 5 $cm^2$ or less, 10 $cm^2$ or less, 100 $cm^2$ or less, 500 $cm^2$ or less, 1000 $cm^2$ or less, 5000 $cm^2$ or less, 10,000 $cm^2$ or less, 10,000 $cm^2$ or less, or in a range between any two of these values Preferably, at least one of the plates has a lateral area of in the range of 500 to 1000 $mm^2$; or around 750 $mm^2$ Preferably, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

Preferably, the thickness of the flexible plate times the Young's modulus of the flexible plate is in the range 60 to 750 GPa-µm.

Preferably, for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ $µm^3$/GPa.

Preferably, one or both plates comprises a location marker, either on a surface of or inside the plate, that provide information of a location of the plate.

Preferably, one or both plates comprises a scale marker, either on a surface of or inside the plate, that provide information of a lateral dimension of a structure of the sample and/or the plate.

Preferably, one or both plates comprises an image marker, either on a surface of or inside the plate, that assists an imaging of the sample.

Preferably, the inter-spacer distance is in the range of 7 µm to 50 µm.

Preferably, the inter-spacer distance is in the range of 50 µm to 120 µm.

Preferably, the inter-spacer distance is in the range of 120 µm to 200 µm.

Preferably, the spacers are pillars with a cross-sectional shape selected from round, polygonal, circular, square, rectangular, oval, elliptical, or any combination of the same.

Preferably, the spacers have a pillar shape and have a substantially flat top surface, wherein, for each spacer, the ratio of the lateral dimension of the spacer to its height is at least 1.

Preferably, each spacer has the ratio of the lateral dimension of the spacer to its height is at least 1.

Preferably, the minimum lateral dimension of spacer is less than or substantially equal to the minimum dimension of an analyte in the sample.

Preferably, the minimum lateral dimension of spacer is in the range of 0.5 µm to 100 µm.

Preferably, the minimum lateral dimension of spacer is in the range of 0.5 µm to 10 µm.

Preferably, the spacers have a pillar shape, and the sidewall corners of the spacers have a round shape with a radius of curvature at least 1 µm.

Preferably, the spacers have a density of at least 100/mm$^2$.

Preferably, the spacers have a density of at least 1000/mm$^2$.

Preferably, at least one of the plates is transparent Preferably, at least one of the plates is made from a flexible polymer.

Preferably, for a pressure that compresses the plates, the spacers are not compressible and/or, independently, only one of the plates is flexible.

the flexible plate has a thickness in the range of 10 µm to 200 µm.

Preferably, the variation of sample thickness is less than 30%.

Preferably, the variation of sample thickness is less than 10%.

Preferably, the variation of sample thickness is less than 5%.

Preferably, the first and second plates are connected and are configured to be changed from the open configuration to the closed configuration by folding the plates.

Preferably, the first and second plates are connected by a hinge and are configured to be changed from the open configuration to the closed configuration by folding the plates along the hinge.

Preferably, the first and second plates are connected by a hinge that is a separate material to the plates, and are configured to be changed from the open configuration to the closed configuration by folding the plates along the hinge.

Preferably, the first and second plates are made in a single piece of material and are configured to be changed from the open configuration to the closed configuration by folding the plates.

Preferably, the layer of uniform thickness sample is uniform over a lateral area that is at least 1 mm$^2$.

Preferably, the spacers are fixed on a plate by directly embossing the plate or injection molding of the plate.

the materials of the plate and the spacers are selected from polystyrene, PMMA, PC, COC, COP, or another plastic.

Related Documents and Additional Examples

The present invention comprises a variety of embodiments, which can be combined in multiple ways as long as the various components do not contradict one another. The embodiments should be regarded as a single invention file: each filing has other filing as the references and is referenced in its entirety and for all purpose, rather than as a discrete independent. These embodiments include not only the disclosures in the current file, but the documents that are herein referenced, incorporated, or to which priority is claimed.

(1) Definitions

The terms used in describing the devices/apparatus, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

(2) Sample

The devices/apparatus, systems, and methods herein disclosed can be applied to manipulation and detection of various types of samples. The samples are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for samples such as but not limited to diagnostic samples, clinical samples, environmental samples and foodstuff samples. The types of sample include but are not limited to the samples listed, described and/or summarized in PCT Application (designating U.S) Nos. PCT/US2016/045437 and PCT/US0216/051775, which were respectively filed on Aug. 10, 2016 and Sep. 14, 2016, and are hereby incorporated by reference by their entireties.

For example, in some embodiments, the devices, apparatus, systems, and methods herein disclosed are used for a sample that comprises cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, ser\um, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In some embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In some embodiments, the devices, apparatus, systems, and methods herein disclosed are used for a foodstuff sample, which is suitable or has the potential to become suitable for animal consumption, e.g., human consumption. In some embodiments, a foodstuff sample comprises raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter ($\mu L$, "uL" herein) or less, 500 $\mu L$ or less, 300 $\mu L$ or less, 250 $\mu L$ or less, 200 $\mu L$ or less, 170 $\mu L$ or less, 150 $\mu L$ or less, 125 $\mu L$ or less, 100 $\mu L$ or less, 75 $\mu L$ or less, 50 $\mu L$ or less, 25 $\mu L$ or less, 20 $\mu L$ or less, 15 $\mu L$ or less, 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 $\mu L$ or less, 1 $\mu L$ or less, or a range between any two of the values.

In some embodiments, the volume of the sample includes, but is not limited to, about 100 $\mu L$ or less, 75 $\mu L$ or less, 50 $\mu L$ or less, 25 $\mu L$ or less, 20 $\mu L$ or less, 15 $\mu L$ or less, 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 $\mu L$ or less, 1 $\mu L$ or less, or a range between any two of the values. In some embodiments, the volume of the sample includes, but is not limited to, about 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 $\mu L$ or less, 1 $\mu L$ or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

(3) Q-Card, Spacers and Uniform Sample Thickness

The devices/apparatus, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX card refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX card refers the device that perform a QMAX (e.g. CROF) process on a sample, and have or not have a hinge that connect the two plates.

The term "QMAX card with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

In using QMAX card, the two plates need to be open first for sample deposition. However, in some embodiments, the QMAX card from a package has the two plates are in contact each other (e.g. a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate.

In the QMAX assay platform, a QMAX card uses two plates to manipulate the shape of a sample into a thin layer (e.g. by compressing). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 µm.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plates is a thin plastic film (175 µm thick PMA), such separation can be difficult to perform by hand. The present invention intends to provide the devices and methods that make the operation of certain assays, such as the QMAX card assay, easy and fast.

In some embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In some embodiments, the QMAX device comprises one or more hinges that can control the rotation of more than two plates.

In some embodiments, the hinge is made from a metallic material that is selected from a group consisting of gold, silver, copper, aluminum, iron, tin, platinum, nickel, cobalt, alloys, or any combination of thereof. In some embodiments, the hinge comprises a single layer, which is made from a polymer material, such as but not limited to plastics. The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyamide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In some embodiments, the polymer material is selected from polystyrene, PMMB, PC, COC, COP, other plastic, or any combination of thereof.

In essence, the term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

In some embodiments, human hands can be used to press the plates into a closed configuration; In some embodiments, human hands can be used to press the sample into a thin layer. The manners in which hand pressing is employed are described and/or summarized in PCT Application (designating U.S.) Nos. PCT/US2016/045437 filed on Aug. 10, 2016 and PCT/US0216/051775 filed on Sep. 14, 2016, and in US Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference by their entireties.

In some embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g. less than 5%, 10%, 15%, or 20% variability).

(4) Hinges, Opening Notches, Recessed Edge and Sliders

The devices/apparatus, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/431,639, which was filed on Dec. 9, 2016, U.S. Provisional Application No. 62/456,065, which was filed on Feb. 7, 2017, U.S. Provisional Application Nos. 62/456,287 and 62/456,504, which was filed on Feb. 8, 2017, and U.S. Provisional Application No. 62/539,660, which was filed on Aug. 1, 2017, all of which applications are incorporated herein in their entireties for all purposes.

In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates. In certain embodiments, the trenches limit the flow of the sample on the plate.

(5) Q-Card and Adaptor

The devices/apparatus, systems, and methods herein disclosed can include or use Q-cards for sample detection, analysis, and quantification. In some embodiments, the Q-card is used together with an adaptor that is configured to accommodate the Q-card and connect to a mobile device so that the sample in the Q-card can be imaged, analyzed, and/or measured by the mobile device. The structure, material, function, variation, dimension and connection of the Q-card, the adaptor, and the mobile are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, all of which applications are incorporated herein in their entireties for all purposes.

In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g. a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample.

(6) Smartphone Detection System

The devices/apparatus, systems, and methods herein disclosed can include or use Q-cards for sample detection, analysis, and quantification. In some embodiments, the Q-card is used together with an adaptor that can connect the Q-card with a smartphone detection system. In some embodiments, the smartphone comprises a camera and/or an illumination source The smartphone detection system, as well the associated hardware and software are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, all of which applications are incorporated herein in their entireties for all purposes.

In some embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

In some embodiments, the smartphone is an iPhone™, an Android™ phone, or a Windows™ phone.

(7) Detection Methods

The devices/apparatus, systems, and methods herein disclosed can include or be used in various types of detection methods. The detection methods are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287, 62/456,528, 62/456,631, 62/456,522, 62/456,598, 62/456,603, and 62/456,628, which were filed on Feb. 8, 2017, U.S. Provisional Application Nos. 62/459,276, 62/456,904, 62/457,075, and 62/457,009, which were filed on Feb. 9, 2017, and U.S. Provisional Application Nos. 62/459,303, 62/459,337, and 62/459,598, which were filed on Feb. 15, 2017, and U.S. Provisional Application Nos. 62/460,083, 62/460,076, which were filed on Feb. 16, 2017, all of which applications are incorporated herein in their entireties for all purposes.

(8) Labels, Capture Agent and Detection Agent

The devices/apparatus, systems, and methods herein disclosed can employ various types of labels, capture agents, and detection agents that are used for analytes detection. The labels are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP; a GFP from another species such as *Renilla reniformis, Renilla mulleri,* or *Ptilosarcus guernyi*; "humanized" recombinant GFP (hrGFP); any of a variety of fluorescent and colored proteins from Anthozoan species; combinations thereof; and the like.

In any embodiment, the QMAX device can contain a plurality of capture agents and/or detection agents that each bind to a biomarker selected from Tables B1, B2, B3 and/or B7 in U.S. Provisional Application No. 62/234,538 and/or PCT Application No. PCT/US2016/054025, wherein the reading step d) includes obtaining a measure of the amount of the plurality of biomarkers in the sample, and wherein the amount of the plurality of biomarkers in the sample is diagnostic of a disease or condition.

In any embodiment, the capture agent and/or detection agents can be an antibody epitope and the biomarker can be an antibody that binds to the antibody epitope. In some embodiments, the antibody epitope includes a biomolecule, or a fragment thereof, selected from Tables B4, B5 or B6 in U.S. Provisional Application No. 62/234,538 and/or PCT Application No. PCT/US2016/054025. In some embodiments, the antibody epitope includes an allergen, or a fragment thereof, selected from Table B5. In some embodiments, the antibody epitope includes an infectious agent-derived biomolecule, or a fragment thereof, selected from Table B6 in U.S. Provisional Application No. 62/234,538 and/or PCT Application No. PCT/US2016/054025.

In any embodiment, the QMAX device can contain a plurality of antibody epitopes selected from Tables B4, B5 and/or B6 in U.S. Provisional Application No. 62/234,538 and/or PCT Application No. PCT/US2016/054025, wherein the reading step d) includes obtaining a measure of the amount of a plurality of epitope-binding antibodies in the sample, and wherein the amount of the plurality of epitope-binding antibodies in the sample is diagnostic of a disease or condition.

(9) Analytes

The devices/apparatus, systems, and methods herein disclosed can be applied to manipulation and detection of various types of analytes (including biomarkers). The analytes are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases. The analytes, biomarkers, and/or diseases that can be detected and/or measured with the devices, apparatus, systems, and/or method of the present invention include the analytes, biomarkers, and/or diseases listed, described and/or summarized in PCT Application (designating U.S.) Nos. PCT/US2016/045437 filed on Aug. 10, 2016, and PCT Application No. PCT/US2016/054025 filed on Sep. 27, 2016, and U.S. Provisional Application Nos. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the sample can be a diagnostic sample obtained from a subject, the analyte can be a biomarker, and the measured the amount of the analyte in the sample can be diagnostic of a disease or a condition.

In any embodiment, the devices, apparatus, systems, and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7.

In any embodiment, the applying step b) can include isolating miRNA from the sample to generate an isolated miRNA sample, and applying the isolated miRNA sample to the disk-coupled dots-on-pillar antenna (QMAX device) array.

In any embodiment, the QMAX device can contain a plurality of capture agents that each bind to a biomarker selected from Tables B1, B2, B3 and/or B7, wherein the reading step d) includes obtaining a measure of the amount of the plurality of biomarkers in the sample, and wherein the amount of the plurality of biomarkers in the sample is diagnostic of a disease or condition.

In any embodiment, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In some embodiments, the antibody epitope includes an infectious agent-derived biomolecule, or a fragment thereof, selected from Table B6.

In any embodiment, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition.

In any embodiment, the sample can be an environmental sample, and wherein the analyte can be an environmental marker. In some embodiments, the environmental marker is selected from Table B8 in U.S. Provisional Application No. 62/234,538 and/or PCT Application No. PCT/US2016/054025.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the QMAX device array can include a plurality of capture agents that each binds to an environmental marker selected from Table B8, and wherein the reading step d) can include obtaining a measure of the amount of the plurality of environmental markers in the sample.

In any embodiment, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained.

In any embodiment, the devices, apparatus, systems, and methods herein disclosed can include a plurality of capture agents that each binds to a foodstuff marker selected from Table B9 from in U.S. Provisional Application No. 62/234,538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption.

provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the QMAX device can be employed. Suitable methods can include using a pipet, dropper, syringe, etc. In certain embodiments, when the QMAX device is located on a support in a dipstick format, as described below, the sample can be applied to the QMAX device by dipping a sample-receiving area of the dipstick into the sample.

A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the QMAX device to remove unbound sample components can be done in any convenient manner, as described above. In certain embodiments, the surface of the QMAX device is washed using binding buffer to remove unbound sample components.

Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

(10) Applications

The devices/apparatus, systems, and methods herein disclosed can be used for various applications (fields and samples). The applications are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

(11) Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/045437 filed on Aug. 10, 2016, and U.S. Provisional Application Nos. 62,431,639 filed on Dec. 9, 2016 and 62/456,287 filed on Feb. 8, 2017, which are all hereby incorporated by reference by their entireties.

In some embodiments, the dimensions are listed in the Tables below:

Plates:

| Parameters | Embodiments | Preferred Embodiments |
|---|---|---|
| Shape | round, ellipse, rectangle, triangle, polygonal, ring-shaped, or any superposition of these shapes; the two (or more) plates of the QMAX card can have the same size and/or shape, or different size and/or shape; | at least one of the two (or more) plates of the QMAX card has round corners for user safety concerns, wherein the round corners have a diameter of 100 μm or less, 200 μm or less, 500 μm or less, |

| Parameters | Embodiments | Preferred Embodiments |
| --- | --- | --- |
| | | 1 mm or less, 2 mm or less, 5 mm or less, 10 mm or less, 50 mm or less, or in a range between any two of the values. |
| Thickness | the average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values | For at least one of the plates is in the range of 0.5 to 1.5 mm; around 1 mm; in the range of 0.15 to 0.2 mm; or around 0.175 mm |
| Lateral Area | For at least one of the plate is 1 mm² (square millimeter) or less, 10 mm² or less, 25 mm² or less, 50 mm² or less, 75 mm² or less, 1 cm² (square centimeter) or less, 2 cm² or less, 3 cm² or less, 4 cm² or less, 5 cm² or less, 10 cm² or less, 100 cm² or less, 500 cm² or less, 1000 cm² or less, 5000 cm² or less, 10,000 cm² or less, 10,000 cm² or less, or in a range between any two of these values | For at least one plate of the QMAX card is in the range of 500 to 1000 mm²; or around 750 mm². |
| Lateral Linear Dimension (width, length, or diameter, etc.) | For at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values | For at least one plate of the QMAX card is in the range of 20 to 30 mm; or around 24 mm |
| Recess width | 1 μm or less, 10 μm or less, 20 μm or less, 30 μm or less, 40 μm or less, 50 μm or less, 100 μm or less, 200 um or less, 300 μm or less, 400 μm or less, 500 μm or less, 7500 μm or less, 1 mm or less, 5 mm or less, 10 mm or less, 100 mm or less, or 1000 mm or less, or in a range between any two of these values. | In the range of 1 mm to 10 mm; Or About 5 mm |

Hinge:

| Parameters | Embodiments | Preferred Embodiments |
| --- | --- | --- |
| Number | 1, 2, 3, 4, 5, or more | 1 or 2 |
| Length of Hinge Joint | 1 mm or less, 2 mm or less, 3 mm or less, 4 mm or less, 5 mm or less, 10 mm or less, 15 mm or less, 20 mm or less, 25 mm or less, 30 mm or less, 40 mm or less, 50 mm or less, 100 mm or less, 200 mm or less, or 500 mm or less, or in a range between any two of these values | In the range of 5 mm to 30 mm. |
| Ratio (hinge joint length vs. aligning plate edge length | 1.5 or less, 1 or less, 0.9 or less, 0.8 or less, 0.7 or less, 0.6 or less, 0.5 or less, 0.4 or less, 0.3 or less, 0.2 or less, 0.1 or less, 0.05 or less or in a range between any two of these values. | In the range of 0.2 to 1; or about 1 |
| Area | 1 mm² or less, 5 mm² or less, 10 mm² or less, 20 mm² or less, 30 mm² or less, 40 mm² or less, 50 mm² or less, 100 mm² or less, 200 mm² or less, 500 mm² or less, or in a range between any of the two values | In the range of 20 to 200 mm²; or about 120 mm² |
| Ratio (hinge area vs. plate area) | 1 or less, 0.9 or less, 0.8 or less, 0.7 or less, 0.6 or less, 0.5 or less, 0.4 or less, 0.3 or less, 0.2 or less, 0.1 or less, 0.05 or less, 0.01 or less or in a range between any two of these values | In the range of 0.05 to 0.2, around 0.15 |
| Max. Open Degree | 15 or less, 30 or less, 45 or less, 60 or less, 75 or less, 90 or less, 105 or less, 120 or less, 135 or less, 150 or less, 165 or less, 180 or less, 195 or less, 210 or less, 225 or less, 240 or less, 255 or less, 270 or less, 285 or less, 300 or less, 315 or less, 330 or less, 345 or less or 360 or less degrees, or in a range between any two of these values | In the range of 90 to 180 degrees |
| No. of Layers | 1, 2, 3, 4, 5, or more | 1 or 2 |
| Layer thickness | 0.1 μm or less, 1 μm or less, 2 μm or less, 3 μm or less, 5 μm or less, 10 μm or less, 20 μm or less, 30 μm or less, 50 μm or less, 100 μm or less, 200 μm or less, 300 um or less, 500 μm or less, 1 mm or less, 2 mm or less, and a range between any two of these values | In the range of 20 μm to 1 mm; or Around 50 μm |

-continued

| Parameters | Embodiments | Preferred Embodiments |
|---|---|---|
| Angle-maintaining | Limiting the angle adjustment with no more than ±90, ±45, ±30, ±25, ±20, ±15, ±10, ±8, ±6, ±5, ±4, ±3, ±2, or ±1, or in a range between any two of these values | No more than ±2 |

Notch:

| Parameters | Embodiments | Preferred Embodiments |
|---|---|---|
| Number | 1, 2, 3, 4, 5, or more | 1 or 2 |
| Shape | round, ellipse, rectangle, triangle, polygon, ring-shaped, or any superposition or portion of these shapes. | Part of a circle |
| Positioning | Any location along any edge except the hinge edge, or any corner joint by non-hinge edges | |
| Lateral Linear Dimension (Length along the edge, radius, etc.) | 1 mm or less, 2.5 mm or less, 5 mm or less, 10 mm or less, 15 mm or less, 20 mm or less, 25 mm or less, 30 mm or less, 40 mm or less, 50 mm or less, or in a range between any two of these values | In the range of 5 mm to 15 mm; or about 10 mm |
| Area | 1 $mm^2$ (square millimeter) or less, 10 $mm^2$ or less, 25 $mm^2$ or less, 50 $mm^2$ or less, 75 $mm^2$ or less or in a range between any two of these values. | In the range of 10 to 150 $mm^2$; or about 50 $mm^2$ |

Trench:

| Parameters | Embodiments | Preferred Embodiments |
|---|---|---|
| Number | 1, 2, 3, 4, 5, or more | 1 or 2 |
| Shape | Closed (round, ellipse, rectangle, triangle, polygon, ring-shaped, or any superposition or portion of these shapes) or open-ended (straight line, curved line, arc, branched tree, or any other shape with open endings); | |
| Length | 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values | |
| Cross-sectional Area | 0.001 $mm^2$ or less, 0.005 $mm^2$ or less, 0.01 $mm^2$ or less, 0.05 $mm^2$ or less, 0.1 $mm^2$ or less, 0.5 $mm^2$ or less, 1 $mm^2$ or less, 2 $mm^2$ or less, 5 $mm^2$ or less, 10 $mm^2$ or less, 20 $mm^2$ or less, or in a range between any two of these values. | |
| Volume | 0.1 μL or more, 0.5 μL or more, 1 μL or more, 2 μL or more, 5 μL or more, 10 μL or more, 30 μL or more, 50 μL or more, 100 μL or more, 500 μL or more, 1 mL or more, or in a range between any two of these values | In the range of 1 μL to 20 μL; or About 5 μL |

Receptacle Slot

| Parameters | Embodiments | Preferred Embodiments |
|---|---|---|
| Shape of receiving area | round, ellipse, rectangle, triangle, polygon, ring-shaped, or any superposition of these shapes; | |
| Difference between sliding track gap size and card thickness | 100 nm, 500 nm, 1 μm, 2 μm, 5 μm, 10 μm, 50 μm, 100 μm, 300 μm, 500 μm, 1 mm, 2 mm, 5 mm, 1 cm, or in a range between any two of the values. | In the range of 50 to 300 μm; or about 75 μm |
| Difference between receiving area and card area | 1 $mm^2$ (square millimeter) or less, 10 $mm^2$ or less, 25 $mm^2$ or less, 50 $mm^2$ or less, 75 $mm^2$ or less, 1 $cm^2$ (square centimeter) or less, 2 $cm^2$ or less, 3 $cm^2$ or less, 4 $cm^2$ or less, 5 $cm^2$ or less, 10 $cm^2$ or less, 100 $cm^2$ or less, or in a range between any of the two values. | |

(12) Cloud

The devices/apparatus, systems, and methods herein disclosed can employ cloud technology for data transfer, storage, and/or analysis. The related cloud technologies are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In some embodiments, the data (e.g. images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function can additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") can refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity can optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

What is claimed is:

1. A device for assaying a sample, comprising:
    a first plate,
    a second plate,
    spacers, and a sample containment ring,
    wherein:
    (i) the first plate and the second plate are movable relative to each other into different configurations, including an open configuration and a closed configuration;
    (ii) each of the plate comprises a surface that has a sample contact area for depositing or contacting a sample that contains or is suspected of containing an analyte; and
    (iii) the sample containment ring is on the surface of one of the first and second plates and at least partially surrounds the sample contact area of the one of the first and second plates;
    wherein the sample containment ring is configured to reduce or prevent the sample deposited on the one of the first and second plates from flowing out of the edge of the one of the first and second plates, and the sample containment ring comprises at least one recessed cavity that is below the surface of the one of the first and second plates, wherein the at least one recessed cavity comprises at least one trench or well;

wherein the spacers are fixed on the surface of at least one of the first and second plates, and at least one of the spacers is inside either sample contact area; and wherein in the open configuration, the first and second plates are partially or entirely separated apart so that the sample can be deposited on either sample contact area of the first and second plates.

2. The device of claim 1, wherein the sample containment ring comprises a plurality of wells that are configured to hold an overflow portion of the sample.

3. The device of claim 1, wherein the sample containment ring comprises a plurality of trenches that are configured to hold an overflow portion of the sample.

4. The device of claim 1, the at least one recessed cavity comprises a plurality of wells and/or trenches.

5. The device of claim 1, wherein the sample containment ring is an enclosed ring trench.

6. The device of claim 1, wherein the sample containment ring has a maximum storage volume that is larger than a maximum volume of the sample contact area on one of the first and second plates in the closed configuration.

7. The device of claim 1, wherein the at least one recessed cavity comprises a segmented trench.

8. The device of claim 1, wherein the sample containment ring comprises a plurality of wells that are partially or entirely around the sample contact areas to block overflow of the sample deposited between the first and second plates in the closed configuration.

9. The device of claim 1, wherein the sample containment ring comprises a trench continuously surrounding either sample contact area, the trench having a width of 1000 μm or less.

10. The device of claim 1, wherein the at least one trench continuously surrounds either sample contact area, and the at least one trench has a width in a range of from 0.2 μm to 200 μm, a depth in a range of 0.02 μm to 20 μm, and a total length in a range of 20 mm to 400 mm.

11. The device of claim 1, the sample containment ring has a structure that does not, in the closed configuration, touch the surface of the other plate.

12. The device of claim 1, wherein the sample containment ring comprises a plurality of separate wells that are periodically arranged and a continuous trench, wherein walls of the trench and wells are entirely disposed below the surface of the one of the first and second plates.

13. The device of claim 1, wherein in the open configuration, an average spacing between the sample contact areas of the first and second plates is larger than 300 μm; and wherein, in the closed configuration, an average spacing between the sample contact areas of the first and second plates is from 0.1 μm to 250 μm.

14. The device of claim 1, wherein, in the closed configuration, the spacers are located between the first and second plates and in contact with the surfaces of the first and second plates.

15. The device of claim 14, wherein the sample containment ring further comprises a wall that impedes the sample from flowing out from an edge of a plate, and the wall is shorter than the average spacing of the first and second plates in the closed configuration.

16. The device of claim 14, wherein the sample containment ring further comprises a plurality of walls that impede the sample from flowing out from edges of the surfaces of the first and second plates, and the walls are shorter than the average spacing of the first and second plates.

17. The device of claim 16, wherein the walls are disposed at one of the first and second plates and are partially or entirely around the sample contact areas of the first and second plates in the closed configuration to impede overflow of the sample.

18. The device of claim 14, wherein the first and second plates are connected by a hinge to enable a transition from the open configuration to the closed configuration by folding the first and second plates along the hinge.

19. The device of claim 14, wherein the sample containment ring and the spacers are fabricated by directly embossing or injection molding of one or both of the first and second plates.

20. The device of claim 14, wherein materials of the first and second plates and the spacers are independently selected from the group consisting of polystyrene, PMMA, PC, COC, and COP.

21. The device of claim 14, wherein a ratio of a maximum sample volume stored in the sample containment ring to a maximum volume of either sample contact area is at least 1.

22. The device of claim 14, wherein the volume of the sample contact area is in a range of 1 μL to 50 μL.

23. The device of claim 14, wherein the at least one recessed cavity comprises a plurality of wells that are organized as at least one row around either sample contact area.

24. The device of claim 14, wherein the spacers have a uniform height.

25. The device of claim 14, wherein the at least one recessed cavity comprises a plurality of wells, and each of the wells has a volume in a range of 0.001 μL to 5 μL.

26. The device of claim 14, wherein each of the spacers is a pillar with a cross-sectional shape selected from round, polygonal, circular, square, rectangular, oval, elliptical, and any combination of the same.

27. The device of claim 14, wherein the spacers have an inter-spacer distance from 7 um to 200 um.

28. The device of claim 27, wherein one of the first and second plates is flexible and the fourth power of the inter-spacer-distance (ISD) divided by the thickness of the flexible plate (h) and the Young's modulus (E) of the flexible plate, $ISD^4/(hE)$, is equal to or less than $10^6$ um$^3$/GPa, and the thickness of the flexible plate times the Young's modulus of the flexible plate is in the range of 60 to 750 GPa-μm.

29. The device of claim 1, wherein the sample containment ring comprises a well that is configured to hold an overflow portion of the sample.

30. The device of claim 29, wherein the sample containment ring comprises a plurality of wells that are organized as one row around either sample contact area.

31. The device of claim 29, wherein the sample containment ring comprises a plurality of wells that are organized as two or more rows around either sample contact area.

32. The device of claim 1, wherein the sample containment ring comprises at least one trench that is configured to hold an overflow portion of the sample.

33. The device of claim 32, wherein the at least one recessed cavity comprises a continuous trench that encircles either sample contact area.

34. The device of claim 32, wherein the sample containment ring comprises a plurality of segmented trenches that surround the sample contact area of the surface where the sample containment ring is disposed.

35. The device of claim 32, wherein the at least one recessed cavity comprises:

a plurality of trenches, each of the trenches having a width in a range from 0.2 μm to 200 μm and having a depth in a range from 0.02 µm to 20 µm, and wherein a total length of the trenches is in a range from 20 mm to 400 mm.

36. A method for assaying a sample containing or suspected of containing an analyte, comprising:
obtaining the device of claim 1 or 14;
obtaining the sample;
depositing the sample on one or both of the sample contact areas when the first and second plates are in the open configuration; and
pressing the first and second plates into the closed configuration to compress at least part of the sample into a layer with a uniform thickness.

37. The method of claim 36, wherein the at least one recessed cavity comprises a well, and the well has a shape selected from the group consisting of a rectangle, a cylinder, a spheroidal cap, and a wedge.

38. The method of claim 36, wherein the sample is an original, diluted, or processed liquid form of: a stool, amniotic fluid, aqueous humour, vitreous humour, blood, whole blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, or exhaled breath condensate.

39. The method of claim 36, wherein the sample contains an analyte, and the analyte is a biomarker, an environmental marker, or a foodstuff marker.

40. The method of claim 36, wherein the at least one recessed cavity comprises a plurality of wells that are organized as at least one row around either sample contact area.

41. A system for assaying a sample containing or suspected of containing an analyte, comprising:
the device of claim 1 or the device of claim 14; and
an apparatus for analyzing a signal from the analyte in the sample.

42. The system of claim 41, wherein the apparatus comprises a camera that images the sample and a communication unit that sends a signal to a remote location.

43. The system of claim 41, wherein the apparatus is a mobile apparatus that is configured to capture images of the sample and measure a signal related to an analyte in the images.

44. The system of claim 41, wherein the system is configured to detect or measure an analyte in blood.

45. The system of claim 41, wherein the system detects a colorimetric signal, a fluorescence signal, or both.

46. The system of claim 41, wherein the system detects a signal related to the analyte, and the signal is an electrical signal, an optical signal, or both.

* * * * *